United States Patent [19]
Chang et al.

[11] Patent Number: 5,916,872
[45] Date of Patent: Jun. 29, 1999

[54] CYCLIC PEPTIDES HAVING BROAD SPECTRUM ANTIMICROBIAL ACTIVITY

[75] Inventors: Conway Chang, San Francisco; Leo Gu, Saratoga; Jie Chen, Belmont, all of Calif.

[73] Assignee: IntraBiotics Pharmaceuticals, Inc., Mountain View, Calif.

[21] Appl. No.: 08/685,589

[22] Filed: Jul. 24, 1996

[51] Int. Cl.$^6$ .......................... A61K 38/00; A61K 38/12
[52] U.S. Cl. .................................. 514/9; 514/12; 514/13; 514/14; 530/317; 530/321; 530/324; 530/326; 530/327; 530/333; 530/334; 530/338; 530/345
[58] Field of Search .................................. 530/317, 321, 530/324, 326, 327, 333, 334, 338, 345; 514/11, 9, 12, 13, 14

[56] References Cited

U.S. PATENT DOCUMENTS

| | | | |
|---|---|---|---|
| 4,543,252 | 9/1985 | Lehrer et al. | 514/2 |
| 4,652,639 | 3/1987 | Stabinsky | 435/91.52 |
| 4,659,692 | 4/1987 | Lehrer et al. | 514/12 |
| 4,705,777 | 11/1987 | Lehrer et al. | 514/12 |
| 5,039,789 | 8/1991 | Fukuda et al. | 530/317 |
| 5,087,569 | 2/1992 | Gabay et al. | 435/212 |
| 5,126,257 | 6/1992 | Gabay et al. | 435/212 |
| 5,171,739 | 12/1992 | Scott et al. | 514/12 |
| 5,234,912 | 8/1993 | Marra et al. | 514/21 |
| 5,308,834 | 5/1994 | Scott et al. | 514/12 |
| 5,334,584 | 8/1994 | Scott et al. | 514/12 |
| 5,338,724 | 8/1994 | Gabay et al. | 514/12 |
| 5,422,424 | 6/1995 | Selsted et al. | 514/12 |
| 5,432,270 | 7/1995 | Zasloff et al. | 536/23.5 |
| 5,447,914 | 9/1995 | Travis et al. | 514/16 |
| 5,458,874 | 10/1995 | Pereira et al. | 424/85.1 |
| 5,459,235 | 10/1995 | Selsted et al. | 530/300 |
| 5,464,823 | 11/1995 | Lehrer et al. | 514/13 |
| 5,484,885 | 1/1996 | Pereira et al. | 530/326 |
| 5,635,594 | 6/1997 | Lehrer et al. | 530/317 |
| 5,693,486 | 12/1997 | Lehrer et al. | 435/69.1 |
| 5,708,154 | 1/1998 | Smith et al. | 536/23.1 |
| 5,804,558 | 9/1998 | Lehrer et al. | 514/13 |

FOREIGN PATENT DOCUMENTS

| | | |
|---|---|---|
| 272489 | 6/1988 | European Pat. Off. . |
| 545730 | 6/1993 | European Pat. Off. . |
| 89/11291 | 11/1989 | WIPO . |
| 93/19087 | 9/1993 | WIPO . |
| 93/24139 | 12/1993 | WIPO . |
| 94/21672 | 9/1994 | WIPO . |
| 95/03325 | 2/1995 | WIPO . |
| 95/10534 | 4/1995 | WIPO . |

OTHER PUBLICATIONS

Hu et al., 1991, "Isolation and Characterization of Corticostatic Peptides from Guinea Pig Bone Marrow," *Biochem. Biophys. Res. Commun.* 180:558–565.

Harwig, S. S. L. et al., 1996, "Intramolecular disulfide bonds enhance the antimicrobial and lytic activities of protegrins at physiological sodium chloride concentrations," *Eur. J. Biochem.* 240:352–357.

Yasin, B. et al., 1996, "Protegrins: Structural requirements for inactivating elementary bodies of *Chlamydia trachomatis*," *Infection and Immunity* 64(11):4863–4866.

Battersby et al., 1951, *J. Am. Chem. Soc.* 73:1887.

Schwyzer et al., 1957, *Helv. Chim. Acta* 40:624.

Laiken et al., 1969, *J. Biol. Chem.* 244:4454.

Zharikova et al., 1972, *Vestn. Mosk. Univ. Biol. Pochivoved* 27:110.

Myaskovskaya et al., 1973, *Vestn. Mosk. Univ. Biol. Pochivoved* 28:123.

Gibbons et al., 1975, *Biochemistry* 14:420.

Tamaki et al., 1995, *Int. J. Peptide Protein Res.* 45:299–302.

Hultmark et al., 1980, *Eur. J. Biochem.* 106:7–16.

Hultmark et al., 1982, *Eur. J. Biochem.* 127:207–217.

Lerner, 1982, "Tapping the Immunological Repertoire to Produce Antibodies of Predetermined Specificity," *Nature* 299: 592–596.

Matsumoto et al., 1982, "Amino Acids and Peptides, XXXV, Synthesis of Mouse Metallothionein I.(2). Synthesis of a Nonacosapeptide Corresponding to N–Terminal Sequence 1–29 (β–Fragment) of Mouse Metallothionein I and Related Peptides and Examination of Their Heavy Metal–Binding Properties," *Chem. and Pharma. Bulletin* 40:2701–2706.

Lehrer et al., 1985, "Direct Inactivation of Viruses by MCP–1 and MCP–2, Natural Peptide ntbiotics from Rabbit Leukocytes," *J. Virol.* 54:467–472.

Robson et al., 1986, "The Concept of Primary Structure," In: *Introduction to Proteins and Protein Engineering* Elsevier, NY, pp. 27–46.

Pongor, 1987, "The Use of Structural Profiles and Parametric Sequence Comparison in the Rational Design of Polypeptides," *Methods in Enzymology* 154:450–473.

Zasloff et al., 1987, *Proc. Natl. Acad. Sci. U.S.A.* 84:5449–5453.

Matsuyama and Natori, 1988, *J. Biol. Chem.* 263:17112–17116.

Nakamura et al., 1988, "Tachyplesin, a Class of Antimicrobial Peptide from the Hemocytes of the Horseshoe Crab (*Tachypleus Tridentatus*)," *J. Biol. Chem.* 263:16709–16713.

Zasloff et al., 1988, *Proc. Natl. Acad. Sci. U.S.A.* 85:910–913.

Casteels et al., 1989, *EMBO J.* 8:2387–2391.

Lambert et al., 1989, "Insect Immunity: Isolation from Immune Blood of the Dipteran *Phormia Terranovae* of Two Insect Antibacterial Peptides with Sequence Homology to Rabbit Lung Machophage Bactericidal Peptides," *Proc. Natl. Acad. Sci. U.S.A.* 88:262–265.

(List continued on next page.)

*Primary Examiner*—Cecilia J. Tsang
*Assistant Examiner*—Fabian Jameison
*Attorney, Agent, or Firm*—Pennie & Edmonds LLP

[57] ABSTRACT

The present invention provides cyclic peptides having broad spectrum antimicrobial activity. The peptides exhibit improved efficacy, bioavailability and/or serum half-life as compared with non-cyclized analogues.

18 Claims, 4 Drawing Sheets

OTHER PUBLICATIONS

Miyata et al., 1989, "Antimicrobial Peptides, Isolated from Horseshoe Crab Hemocytes, Tachyplesin II, and Polyphemusins I and II: Chemical Structures and Biological Activity," *J. Biochem.* 106:663–668.

Diamond et al., 1991, "Trachael Antimicrobial Peptide, a Cysteine–Rich Peptide from Mammalian Trachael Mucosa: Peptide Isolation and Cloning of a cDNA," *Proc. Natl. Acad. Sci. U.S.A.* 88:3952–3956.

Lehrer et al., 1991, "Defensins: Endogenous Antibiotic Peptides of Animal Cells," *Cell* 65:229–230.

Matsuzaki et al., 1991, "Interactions of an Antimicrobial Peptide, Tachyplesin I, with Lipid Membranes" *Biochim. Biophys. Acta* 1070:259–264.

Morimoto et al., 1991, "Inhibitory Effect of Tachyplesin I on the Proliferation of Human Immunodeficiency Virus in vitro," *Chemotherapy* 37:206–211.

Murakami et al., 1991, "Direct Virus Inactivation of Tachyplesin I and Its Isopeptides from Horseshoe Crab Hemocytes," *Chemotherapy* 37:327–334.

Olsson et al., 1991, "Molecular Parameters that Control the Association of Low Density Lipoprotein APO B–100 with Chondroitin Sulphate," *Biochim. Biophys. Acta* 1097:37–44.

Batemen et al., 1992, "The Levels and Biologic Action of the Human Neutrophil Granule Peptide HP–1 in Lung Tumors," *Peptides* 13:133–139.

Broekaert et al., 1992, "Antimicrobial Peptides for *Amaranthus caudatus* Seeds with Sequence Homology to the Cysteine/Glycine–Rich Domain of Chitin–Binding Proteins" *Biochemistry* 31:4308–4314.

Masuda et al., 1992, "A Novel Anti–HIV Synthetic Peptide T–22 ([Tyr5, 12, Lys7]–polyphemusin II)" *Biochem. Biophys. Res. Commun.* 189:845–850.

Nakashima et al., 1992, "Anti–Human Immunodeficiency Virus Activity of a Novel Synthetic Peptide, T22 ([Tyr–5, 12, Lys–7]Polyphemusin II): A Possible Inhibitor of Virus––Cell Fusion," *Antimicrobial Agents and Chemotherapy* 36:1249–1255.

Park et al., 1992, "Conformation of Tachplesin I from Tachypleus Tridentatus when Interacting with Lipid Matrices" *Biochemistry* 31:12241–12247.

Selsted et al., 1992, "Enteric Defensis: Antibiotic Peptide Components of Intestinal Host Defense," *The Journal of Cell Biology* 118:929–936.

Cornelissen et al., 1993, "Strategies for Control of Fungal Diseases with Transgenic Plants," *Plant Physiol.* 101:709–712.

Elsbach et al., 1993, "Bacterial/Permeability Increasing Protein and Host Defense Against Gram–Negative Bacteria and Endotoxin," *Current Opinion in Immunology* 5:103–107.

Hain et al., 1993, "Disease Resistance Results from Foreign Phytoalexin Expression in a Novel Plant," *Nature* 361:153–156.

Hoess et al., 1993, "Crystal Structure of an Endotoxin–Neutralizing Protein from the Horseshoe Crab, Limulus anti––LPS factor at 1.5 Å Resolution," *EMBO Journal* 12:3351–3356.

Kokryakov et al., 1993, "Protegrins: Leukocyte Antimicrobial Peptides that Combine Features of Corticostatic Defensins and Tachyplesins," *FEBS* 327:231–236.

Lehrer et al., 1993, "Defensins: Antimicrobial and Cytotoxic Peptides of Mamalian Cells," *Ann. Rev. Immunol.* 11:105–128.

Matsuzaki et al., 1993, "Role of Disulfinde Linkages in Tachyplesin–Lipid Interactions," *Biochemistry* 32:11704–11710.

Mirgorodskaya et al., 1993, "Primary Structure of Three Cationic Peptides from Porcine Neutrophils," *FEBS* 330:339–342.

Rustici et al., 1993, "Molecular Mapping and Detoxification of the Lipid A Binding Site by Synthetic Peptides," *Science* 259:361–364.

Schleusener et al., 1993, "Leukocyte Antimicrobial Peptides Kill Autoimmune T Cells," *Journal of Neuroimmunology* 47:199–202.

Selsted et al., 1993, "Purification, Primary Structures, and Antibacterial Activities of β–Defensins, a New Familty of Antimicrobial Peptides from Bovine Neutrophils," *J. Biol. Chem.* 268:6641–6648.

Storici et al., 1993, "A Novel cDNA Sequence Encoding a Pig Leukocyte Antimicrobial Peptide with a Cathelin–Like Pro–Sequence," *Biochem. Biophys. Res. Commun.* 196:1363–1368.

Tamamura et al., 1993, "Antimicrobial Activity and Conformation of Tachyplesin I and its Analogs," *Chemical and Pharmaceutical Bulletin* 41:978–980.

Tamamura et al., 1993, "A Comparative Study of the Solution Structure of Tachyplesin I and a Novel Anti–HIV Synthtic Peptide, T22, Determined by Nuclear Magnetic Resonance," *Biochim. Biophys. Acta* 1163:209–216.

Harwig et al., 1994, "Gallinacins: Cystein–Rich Antimicrobial Peptides of Chicken Leukocytes," *FEBS Letters* 342:281–285.

*Antimicrobial Peptides*, Ciba Foundation Symposium 186, John Wiley & Sons, New York (1994).

Zhao et al., 1994, "Identification of a New Member of the Protegrin Family by cDNA Cloning," *FEBS Letters* 346:285–288.

Harwig et al., 1995, "Prophenin–1, an Exceptionally Proline–Rich Antimicrobial Peptide from Porcine Leukocytes," *FEBS Letters* 362:65–69.

Harwig et al., 1995, "Determination of Disulphide Bridges in PG–2, an Anti–Microbial Peptide from Porcine Leukocytes," *J. Peptide Sci.* 3:207–215.

Maloy et al., 1995, "Structure–Activity Studies on Magainins and Other Host Defense Peptides," *Biopolymers (Peptide Science)* 37:105–122.

Selsted et al., 1995, "Primary Structures of Six Antimicrobial Peptides of Rabbit Peritoneal Neutrophils," *J. Biol. Chem.* 260(8):4579–4584.

Tamamura et al., 1995, "Synthesis of Protegrin–Related Peptides and their Antibacterial and Anti–Human Immunodeficiency Virus Activity," *Chemical and Pharmaceutical Bulletin* 43:853–858.

Zhao et al., 1995, "Structures of Genes for Two Cathelin–Associated Antimicrobial Peptides: Prophenin–2 and PR–39," *FEBS Letters* 376:130–134.

Zhao et al., 1995, "The Structure of Porcine Protegrin Genes," *FEBS Letters* 368:197–202.

Mangoni et al., 1996, *FEBS Letters* 383:93–98.

Masera et al., 1996, "Corticostatins/Defensins Inhibit in Vitro NK Activity and Cytokine Production by Human Peripheral Blood Mononuclear Cells," *Regulatory Peptides* 62:13–21.

CYCLIC PEPTIDES HAVING BROAD SPECTRUM ANTIMICROBIAL ACTIVITY

1. FIELD OF THE INVENTION

The present invention is directed to cyclic peptides having broad spectrum antimicrobial activity. The cyclic peptides are biocidal against a wide variety of pathogens, including clinically relevant vancomycin resistant *Enterococcus faecium*, methicillin resistant *Staphylococcus aureus* and penicillin-resistant *Streptococcus pneumoniae*. The cyclic peptides of the invention have improved efficacy, bioavailability and/or serum half-life as compared to non-cyclized analogues.

2. BACKGROUND OF THE INVENTION

With the recent dramatic rise of antibiotic-resistant pathogens and infectious diseases, the need for new antimicrobial agents is urgent (Cohen et al., 1992, *Science* 257:1050–1055). For example, recently strains of *Enterococcus faecium* that are resistant to vancomycin have been observed (Moellering, 1990, *Clin. Microbiol. Rev.* 3:46–65). As vancomycin is considered to be the antibiotic of last resort for several pathogens, strains resistant to vancomycin pose a serious health threat to society. Despite this urgency, in more than ten years only one completely different type of antibiotic, a streptogramin mixture called Synercid (Rhone-Poulenc Rorer, Collegeville, Pa.), has reached Phase III clinical trials (Pfeiffer, 1996, "New Anti-Microbial Therapies Described," *Genetic Engineering News* 16(8):1).

Recently, a new class of antimicrobial or antibiotic agents based on naturally-occurring antimicrobial peptides produced within plants, animals and insects have been discovered. These peptides include, among others, cecropins (Hultmark et al., 1980, *Eur. J. Biochem.* 106:7–16; Hultmark et al., 1982, *Eur. J. Biochem.* 127:207–217), apidaecins (Casteels et al., 1989, *EMBO J.* 8:2387–2391), magainins (Zasloff, 1987, *Proc. Natl. Acad. Sci. U.S.A.* 84:5449–5453; Zasloff et al., 1988, *Proc. Natl. Acad. Sci. U.S.A.* 85:910–913), tachyplesins and analogues of tachyplesins such as polyphemusins (Nakamura et al., 1988, *J. Biol. Chem.* 263:16709–16713; Miyata et al., 1989, *J. Biochem.* 106:663–668), defensins (Lehrer et al., 1991, *Cell* 64:229–230; Lehrer et al., 1993, *Ann. Rev. Immunol.* 11:105–128; U.S. Pat. No. 4,705,777; U.S. Pat. No. 4,659,692; U.S. Pat. No. 4,543,252), β-defensins (Selsted et al., 1993, *J. Biol. Chem.* 288:6641–6648; Diamond et al., 1991, *Proc. Natl. Acad. Sci. U.S.A.* 88:3952–3958), insect defensins (Lambert et al., 1989, *Proc. Natl. Acad. Sci. U.S.A.* 88:262–265; Matsuyama and Natori, 1988, *J. Biol. Chem.* 263:17112–17116), and protegrins (Kokryakov et al., 1993, *FEBS* 337:231–236; Zhao et al., 1994, *FEBS Letters* 346:285–288; Migorodskaya et al., 1993, *FEBS* 330:339–342; Storici et al., 1993, *Biochem. Biophys. Res. Commun.* 196:1363–1367; Zhao et al., 1994, *FEBS Lett.* 346:285–288; Manzoni et al., 1996, *FEBS Lett.* 383:93–98; U.S. Pat. No. 5,464,823). The discovery of these new classes of antimicrobial peptides offers hope that some might be developed into agents that can be used against microorganisms of medicinal importance. Those of animal origin are of particular importance, as these antimicrobial peptides generally exhibit activity against antibiotic-resistant bacterial strains and have a lower frequency of resistance as compared to conventional antibiotics (Steinberg et al., 1996, "Protegrins: Fast Acting Bactericidal Peptides," presented at: *Intl. Symposium on Staphylococci and Staphylococcus Infections*, Aix les Bains, France). At least one of these peptides, magainin MSI-78, is currently in Phase III clinical trials for infections associated with diabetic foot ulcers (Craig, Aug. 17, 1995, *BioWorld Today* 6(158):1).

The use of peptides as therapeutic agents in general, however, has not been completely satisfactory. Peptides composed of L-amino acids undergo rapid proteolysis in the gut, making oral administration, the method generally associated with the highest patient compliance, extremely difficult. Additionally, peptides degrade fairly rapidly in serum and therefore must be administered in large doses which often can cause numerous adverse side effects and serious toxicity. As peptides are expensive to manufacture, high dosage levels contribute significantly to the overall cost of peptide therapeutics. Furthermore, the flexibility of the peptide structure in solution is often associated with low biological activity and/or selectivity.

It has now been discovered that cyclic peptides related to the tachyplesin and protegrin classes of antimicrobial peptides exhibit broad spectrum antimicrobial activity typically associated with these classes of peptides while overcoming many of the disadvantages of peptide therapeutics discussed above. Thus, the cyclic peptides are ideally suited for use as antimicrobial therapeutic agents. For example, cyclic peptides are more resistant to proteolytic degradation and therefore have a greater potential for oral administration and/or lower dosage levels than non-cyclized peptides. Cyclization also confers structural stability without interfering with the side chains necessary for bioactivity, potentially leading to greater efficacy.

Cyclic analogues of the various known classes of antimicrobial peptides have not been reported in the literature. The only cyclic antibiotic peptide described in the literature are gramicidin-S (Tamaki et al., 1995, *Int. J. Peptide Protein Res.* 45:299–302; Gause, 1994, *Lancet* 247:715; Battersby et al., 1951, *J. Am. Chem. Soc.* 73:1887; Schwyzen et al., 1957, *Helv. Chim. Acta* 40:624), grastatin (Zharikova et al., 1972, *Vestn. Mosk. Univ. Biol. Pochivoved* 27:110; Myaskovskaya et al., 1973, *Vestn. Mosk. Univ. Biol. Pochivoved* 28:123) and tyrocidines (Laiken et al., 1969, *J. Biol. Chem.* 244:4454; Gibbons et al., 1975, *Biochemistry* 14:420). Significantly, these cyclic peptides are known to be toxic and do not contain positively-charged amino acid residues in loop or turn regions of the molecules—a feature of the novel class of cyclic peptides described herein thought to be important for broad-spectrum antimicrobial activity and improved efficacy towards antibiotic-resistant microbes.

3. SUMMARY OF THE INVENTION

In one aspect, the present invention provides cyclic peptides having antimicrobial activity. The cyclic peptides of the invention are generally comprised of about 10–30 amino acid residues and may contain regions or segments of peptidomimetic moieties. The cyclic peptides are characterized by a structure containing three main elements or domains: an amphiphilic anti-parallel β-sheet region, a β-turn region and a loop region.

Each strand of the amphiphilic anti-parallel β-sheet region comprises about 3 to 11 amino acid residues, with each strand having the same number of residues. The β-sheet is amphiphilic, i.e., one surface of the β-sheet has a net hydrophobic character and the other surface has a net hydrophilic character. The amphiphilic β-sheet region may optionally contain zero, one or two interstrand disulfide interlinkages.

The β-turn region reverses the direction of the polypeptide chain so as to allow a portion of the polypeptide chain to adopt an anti-parallel β-sheet secondary structure. Typically, the β-turn region comprises a four amino acid residue peptide segment. Preferably, the two internal amino acid residues of the β-turn are not involved in the hydrogen-bonding of the β-sheet; the two amino acid residues on either side of the internal residues are included in the hydrogen-bonding of the β-sheet. Alternatively, the β-turn region may comprise an organic molecule that mimics the structure of a peptide β-turn.

Like the β-turn region, the loop region links the anti-parallel strands comprising the β-sheet region. Typically, the loop region comprises a two to four amino acid residue reverse-turn such as a γ-turn or a β-turn. Alternatively, the loop region may comprise an organic molecule that mimics the structure of a peptide reverse-turn.

Lastly, the cyclic peptides of the invention are basic, i.e., they have a net positive charge at physiological pH. Typically, about 15% to 50% of the amino acid residues comprising the peptide are basic amino acid residues. At least one amino acid residue in the loop or β-turn region of the peptide is a basic amino acid residue.

Thus, in one illustrative embodiment the invention is directed to cyclic peptides having the formula:

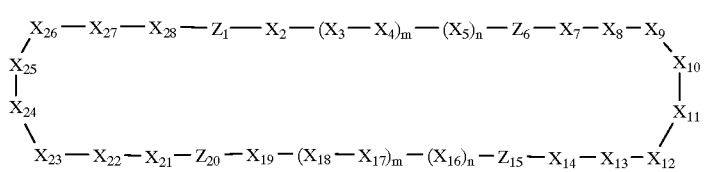

(I)

wherein m=0,1,2 and n=0,1 with the proviso that when m=2, n=0;

$X_{21}$, $X_{22}$, $X_{24}$, $X_{25}$, $X_{27}$ and $X_{28}$ are each independently present or absent;

$X_7$ and $X_{14}$ are either both present or both absent;

$X_8$ and $X_{13}$ are either both present or both absent;

$X_2, X_3, X_4, X_5, X_7, X_8, X_{13}, X_{14}, X_{16}, X_{17}, X_{18}, X_{19}, X_{21}, X_{22}, X_{27}$ and $X_{28}$ are each independently a hydrophobic amino acid, a hydrophilic amino acid or a small amino acid, with the provisos that (i) when $X_2$ is a hydrophobic amino acid $X_7, X_{14}, X_{19}, X_{21}$ and $X_{28}$ are each independently a hydrophobic amino acid or a small amino acid and $X_3, X_8, X_{13}, X_{18}, X_{22}$ and $X_{27}$ are each independently a hydrophilic amino acid or a small amino acid; and (ii) when $X_2$ is a hydrophilic amino acid $X_7, X_{14}, X_{19}, X_{21}$ and $X_{28}$ are each independently a hydrophilic amino acid or a small amino acid and $X_3, X_8, X_{13}, X_{18}, X_{22}$ and $X_{27}$ are each independently a hydrophobic amino acid or a small amino acid;

$X_{23}, X_{24}, X_{25}$ and $X_{26}$ taken together are a loop;

$Z_1, Z_6, Z_{15}$ and $Z_{20}$ are each independently a hydrophilic amino acid, a small amino acid or a cysteine-like amino acid;

$X_9, X_{10}, X_{11}$ and $X_{12}$ taken together are a β-turn;

at least one of $X_9, X_{10}, X_{11}, X_{12}, X_{23}, X_{24}, X_{25}$ or $X_{26}$ is a basic amino acid; and wherein the peptide has a net positive charge at physiological pH.

The cyclic peptides of the invention exhibit broad spectrum antimicrobial activity, being biocidal against a wide range of microbial targets, including gram-positive bacteria, gram-negative bacteria, yeast, fungi and protozoa. Accordingly, the peptides can be used as antimicrobial agents in a wide variety of applications. For example, the peptides can be used to preserve or disinfect a variety of materials, including medical equipment, foodstuffs, cosmetics, medicaments or other nutrient-containing materials. The peptides are also useful for prophylaxis or treatment of microbial infections or diseases related thereto in both plants and animals.

In another aspect, the present invention is directed to compositions comprising one or more of the above-described cyclic peptides and a carrier or excipient. Such compositions are biostatic or biocidal against a wide range of microbial targets.

In yet another aspect, the present invention is directed to methods of using the above-described cyclic peptides, or compositions thereof, to inhibit microbial growth. The method generally involves contacting a microbe with an antimicrobially effective amount of one or more of the cyclic peptides or compositions of the invention. In a preferred embodiment, a bacteria is contacted with a bactericidally effective amount of peptide or composition.

In a final aspect, the present invention is directed to methods of using the above-described cyclic peptides, or compositions thereof, to prevent or treat microbial infections or diseases related thereto in both plants and animals. The method generally involves administering to a plant or animal a therapeutically effective amount of one or more of the cyclic peptides or compositions of the invention. In a preferred embodiment, the cyclic peptides or compositions of the invention are used to treat or prevent systemic infections caused by multi-drug resistant pathogens such as vancomycin-resistant *Enterococcus faecium*, methicillin-resistant *Staphylococcus aureus* and penicillin-resistant *Streptococcus pneumoniae*.

4. BRIEF DESCRIPTION OF THE FIGURES

5. DETAILED DESCRIPTION OF THE INVENTION 5.1 Definitions

"Peptidomimetic Moiety:" As used herein, "peptidomimetic moiety" refers to an organic molecule that mimics the secondary structure of a polypeptide chain.

"Primary Structure:" As used herein, "primary structure" refers to the amino acid sequence of a polypeptide chain or the chemical formula of a peptidomimetic moiety.

"Secondary Structure:" As used herein, "secondary structure" refers to the regular local structure of segments of polypeptide chains including, but not limited to, helices such as α-helices, extended strands such as β-strands and sheets of extended strands such as β-sheets.

Figure 1:
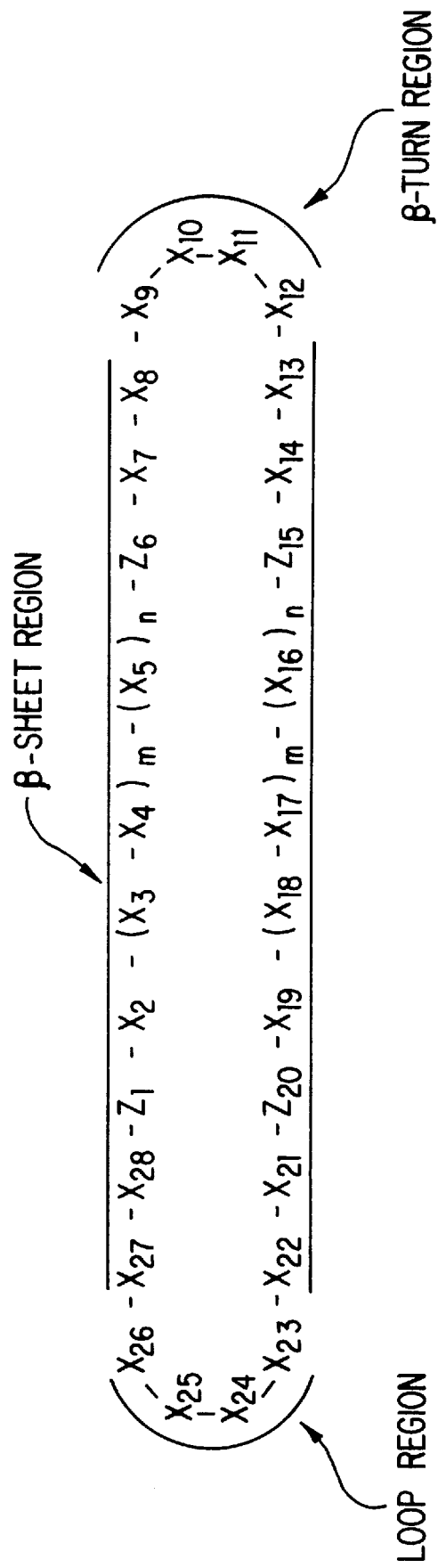
FIG. 1 is a cartoon illustrating the main structural elements of the peptides of the invention.
Figure 2:
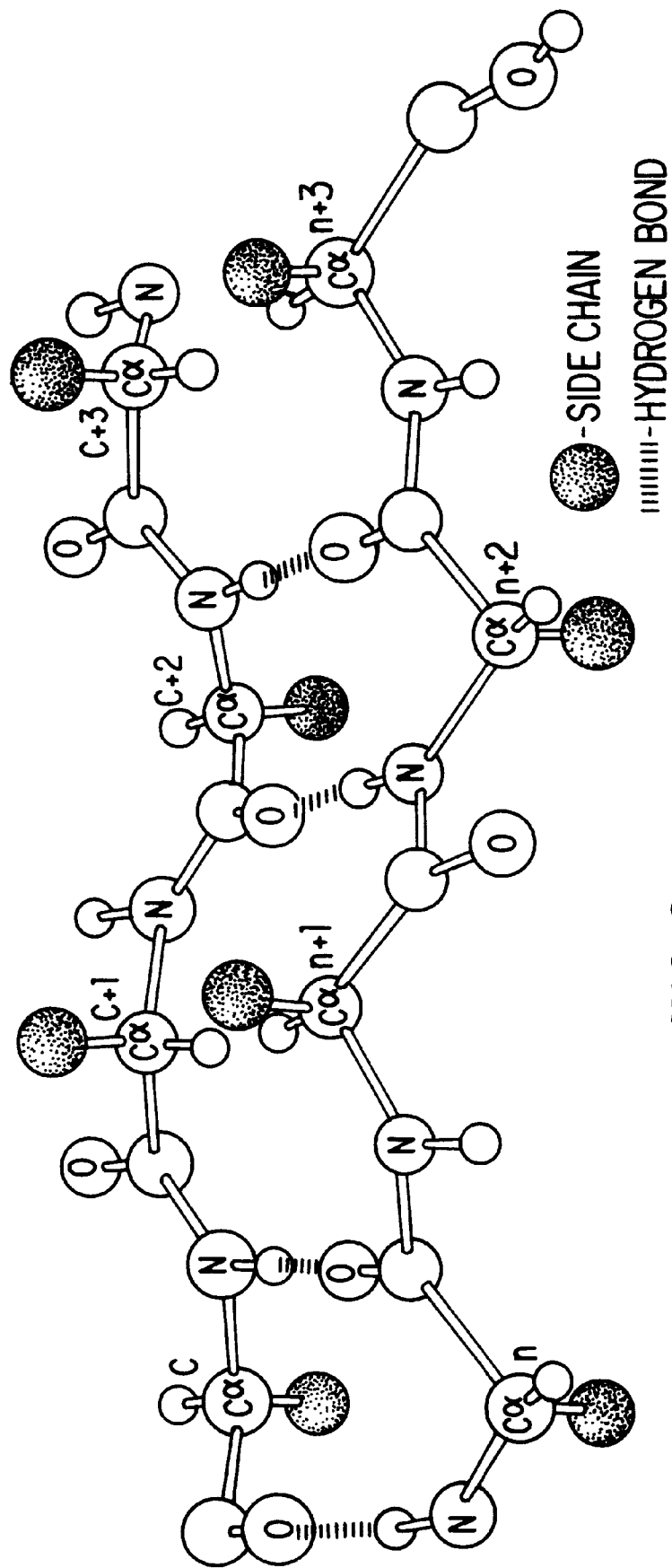
FIG. 2 is an illustration of a β-sheet secondary peptide structure.

"Anti-Parallel β-Sheet:" As used herein "anti-parallel β-sheet" refers to a secondary structure of a polypeptide chain characterized by intermolecular backbone-backbone hydrogen bonding between anti-parallel peptide strands (see, FIG. 2). According to the usage herein, an anti-parallel β-sheet may contain as few as six amino acid residues (three amino acid residues per strand), and may optionally contain interstrand disulfide linkages.

"Amphiphilic Anti-Parallel β-Sheet:" As used herein, "amphiphilic anti-parallel β-sheet" refers to an anti-parallel β-sheet wherein one surface has a net hydrophobic character and another surface has a net hydrophilic character. According to the usage herein, anti-parallel β-sheets having a pair of amino acid residues flanked by disulfide bridges are explicitly included in the definition of "amphiphilic anti-parallel β-sheet." Thus, sequences having the following formula are explicitly included in the definition of "amphiphilic anti-parallel β-sheet:"

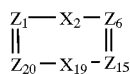

wherein $Z_1$, $Z_6$, $Z_{25}$ and $Z_{20}$ are each independently a cysteine-like amino acid; $X_2$ is a hydrophobic amino acid; $X_{19}$ is a hydrophobic or small amino acid; and ‖ is a disulfide linkage.

"Reverse-Turn:" As used herein, "reverse-turn" refers to a characteristic secondary structure that links adjacent strands of an anti-parallel β-sheet. Typically, a "reverse-turn" is a two to four amino acid residue peptide segment that reverses the direction of a polypeptide chain so as to allow a single polypeptide chain to adopt an anti-parallel β-sheet conformation. Such peptide segments are well known in the art and include, by way of example and not limitation, three amino acid residue γ-turns (Rose et al., 1985, *Adv. Protein Chem.* 37:1–109; Wilmer-White et al., 1987, *Trends Biochem. Sci.* 12:189–192; Wilmot et al., 1988, *J. Mol. Biol.* 203:221–232; Sibanda et al., 1989, *J. Mol. Biol.* 206:759–777; Tramontano et al., 1989, *Proteins: Struct. Funct. Genet.* 6:382–394) and four amino acid residue β-turns, as described below.

The term "reverse-turn" also includes peptidomimetic moieties that mimic the structures of peptide reverse-turns.

"Reverse-Turn Sequence:" As used herein, "reverse-turn sequence" refers to the primary structure of a reverse-turn. Thus, for a peptide reverse-turn, "reverse-turn sequence" refers to the primary structure of the reverse-turn peptide segment. For a peptidomimetic reverse-turn, "reverse-turn sequence" refers to the chemical formula of the reverse-turn peptidomimetic moiety.

"β-Turn:" As used herein, "β-turn" refers to a recognized sub-class of reverse-turns. Typically, a "β-turn" is a four amino acid residue peptide segment that reverses the direction of a polypeptide chain so as to allow a single polypeptide chain to adopt an anti-parallel β-sheet secondary structure. Generally, the two internal amino acid residues of the β-turn are not involved in the hydrogen-bonding of the β-sheet; the two amino acid residues on either side of the internal residues are included in the hydrogen-bonding of the β-sheet (see, FIG. 3). The term "β-turn" expressly includes all types of peptide β-turns commonly known in the art including, but not limited to, type-I, type-II, type-III, type-I', type-II' and type-III' β-turns (see, Rose et al., 1985, *Adv. Protein Chem.* 37:1–109; Wilmer-White et al., 1987, *Trends Biochem. Sci.* 12:189–192; Wilmot et al., 1988, *J. Mol. Biol.* 203:221–232; Sibanda et al., 1989, *J. Mol. Biol.* 206:759–777; Tramontano et al., 1989, *Proteins: Struct. Funct. Genet.* 6:382–394), as well as peptidomimetic β-turns, including, among other, those described in Giannis and Kolter, 1993, *Agnew. Chem. Intl. Ed. Eng.* 32:1244–1267; Kahn et al., 1988, *J. Molecular Recognition* 1:75–79; and Kahn and Chen, 1987, *Tetrahedron Lett.* 28:1623–1626).

"β-Turn Sequence:" As used herein, "β-turn sequence" refers to the primary structure of a β-turn. Thus, for a peptide β-turn, "β-turn sequence" refers to the primary structure of the peptide β-turn segment. For a peptidomimetic β-turn, "β-turn sequence" refers to the chemical formula of the β-turn peptidomimetic moiety.

"Antimicrobially Effective Amount:" As used herein, "antimicrobially effective amount" refers to an amount of cyclic peptide (or composition thereof) that is biostatic or biocidal against a target microbe. More specifically, an antimicrobially effective amount of peptide refers to an amount of peptide that inhibits the growth of, or is lethal to, a target microbe.

"Therapeutically Effective Amount" As used herein, "therapeutically effective amount" refers to an amount of cyclic peptide (or composition thereof) effective to ameliorate the symptoms of, or ameliorate, treat or prevent microbial infections or diseases related thereto in both plants and animals.

"Pharmaceutically Acceptable Salt:" As used herein, "pharmaceutically acceptable salt" refers to those salts which substantially retain the antimicrobial activity of the free bases and which are obtained by reaction with inorganic acids.

5.2 Detailed Description of the Preferred Embodiments

The present invention provides cyclic peptides having antimicrobial activity, compositions comprising the cyclic peptides, methods of using the cyclic peptides (or compositions thereof) to inhibit the growth of or kill a wide variety of microbial targets and methods of using the cyclic peptides (or compositions thereof) to treat or prevent microbial infections and diseases related thereto in both plants and animals.

The peptides of the invention exhibit broad spectrum antimicrobial activity, being biostatic or biocidal against a wide range of microbial targets, including but not limited to, Gram-negative bacteria such as *Escherichia coli*, *Pseudomonas aeruginosa, Klebsiella ssp.*, and *Hemophilus influenza*; Gram-positive bacteria such as *Enterococcus faecium, Staphylococcus aureus*, the viridans group of streptococci including *Streptococcus salivarius* and *Streptococcus mitis; Streptococcus pneumonia*; and yeast such as *Candida albicans, Candida glabrata* and *Candida krusei*. Significantly, the cyclic peptides described herein are biostatic or biocidal against clinically relevant pathogens exhibiting multi-drug resistance such as, among others, vancomycin-resistant *Enterococcus faecium* ("VRE"), penicillin-resistant *Streptococcus pneumoniae* ("PRSP") and methicillin-resistant *Staphylococcus aureus* ("MRSA").

The cyclic peptides of the invention (or compositions thereof) are useful as biocidal or biostatic agents in a wide variety of applications. For example, the peptides can be used to disinfect or preserve a variety of materials including medical instruments, foodstuffs, medicaments, cosmetics and other nutrient-containing materials. The cyclic peptides of the invention are particularly useful as bacteriostatic or bactericidal agents against multi-drug-resistant pathogens such as VRE and MRSA in a variety of clinical settings.

The cyclic peptides, or compositions thereof, are also useful for the prophylaxis or treatment of microbial infections and diseases related thereto in both plants and animals. Such diseases include, but are not limited to, Gram-negative and Gram-positive bacterial infections, endocarditis, pneumonia and other respiratory infections, urinary tract infections, systemic candidiasis, oral mucositis, etc.

The peptides described herein provide significant advantages over traditional antibiotics and/or non-cyclized antimicrobial peptides. For example, as the cyclic peptides described herein are related to antimicrobial peptides found naturally in plants, insects and animals, it is believed that the relatively high frequency of resistance observed for traditional antibiotics will not be observed for the cyclic peptides described herein. Additionally, the cyclic peptides described herein are more resistant to proteolytic cleavage and therefore have a longer serum and/or gut half-life than non-cyclized antimicrobial peptides, thereby providing greater potential for oral administration and lower dosage levels. Lastly, cyclization confers structural stability to the peptide, oftentimes leading to improved efficacy and concomitant lower therapeutic costs as compared to non-cyclized analogues.

5.2.1 The Peptides

Generally, the cyclic peptides of the invention have the formula:

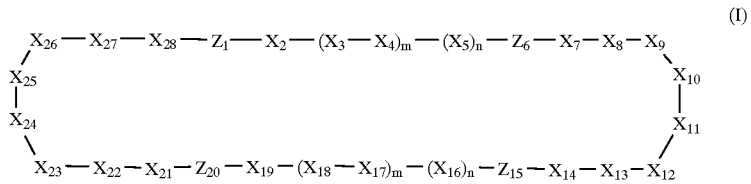

(I)

The designation $X_n$ in each case represents an amino acid at the specified position in the peptide. Similarly, the designation $Z_n$ represents an amino acid at the specified position and further represents those positions in the peptide which may optionally contain amino acid residues capable of forming disulfide interlinkages.

As will be discussed in more detail below, certain residues $X_n$, $X_{n+1}$, etc. taken together comprise specified secondary structures. Some of these structures can be obtained with organic molecules that mimic the peptide secondary structure ("peptidomimetic moieties"). In these cases, the specified designations $X_n$, $X_{n+1}$, etc. may also refer, when taken together, to the peptidomimetic moieties.

As the peptides of the invention are cyclic and therefore do not have amino or carboxy termini, it is to be understood that the relative positions of $X_n$ and $Z_n$ in the peptides of formula I have been arbitrarily assigned for purposes of illustration and discussion only. The specified positions do not carry independent significance.

The amino acid residues denoted by $X_n$ or $Z_n$ may be the genetically encoded L-amino acids, naturally occurring non-genetically encoded L-amino acids, synthetic L-amino acids or D-enantiomers of all of the above. The amino acid notations used herein for the twenty genetically encoded L-amino acids and common non-encoded amino acids are conventional and are as follows:

| Amino Acid | One-Letter Symbol | Common Abbreviation |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-alanine | | bAla |
| 2,3-diaminopropionic acid | | Dpr |
| α-aminoisobutyric acid | | Aib |
| N-methylglycine | | MeGly |

-continued

| Amino Acid | One-Letter Symbol | Common Abbreviation |
| --- | --- | --- |
| (sarcosine) | | |
| Ornithine | O | Orn |
| Citrulline | | Cit |
| t-butylalanine | | t-BuA |
| t-butylglycine | | t-BuG |
| N-methylisoleucine | | MeIle |
| phenylglycine | | Phg |
| cyclohexylalanine | | Cha |
| Norleucine | | Nle |
| 2-naphthylalanine | | 2-Nal |
| 4-chlorophenylalanine | | Phe(4-Cl) |
| 2-fluorophenylalanine | | Phe(2-F) |
| 3-fluorophenylalanine | | Phe(3-F) |
| 4-fluorophenylalanine | | Phe(4-F) |
| Penicillamine | | Pen |
| 1,2,3,4-tetrahydro-isoquinoline-3-carboxylic acid | | TiC |
| β-2-thienylalanine | | Thi |
| Methionine sulfoxide | | MSO |
| Homoarginine | | hArg |
| N-acetyl lysine | | AcLys |
| 2,4-diamino butyric acid | | $A_2BU$ |
| p-aminophenylalanine | | Phe(pNH$_2$) |
| N-methylvaline | | MeVal |
| Homocysteine | | hCys |
| Homoserine | | hser |
| ε-amino hexanoic acid | | Aha |

| Amino Acid | One-Letter Symbol | Common Abbreviation |
|---|---|---|
| δ-amino valeric acid | | Ava |
| 2,3-diaminobutyric acid | | DBU |

The cyclic peptides described herein are partially defined in terms of amino acid residues of designated classes. The amino acids are generally categorized into three main classes, hydrophilic amino acids, hydrophobic amino acids, and small amino acids, depending primarily on the characteristics of the amino acid side chain. These main classes are further divided into subclasses. Hydrophilic amino acids include amino acids having acidic, basic or polar side chains and hydrophobic amino acids include amino acids having aromatic or apolar side chains. As will be discussed more thoroughly below, the class of small amino acids includes amino acids having either polar or apolar side chains, but wherein the side chain does not contribute significantly to the net properties of the peptide. The definitions of the classes of amino acids as used herein are as follows:

"Hydrophobic Amino Acid" refers to an amino acid having a side chain that is uncharged at physiological pH and that is repelled by aqueous solution so as to seek the inner positions in the conformation of a peptide in which it is contained when the peptide is in aqueous medium.

"Aromatic Amino Acid" refers to a hydrophobic amino acid having a side chain containing at least one ring having a conjugated π-electron system (aromatic group). Genetically encoded aromatic amino acids include phenylalanine, tyrosine and tryptophan. Non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Apolar Amino Acid" refers to a hydrophobic amino acid having a side chain that is uncharged at physiological pH. Genetically encoded apolar amino acids include leucine, valine, isoleucine and methionine. Non-genetically encoded apolar amino acids include t-butylalanine, t-butylglycine, N-methylisoleucine, norleucine, N-methyl valine and cyclohexylalanine.

"Hydrophilic Amino Acid" refers to an amino acid having a side chain that is attracted by aqueous solution so as to seek the surface positions in the conformation of a peptide in which it is contained when the peptide is in aqueous medium at physiological pH.

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Genetically encoded basic amino acids include the non-cyclic amino acids arginine and lysine and the cyclic amino acid histidine. Non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but that is not sufficiently repelled by aqueous solutions so as to seek inner positions in the conformation of a peptide in which it is contanioed when the peptide is in aqueous medium. Genetically encoded polar amino acids include asparagine and glutamine. Non-genetically encoded polar amino acids include citrulline, N-acetyl lysine and methionine sulfoxide.

"Small Amino Acid" refers to an amino acid having a side chain which is not sufficiently large to confer significant hydrophobicity or hydrophilicity to the peptide. Small amino acids are those with side chains having four or fewer carbons when the side chain contains at least one polar group, and three or fewer carbons when the side chain does not contain a polar group. Genetically encoded small amino acids include glycine, serine, alanine and threonine. The gene-encoded secondary imino acid proline is also designated as a small amino acid, although it is known to affect the secondary conformation of peptide chains. Non-genetically encoded small amino acids include β-alanine, N-methyl glycine (sarcosine) and α-aminoisobutyric acid.

"Cysteine-Like Amino Acid" refers to an amino acid having a side chain capable of participating in a disulfide linkage. Thus, cysteine-like amino acids generally have a side chain containing at least one thiol (SH) group. Genetically encoded cysteine-like amino acids include cysteine. Non-genetically encoded cysteine-like amino acids include homocysteine and penicillamine.

As will be appreciated by those having skill in the art, the degree of attraction or repulsion required for classification as polar, apolar or small is somewhat arbitrary. For example, while both serine and threonine contain polar hydroxyl groups these residues are classified as small amino acids, as their side chains do not confer significant overall hydrophilicity to the peptides of the invention. Amino acids not specifically named herein can be readily classified into the above-defined categories on the basis of known behavior as compared with amino acids specifically identified.

Certain commonly encountered amino acids which are not genetically encoded of which the peptides of the invention may be composed include, but are not limited to, β-alanine (b-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (DBU); 2,3-diaminobutyric acid (A₂BU); p-aminophenylalanine (Phe(pNH₂)); N-methyl valine (MeVal); homocysteine (hCys) and homoserine (hSer). These amino acids also fall conveniently into the categories defined above.

The classifications of the above-described genetically encoded and non-encoded amino acids are summarized in Table 1, below. It is to be understood that Table 1 is for illustrative purposes only and does not purport to be an exhaustive list of amino acid residues that may comprise the cyclic peptides described herein.

TABLE 1

| Classification | Genetically Encoded | Non-Genetically Encoded |
| --- | --- | --- |
| Hydrophobic | | |
| Aromatic | F, Y, W | Phg, Nal, Thi, Tic, Phe(4-Cl), Phe(2-F), Phe(3-F), Phe(4-F) |
| Apolar | L, V, I, M | t-BuA, t-BuG, MeIle, Nle, MeVal, Cha |
| Hydrophilic | | |
| Acidic | D, E | |
| Basic | H, K, R | Dpr, Orn, hArg, Phe(p-NH$_2$), DBU, A$_2$BU |
| Polar | Q, N | Cit, AcLys, MSO |
| Small | S, T, G, A, P | bAla, MeGly, Aib, hSer |
| Cysteine-Like | C | Pen, hCys |

In the peptides of formula I, the symbol "—" between amino acid residues $A_n$ and/or $Z_n$ generally designates a backbone interlinkage. Thus, the symbol "—" usually designates an amide linkage (—C(O)—NH). It is to be understood, however, that in all of the cyclic peptides of the invention one or more amide linkages may optionally be replaced with a linkage other than amide. Such linkages include, but are not limited to, —CH$_2$NH—, —CH$_2$S—, —CH$_2$CH$_2$, —CH=CH— (cis and trans), —C(O)CH$_2$—, —CH(OH)CH$_2$— and —CH$_2$SO—.

Peptides having such linkages and methods for preparing such peptides are well-known in the art (see, e.g., Spatola, 1983, *Vega Data* 1(3) (general review); Spatola, 1983, "Peptide Backbone Modifications" In: *Chemistry and Biochemistry of Amino Acids Peptides and Proteins* (Weinstein, ed.), Marcel Dekker, New York, p. 267 (general review); Morley, 1980, *Trends Pharm. Sci.* 1:463–468; Hudson et al., 1979, *Int. J. Prot. Res.* 14:177–185 (—CH$_2$NH—, —CH$_2$CH$_2$—); Spatola et al., 1986, *Life Sci.* 38:1243–1249 (—CH$_2$—S); Hann, 1982, *J. Chem. Soc. Perkin Trans. I.* 1:307–314 (—CH=CH—, cis and trans); Almquist et al., 1980, *J. Med. Chem.* 23:1392–1398 (—COCH$_2$—); Jennings-White et al., *Tetrahedron. Lett.* 23:2533 (—COCH$_2$—); European Patent Application EP 45665 (1982) CA:97:39405 (—CH(OH)CH$_2$—); Holladay et al., 1983, *Tetrahedron Lett.* 24:4401–4404 (—C(OH)CH$_2$—); and Hruby, 1982, *Life Sci.* 31:189–199 (—CH$_2$—S—).

As will be discussed in more detail below, in the loop region of the peptide the interlinkage designated by "—" may also be a linker. Typically, a linker is a bifunctional molecule that spaces one amino acid residue from another amino acid residue in the peptide. Such linkers, which may be flexible, semi-rigid or rigid, are well-known in the art and include polypeptides such as poly-Gly and poly-Pro, bifunctional hydrocarbons such as aminocaproic acid, δ-aminovaleric acid and β-alanine, carbohydrates, nucleic acids, and the like.

Generally, the cyclic peptides of the invention are comprised of about 10 to 30 amino acid residues. As will be described in more detail below, certain amino acids or segments of amino acids may optionally be replaced by peptidomimetic moieties. The cyclic peptides are characterized by three main structural elements or domains: an amphiphilic anti-parallel β-sheet region, a β-turn region and a loop region. Referring to FIG. 2, the amphiphilic anti-parallel β-sheet region comprises anti-parallel N- and C-strands non-covalently linked together via backbone-backbone hydrogen-bonds. Typically, alternating amino acid residues on each strand participate in interstrand hydrogen-bonds (for a detailed description of the structure of β-sheets the reader is referred to Creighton, 1993, *Proteins: Structures and Molecular Properties*, W. H. Freeman and Company, New York, and references cited therein). In the peptides of formula I, amino acid residues $X_{27}$-$X_{28}$-$Z_1$-$X_2$-$(X_3$-$X_4)_m$-$(X_5)_n$-$Z_6$-$X_7$-$X_8$ comprise the N-strand and residues $X_{22}$-$X_{21}$-$Z_{20}$-$X_{19}$-$(X_{18}$-$X_{17})_m$-$(X_{16})_n$-$Z_{15}$-$X_{14}$-$X_{13}$ comprise the C-strand. Each strand is composed of about 3 to 11 amino acids residues, with each strand having the same number of residues. As will be discussed in more detail below, the N- and C-strands may optionally be covalently linked via one or two disulfide bridges.

The β-sheet region of the cyclic peptides described herein is generally amphiphilic, i.e., one surface of the β-sheet has a net hydrophobic character and the other surface has a net hydrophilic character. Referring to the β-sheet structure illustrated in FIG. 2, the side chains of L-amino acid residues adjacent to one another intrastrand-wise (residues n, n+1, n+2, etc.) point in opposite directions so as to be positioned on opposite surfaces of the β-sheet. The side chains of L-amino acid residues adjacent to one another interstrand-wise (residues n and c, n+1 and c+1, etc.) point in the same direction so as to be positioned on the same surface of the β-sheet. Using this general structural motif an amphiphilic anti-parallel β-sheet is obtained by selecting amino acids at each residue position so as to yield a β-sheet having hydrophobic side chains positioned on one surface of the sheet and hydrophilic side chains positioned on the other.

Of course, it will be appreciated that as the surfaces of the amphiphilic anti-parallel β-sheet region need only have net hydrophobic or net hydrophilic character, each side chain comprising a particular surface need not be hydrophobic or hydrophilic. The surfaces may contain side chains that do not significantly alter the net character of the surface. For example, both the hydrophobic and hydrophilic surfaces may contain small amino acid side chains, as these side chains do not significantly contribute to the net character of the surface.

In the peptides of formula I the amphiphilic anti-parallel β-sheet region preferably has a characteristic pattern of alternating hydrophobic and hydrophilic amino acids, such that when $X_2$ is a hydrophobic amino acid $X_7$, $X_{14}$, $X_{19}$, $X_{21}$ and $X_{28}$ are each independently a hydrophobic amino acid or a small amino acid and $X_3$, $X_8$, $X_{13}$, $X_{18}$, $X_{22}$ and $X_{27}$ are each independently a hydrophilic amino acid or a small amino acid and when $X_2$ is a hydrophilic amino acid $X_7$, $X_{14}$, $X_{19}$, $X_{21}$ and $X_{28}$ are each independently a hydrophilic amino acid or a small amino acid and $X_3$, $X_8$, $X_{13}$, $X_{18}$, $X_{22}$ and $X_{27}$ are each independently a hydrophobic amino acid or a small amino acid. $Z_1$, $Z_6$, $Z_{15}$ and $Z_{20}$ are each independently a hydrophilic amino acid, a small amino acid or a cysteine-like amino acid. Using this general structural motif one having ordinary skill in the art can easily select amino acid residues within the above-described classifications to obtain an amphiphilic anti-parallel β-sheet region as defined herein.

The β-sheet secondary structure illustrated in FIG. 2 is composed entirely of L-amino acids. Those having skill in the art will recognize that substituting an L-amino acid with its corresponding D-enantiomer at a specific residue position may disrupt the structural stability or amphiphilicity of amphiphilic anti-parallel β-sheet region. The degree to which any particular enantiomeric substitution disrupts the structural stability or amphiphilicity depends, in part, on the size of the amino acid side chain and position of the residue within the β-sheet. Preferably, the β-sheet region of the peptides of formula I will contain mixtures of L- and D-amino acids that do not significantly affect the stability or amphiphilicity of the β-sheet region as compared to peptides containing the corresponding all D- or all L-enantiomeric forms of the sheet. Enantiomeric substitutions that do not substantially affect the stability or amphiphilicity of the β-sheet region will be readily apparent to those having skill in the art.

In a preferred embodiment of the invention, hydrophobic, hydrophilic and cysteine-like amino acids comprising the β-sheet region are either all L-enantiomers or all D-enantiomers. Small amino acids comprising the β-sheet region may be either L-enantiomers or D-enantiomers.

The β-sheet region of the cyclic peptides of formula I may contain from one to four cysteine-like amino acids. Preferably, when present, cysteine-like amino acids occur in pairs and participate in disulfide linkages or bridges. Accordingly, the cyclic peptides of formula I may be mono-cyclic, bi-cyclic or tri-cyclic. Tri-cyclic peptides of the invention contain two disulfide linkages, bi-cyclic peptides contain one disulfide linkage and mono-cyclic peptides contain no disulfide linkages. While the tri- and bi-cyclic peptides of the invention include all possible permutations of disulfide bond formation, it is preferred that, when present, disulfide linkages are formed between residues $Z_1$ and $Z_{20}$ and/or residues $Z_6$ and $Z_{15}$, respectively.

The sulfur atoms involved in an interstrand disulfide bridge in a β-sheet are not positioned within the plane defined by the interstrand backbone-backbone hydrogen-bonds; the sulfur atoms are at an angle with respect to the β-carbons of the bridged amino acid residues so as to be positioned on a surface of the β-sheet. Thus, the sulfur atoms of the disulfide linkages contribute to the net hydrophilicity of a surface of the β-sheet. It is to be understood that in the peptides of formula I a β-sheet region defined by the following formula is specifically contemplated to fall within the definition of amphiphilic anti-parallel sheet as described herein:

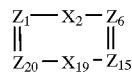

wherein $Z_1$, $Z_6$, $Z_{25}$ and $Z_{20}$ are each independently a cysteine-like amino acid; $X_2$ is a hydrophobic amino acid; $X_{19}$ is a hydrophobic or a small amino acid; and ‖ is a disulfide linkage.

The β-turn region of the peptides of formula I (residues $X_9$-$X_{10}$-$X_{11}$-$X_{12}$ taken together) links the strands of the amphiphilic anti-parallel β-sheet. The β-turn region may comprise a peptide β-turn or a peptidomimetic β-turn. Thus, the β-turn region comprises a peptide or peptidomimetic structure that reverses the direction of the polypeptide chain so as to allow a region of the peptide to adopt an anti-parallel β-sheet secondary structure.

Figure 3:
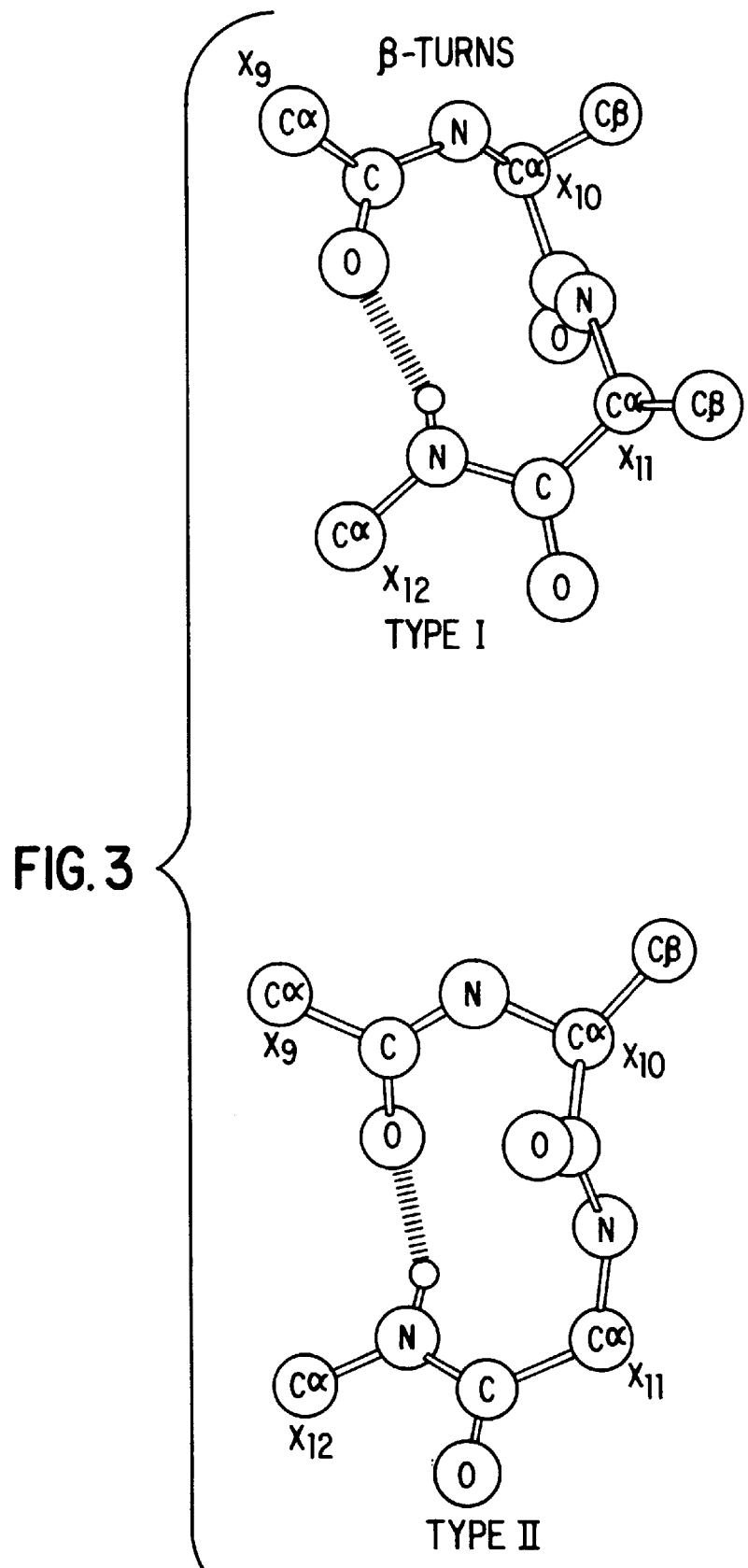
FIG. 3 is an illustration of exemplary peptide β-turn structures.

When the β-turn region is a peptide β-turn, the β-turn region may comprise any four amino acid residue peptide segment known to adopt a β-turn secondary structure in proteins or peptides. In such structures, the two internal amino acid residues of the turn are usually not involved in the hydrogen-bonding of the anti-parallel β-sheet; the two amino acid residues on either side of the internal residues are usually included in the hydrogen-bonding of the β-sheet. Referring to FIG. 3, wherein the four amino acid residue positions of the illustrated exemplary peptide β-turns are designated $X_9$ to $X_{12}$, it can be seen that residues $X_{10}$ and $X_{11}$ are not involved in the hydrogen-bonding of the β-sheet whereas residues $X_9$ and $X_{12}$ are.

The conformations and sequences of many peptide β-turns have been well-described in the art and include, by way of example and not limitation, type-I, type-I', type-II, type-II', type-III, type-III', type-IV, type-V, type-V', type-VIa, type-VIb, type-VII and type-VIII (see, Richardson, 1981, Adv. Protein Chem. 34:167–339; Rose et al., 1985, Adv. Protein Chem. 37:1–109; Wilmot et al., 1988, J. Mol. Biol. 203:221–232; Sibanda et al., 1989, J. Mol. Biol. 206:759–777; Tramontano et al., 1989, Proteins: Struct. Funct. Genet. 6:382–394). All of these types of peptide β-turn structures and their corresponding sequences, as well as later discovered peptide β-turn structures and sequences, are specifically contemplated by the invention.

The specific conformations of short peptide turns such as β-turns depend primarily on the positions of certain amino acid residues in the turn (usually Gly, Asn or Pro). Generally, the type-I β-turn is compatible with any amino acid residue at positions $X_9$ through $X_{12}$, except that Pro cannot occur at position $X_{11}$. Gly predominates at position $X_{12}$ and Pro predominates at position $X_{10}$ of both type-I and type-II turns. Asp, Asn, Ser and Cys residues frequently occur at position $X_9$, where their side chains often hydrogen-bond to the NH of residue $X_{11}$.

In type-II turns, Gly and Asn occur most frequently at position $X_{11}$, as they adopt the required backbone angles most easily. Ideally, type-I' turns have Gly at positions $X_{10}$ and $X_{11}$, and type-II' turns have Gly at position $X_{10}$. Type-III turns generally can have most amino acid residues, but type-III' turns usually require Gly at positions $X_{10}$ and $X_{11}$. Type-VIa and VIb turns generally have a cis peptide bond and Pro as an internal residue. For a review of the different types and sequences of β-turns in proteins and peptides the reader is referred to Wilmot et al., 1988, J. Mol. Biol. 203:221–232.

Preferred peptide β-turn sequences of the invention include those typically found in the defensin and β-defensin classes of peptides. Such peptide β-turn sequences include, but are not limited to, the following (sequences are listed in the order $X_9$-$X_{10}$-$X_{11}$-$X_{12}$):

| | |
|---|---|
| ARTE | (SEQ ID NO: 1) |
| GFRE | (SEQ ID NO: 2) |
| GNRG | (SEQ ID NO: 3) |
| LPRE | (SEQ ID NO: 4) |
| RFGE | (SEQ ID NO: 5) |
| SYRE | (SEQ ID NO: 6) |
| AFLK | (SEQ ID NO: 7) |
| AGIR | (SEQ ID NO: 8) |
| APRV | (SEQ ID NO: 9) |
| FQNR | (SEQ ID NO: 10) |
| GFRS | (SEQ ID NO: 11) |
| HFGG | (SEQ ID NO: 12) |
| IFGR | (SEQ ID NO: 13) |
| IGGR | (SEQ ID NO: 14) |
| IPIR | (SEQ ID NO: 15) |
| IRGV | (SEQ ID NO: 16) |
| ISGR | (SEQ ID NO: 17) |
| IWGR | (SEQ ID NO: 18) |
| LWGR | (SEQ ID NO: 19) |
| RFPY | (SEQ ID NO: 20) |
| RFYL | (SEQ ID NO: 21) |
| RGFL | (SEQ ID NO: 22) |
| RGGI | (SEQ ID NO: 23) |
| RGWI | (SEQ ID NO: 24) |
| RGWV | (SEQ ID NO: 25) |
| RIGA | (SEQ ID NO: 26) |
| RIPA | (SEQ ID NO: 27) |
| RIPI | (SEQ ID NO: 28) |
| RIPV | (SEQ ID NO: 29) |
| RLVF | (SEQ ID NO: 30) |
| RTSS | (SEQ ID NO: 31) |

| | |
|---|---|
| TTRT | (SEQ ID NO: 32) |
| VPIR | (SEQ ID NO: 33) |
| VWGR | (SEQ ID NO: 34) |
| GPRI | (SEQ ID NO: 35) |
| GPRV | (SEQ ID NO: 36) |
| GRAV | (SEQ ID NO: 37) |
| GRPV | (SEQ ID NO: 38) |
| INRG | (SEQ ID NO: 39) |
| LLNR | (SEQ ID NO: 40) |
| LNGR | (SEQ ID NO: 41) |
| LPNR | (SEQ ID NO: 42) |
| RNGG | (SEQ ID NO: 43) |
| RNPL | (SEQ ID NO: 44) |
| YQGR | (SEQ ID NO: 45) |
| FQHR | (SEQ ID NO: 46) |
| KGRE | (SEQ ID NO: 47) |
| RARG | (SEQ ID NO: 48) |
| RRTE | (SEQ ID NO: 49) |
| IRGR | (SEQ ID NO: 50) |
| KGHL | (SEQ ID NO: 51) |
| RFHL | (SEQ ID NO: 52) |
| RKSG | (SEQ ID NO: 53) |
| RPRV | (SEQ ID NO: 54) |
| RRAL | (SEQ ID NO: 55) |
| RRFS | (SEQ ID NO: 56) |
| RRGS | (SEQ ID NO: 57) |
| RSRG | (SEQ ID NO: 58) |
| RSTR | (SEQ ID NO: 59) |
| RTGR | (SEQ ID NO: 60) |
| RTRG | (SEQ ID NO: 61) |
| YRGR | (SEQ ID NO: 62) |
| RKNG | (SEQ ID NO: 63) |
| RNKG | (SEQ ID NO: 64) |
| KRRE | (SEQ ID NO: 65) |
| RKRG | (SEQ ID NO: 66) |
| RRRF | (SEQ ID NO: 67) |
| RRTR | (SEQ ID NO: 68) |

Figure 4:
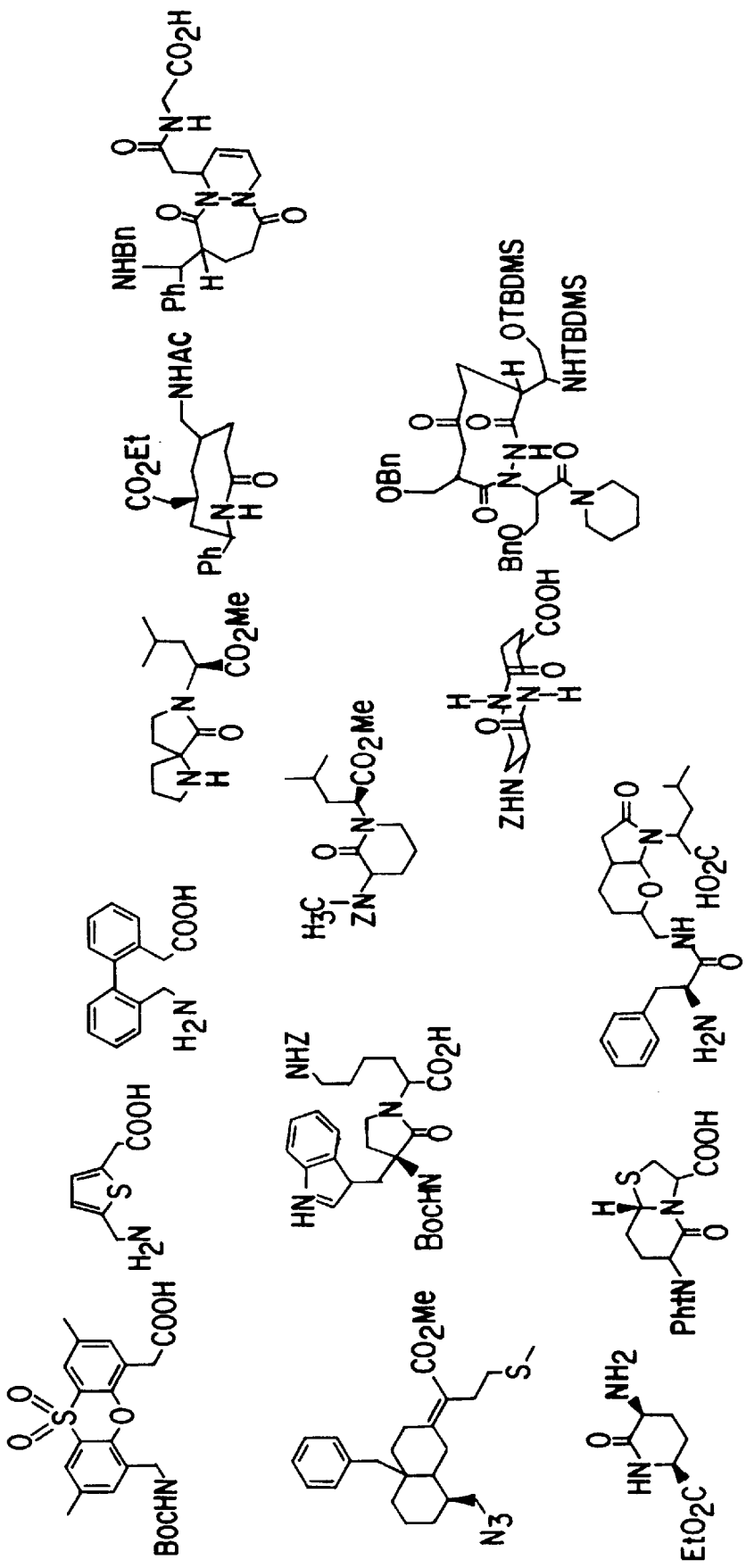
FIG. 4 is an illustration of exemplary peptidomimetic β-turn structures.

Alternatively, the β-turn region may comprise an organic molecule or moiety that mimics the structure of a peptide β-turn. Such β-turn peptidomimetic moieties, as well as methods for synthesizing peptides containing such moieties, are well known in art, and include, among others, those described in Giannis and Kolter, 1993, *Agnew. Chem. Intl. Ed. Eng.* 32:1244–1267; Kahn et al., 1988, *J. Molecular Recognition* 1:75–79; and Kahn et al., 1987, *Tetrahedron Lett.* 28:1623–1626. Exemplary peptidomimetic β-turn moieties are illustrated in FIG. 4.

Like the β-turn region, the loop region of the peptides of formula I (residues $X_{23}$-$X_{24}$-$X_{25}$-$X_{26}$ taken together) connects the anti-parallel strands of the anti-parallel β-sheet region. The loop region may be comprised of amino acids or peptidomimetic moieties.

Typically, the loop region comprises a peptide segment that is two, three or four amino acid residues in length (residues $X_{24}$ and $X_{25}$ are each independently present or absent). Each amino acid residue $X_{23}$, $X_{24}$, $X_{25}$ and $X_{26}$ is independently a hydrophilic, a hydrophobic or a small amino acid. Preferably, the loop region comprises a two, three or four amino acid residue reverse-turn sequence. Such reverse-turns are well-known in the art and include, by way of example and not limitation, three amino acid residue γ-turns (Rose et al., 1985, *Adv. Protein Chem.* 37:1–109; Wilmer-White et al., 1987, *Trends Biochem. Sci.* 12:189–192; Wilmot et al., 1988, *J. Mol. Biol.* 203:221–232; Sibanda et al., 1989, *J. Mol. Biol.* 206:759–777; Tramontano et al., 1989, *Proteins: Struct. Funct. Genet.* 6:382–394) and four amino acid residue β-turns, as described above.

In addition to the β-turn sequences listed above (SEQ ID NOS: 1–68), preferred amino acid sequences for the loop region of the peptides of the invention include, but are not limited to the following (listed in the order $X_{23}$-$X_{24}$-$X_{25}$-$X_{26}$):

| | |
|---|---|
| GFGE | (SEQ ID NO: 70) |
| GSGE | (SEQ ID NO: 71) |
| IAGE | (SEQ ID NO: 72) |
| LPLE | (SEQ ID NO: 73) |
| PWSE | (SEQ ID NO: 74) |
| VSGE | (SEQ ID NO: 75) |
| YSTE | (SEQ ID NO: 76) |
| IGGV | (SEQ ID NO: 77) |
| IPIS | (SEQ ID NO: 78) |
| IWGV | (SEQ ID NO: 79) |
| VWGA | (SEQ ID NO: 80) |
| VWGI | (SEQ ID NO: 81) |
| VWGV | (SEQ ID NO: 82) |
| INGV | (SEQ ID NO: 83) |
| TNGG | (SEQ ID NO: 84) |
| VNGA | (SEQ ID NO: 85) |
| VNGV | (SEQ ID NO: 86) |
| WNMG | (SEQ ID NO: 87) |
| GPQI | (SEQ ID NO: 88) |
| VPW | (SEQ ID NO: 89) |
| VGW | (SEQ ID NO: 90) |
| LPF | (SEQ ID NO: 91) |
| RGW | (SEQ ID NO: 92) |
| WAL | (SEQ ID NO: 93) |
| VRW | (SEQ ID NO: 94) |
| VRL | (SEQ ID NO: 95) |

Alternatively, the loop region may comprise peptidomimetic moieties that mimic the structures of reverse-turns. Such peptidomimetics include, e.g., structures that mimic peptide β-turns, as previously described.

As previously mentioned, in the loop region of the peptides of formula I the designation "—" may represent, in addition to a backbone interlinkage, a linker. Such linkers may be useful in situations where amino acid residues comprising the loop region are under significant conformational strain when connected via an amide bond or where they are relatively far apart, such as when residues $X_{24}$ and/or $X_{25}$ are absent. When present, preferred linkers are flexible bifunctional hydrocarbons and ethers such as $HO_2C$—$(CH_2)_n$—X and $HO_2C$—$(CH_2$—$O$—$CH_2)_n$—X where X is $NH_2$, OH or SH and n is 3, 4 or 5. Other suitable linkers and methods for synthesizing peptides containing such linkers will be apparent to those having skill in the art.

The cyclic peptides of the invention are generally basic, i.e., they have a net positive charge at physiological pH. It is understood that in a statistical collection of individual amino acid residues in a structure such as a peptide some of the amino acid residues will be positively charged, some negatively charged and some uncharged. Thus, some of the peptides will have a net charge and some not. To fit the definition of "basic," an excess of amino acids in the peptide molecule are positively charged at physiological pH. In preferred embodiments, at least about 15% to 50% of the amino acid residues comprising the peptides of formula I are basic amino acids.

While not intending to be bound by theory, it is believed that the presence of a positively charged amino acid residue in either the β-turn region or loop region of the molecule is important for antimicrobial activity. It is also believed that having a positively charged amino acid residue in either of these regions of the molecule provides the peptides with improved efficacy against antibiotic-resistant strains of bacteria. Thus, at least one amino acid residue in either the loop region or the β-turn region of the peptide is a basic amino acid residue. In preferred embodiments, both the β-turn region and the loop region contain at least one basic amino acid residue.

Of course, it is to be understood that in embodiments containing peptidomimetic moieties in both the β-turn and loop regions of the molecule, either or both of the peptidomimetic moieties will have a net positive charge at physiological pH.

Thus, in one illustrative embodiment, the peptides of formula I are defined as follows:

$$
\begin{array}{c}
X_{26} - X_{27} - X_{28} - Z_1 - X_2 - (X_3 - X_4)_m - (X_5)_n - Z_6 - X_7 - X_8 - X_9 \\
/ \qquad \qquad \qquad \qquad \qquad \qquad \qquad \qquad \qquad \qquad \qquad \qquad \qquad \quad \backslash \\
X_{25} \qquad \qquad \qquad \qquad \qquad \qquad \qquad \qquad \qquad \qquad \qquad \qquad \qquad \qquad X_{10} \\
| \qquad \qquad \qquad \qquad \qquad \qquad \qquad \qquad \qquad \qquad \qquad \qquad \qquad \qquad \quad | \\
X_{24} \qquad \qquad \qquad \qquad \qquad \qquad \qquad \qquad \qquad \qquad \qquad \qquad \qquad \qquad X_{11} \\
\backslash \qquad \qquad \qquad \qquad \qquad \qquad \qquad \qquad \qquad \qquad \qquad \qquad \qquad \qquad \quad / \\
X_{23} - X_{22} - X_{21} - Z_{20} - X_{19} - (X_{18} - X_{17})_m - (X_{16})_n - Z_{15} - X_{14} - X_{13} - X_{12}
\end{array}
\qquad (I)
$$

wherein m=0,1,2 and n=0,1 with the proviso that when m=2, n=0;

$X_{21}$, $X_{22}$, $X_{24}$, $X_{25}$, $X_{27}$ and $X_{28}$ are each independently present or absent;

$X_7$ and $X_{14}$ are either both present or both absent;

$X_8$ and $X_{13}$ are either both present or both absent;

$X_2$, $X_3$, $X_4$, $X_5$, $X_7$, $X_8$, $X_{13}$, $X_{14}$, $X_{16}$, $X_{17}$, $X_{18}$, $X_{19}$, $X_{21}$, $X_{22}$, $X_{27}$ and $X_{28}$ are each independently a hydrophobic amino acid, a hydrophilic amino acid or a small amino acid, with the provisos that (i) when $X_2$ is a hydrophobic amino acid $X_7$, $X_{14}$, $X_{19}$, $X_{21}$ and $X_{28}$ are each independently a hydrophobic amino acid or a small amino acid and $X_3$, $X_8$, $X_{13}$, $X_{18}$, $X_{22}$ and $X_{27}$ are each independently a hydrophilic amino acid or a small amino acid; and (ii) when $X_2$ is a hydrophilic amino acid $X_7$, $X_{14}$, $X_{19}$, $X_{21}$ and $X_{28}$ are each independently a hydrophilic amino acid or a small amino acid and $X_3$, $X_8$, $X_{13}$, $X_{18}$, $X_{22}$ and $X_{27}$ are each independently a hydrophobic amino acid or a small amino acid;

$X_{23}$, $X_{24}$, $X_{25}$ and $X_{26}$ taken together are a loop;

$Z_1$, $Z_6$, $Z_{15}$ and $Z_{20}$ are each independently a hydrophilic amino acid, a small amino acid or a cysteine-like amino acid;

$X_9$, $X_{10}$, $X_{11}$ and $X_{12}$ taken together are a β-turn;

at least one of $X_9$, $X_{10}$, $X_{11}$, $X_{12}$, $X_{23}$, $X_{24}$, $X_{25}$ or $X_{26}$ is a basic amino acid; and wherein the peptide has a net positive charge at physiological pH.

Preferred peptides of formula I are as follows:

| | |
|---|---|
| cyclo(SVRGFRVRGF) | (SEQ ID NO: 100) |
| cyclo(SVR*GFSVR*GF) | (SEQ ID NO: 101) |
| cyclo(FVRSYVLRSV) | (SEQ ID NO: 102) |
| cyclo(FVPRYVLPRV) | (SEQ ID NO: 103) |
| cyclo(YVRGFVFGRV) | (SEQ ID NO: 104) |
| cyclo(CVRRYCLWRGV) | (SEQ ID NO: 105) |
| cyclo (CVTRYCLWRGV) | (SEQ ID NO: 106) |
| cyclo(CVRTYCLRGW) | (SEQ ID NO: 107) |
| cyclo(CVPRYCLWRGV) | (SEQ ID NO: 108) |
| cyclo(CVRRYCLGRW) | (SEQ ID NO: 109) |
| cyclo(CVRRYCLGW) | (SEQ ID NO: 110) |
| cyclo(CVR*RYCLWRGW) | (SEQ ID NO: 111) |
| cyclo(CRRRFCYDLWRGV-Dpr-V) | (SEQ ID NO: 112) |
| cyclo(CV-Dpr-RPRFDYCLWRGV) | (SEQ ID NO: 113) |
| cyclo(CV-Dpr-RPRFDYCLPRW) | (SEQ ID NO: 114) |
| cyclo(Dpr-VDRPRF-Dpr-YDLWRGV) | (SEQ ID NO: 115) |
| cyclo(SVOGFSVOGF) | (SEQ ID NO: 116) |
| cyclo(FVGOYVLGOV) | (SEQ ID NO: 117) |
| cyclo(FVGOYVWPOV) | (SEQ ID NO: 118) |
| cyclo(YVRGFVFGOV) | (SEQ ID NO: 119) |
| cyclo(YVOGFVFOGV) | (SEQ ID NO: 120) |

-continued

| | |
|---|---|
| cyclo(CYSOYCLWOGV) | (SEQ ID NO: 121) |
| cyclo(CVPOYCLWOGV) | (SEQ ID NO: 122) |
| cyclo(CVOOYCLWOGF) | (SEQ ID NO: 123) |
| cyclo(SVKGFKVKGF) | (SEQ ID NO: 124) |
| cyclo(FVGKYVLGKV) | (SEQ ID NO: 125) |
| cyclo(FVGKYVWPKV) | (SEQ ID NO: 126) |
| cyclo(YVKGFVFGKV) | (SEQ ID NO: 127) |
| cyclo(YAKGFVFGKV) | (SEQ ID NO: 128) |
| cyclo(CVKKYCLWKGV) | (SEQ ID NO: 129) |
| cyclo(CVSKYCLWKGV) | (SEQ ID NO: 130) |
| cyclo(CVSKYCLGW) | (SEQ ID NO: 131) |
| cyclo(CVPKYCLKGW) | (SEQ ID NO: 132) |
| cyclo(CGFRSCVGRWL) | (SEQ ID NO: 133) |
| cyclo(CIRGVCLWKGY) | (SEQ ID NO: 134) |
| cyclo(CGFRSCVGRW) | (SEQ ID NO: 135) |
| cyclo(CRGVCWRGY) | (SEQ ID NO: 136) |

The sequences are presented from residue $Z_1$ to $X_{28}$. The prefix "cyclo" indicates the peptides are cyclic. Residues followed with an asterisk (e.g., R*) are D-enantiomers.

In a preferred embodiment of the invention the peptides of formula I are characterized by a β-sheets region having two disulfide linkages and an odd number of amino acid residues between the cysteine-like amino acids on each strand.

Thus, in one preferred embodiment, the cyclic peptides of formula I are characterized by a β-sheets region containing an invariant conformation of two disulfide linkages (between residues $Z_1$ and $Z_{20}$ and residues $Z_6$ and $Z_{15}$, respectively) and a segment of ten amino acid residues (five amino acids per β-sheet strand) between the disulfide linkages. The ten-amino acid segment is characterized by an alternating pattern of hydrophobic and hydrophilic amino acids. In this preferred embodiment, the cyclic peptides of the invention have the formula:

$$
\begin{array}{c}
X_{26} - X_{27} - X_{28} - Z_1 - X_2 - (X_3 - X_4)_m - Z_6 - X_9 \\
/ \qquad \qquad \qquad \| \qquad \qquad \qquad \| \qquad \quad \backslash \\
X_{25} \qquad \qquad \qquad \| \qquad \qquad \qquad \| \qquad \quad X_{10} \\
| \qquad \qquad \qquad \quad \| \qquad \qquad \qquad \| \qquad \quad | \\
X_{24} \qquad \qquad \qquad \| \qquad \qquad \qquad \| \qquad \quad X_{11} \\
\backslash \qquad \qquad \qquad \| \qquad \qquad \qquad \| \qquad \quad / \\
X_{23} - X_{22} - X_{21} - Z_{20} - X_{19} - (X_{18} - X_{17})_m - Z_{15} - X_{12}
\end{array}
\qquad (II)
$$

wherein m=2;

∥ designates a disulfide linkage;

$X_{21}$, $X_{22}$, $X_{24}$, $X_{25}$, $X_{27}$ and $X_{28}$ are each independently present or absent;

$X_2$ is a hydrophobic amino acid;

$X_3$, $X_{18}$, $X_{22}$ and $X_{27}$ are each independently a hydrophilic amino acid or a small amino acid;

$X_4$, $X_{17}$, $X_{19}$, $X_{21}$ and $X_{28}$ are each independently a hydrophobic amino acid or a small amino acid;

$X_{23}$, $X_{24}$, $X_{25}$ and $X_{26}$ taken together are a loop;

$Z_1$, $Z_6$, $Z_{15}$ and $Z_{20}$ are each cysteine, homocysteine or penicillamine;

$X_9$, $X_{10}$, $X_{11}$ and $X_{12}$ taken together are a β-turn;

at least one of $X_9$, $X_{10}$, $X_{11}$, $X_{12}$, $X_{23}$, $X_{24}$, $X_{25}$ or $X_{26}$ is a basic amino acid; and wherein the peptide has a net positive charge at physiological pH.

In another preferred embodiment, the cyclic peptides of formula I are characterized by a β-sheets region containing an invariant conformation of two disulfide linkages (between residues $Z_1$ and $Z_{20}$ and residues $Z_6$ and $Z_{15}$, respectively) and a segment of six amino acid residues (three amino acids per β-sheet strand) between the disulfide linkages. The six-amino acid segment is characterized by an alternating pattern of hydrophobic and hydrophilic amino acids.

Thus, in another preferred embodiment the cyclic peptides of the invention have the formula:

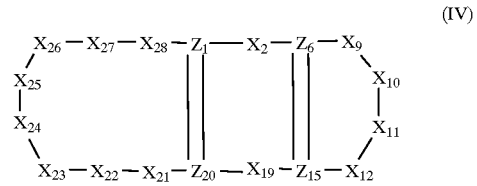

(III)

wherein ∥ designates a disulfide linkage;

$X_{21}$, $X_{22}$, $X_{24}$, $X_{25}$, $X_{27}$ and $X_{28}$ are each independently present or absent;

$X_2$ is a hydrophobic amino acid;

$X_3$, $X_{18}$, $X_{22}$ and $X_{27}$ are each independently a hydrophilic amino acid or a small amino acid;

$X_4$, $X_{17}$, $X_{19}$, $X_{21}$ and $X_{28}$ are each independently a hydrophobic amino acid or a small amino acid;

$X_{23}$, $X_{24}$, $X_{25}$ and $X_{26}$ taken together are a loop;

$Z_1$, $Z_6$, $Z_{15}$ and $Z_{20}$ are each cysteine, homocysteine or penicillamine;

$X_9$, $X_{10}$, $X_{11}$ and $X_{12}$ taken together are a β-turn;

at least one of $X_9$, $X_{10}$, $X_{11}$, $X_{12}$, $X_{23}$, $X_{24}$, $X_{25}$ or $X_{26}$ is a basic amino acid; and wherein the peptide has a net positive charge at physiological pH.

Preferred peptideds of formula III include the following

| | |
|---|---|
| cyclo(CLRYCRRRFCVRFCLWF) | (SEQ ID NO: 140) |
| cyclo(CLRYCRR*FCVRFCLWF) | (SEQ ID NO: 141) |
| cyclo(CLRYCRPFCVSYCVRWF) | (SEQ ID NO: 142) |
| cyclo(CLRYCRIPICVRFCVPRW) | (SEQ ID NO: 143) |
| cyclo(CLRYCRF*PFCVRFCLSRW) | (SEQ ID NO: 144) |
| cyclo(CL-Dpr-YCRRRFCVDYCVRGW) | (SEQ ID NO: 145) |
| cyclo(CL-Dpr-YCVRRFCVDYCVGW) | (SEQ ID NO: 146) |
| cyclo(CL-Dpr-YCRSRFCVDYCVGW) | (SEQ ID NO: 147) |

The sequences are presented from residue $Z_1$ to $X_{28}$. The prefix "cyclo" indicates that the peptides are cyclic. Residues followed with an asterisk (e.g., R*) are D-enantiomers.

In a final preferred embodiment, the cyclic peptides of formula I are characterized by a β-sheets region containing an invariant conformation of two disulfide linkages (between residues $Z_1$ and $Z_{20}$ and residues $Z_6$ and $Z_{15}$, respectively) and a segment of two amino acid residues (one amino acid per β-sheets strand) between the disulfide linkages. One of the amino acids comprising the segment is a hydrophobic amino acid; the other amino acid is a hydrophobic amino acid or a small amino acid.

Thus, in this final preferred embodiment the cyclic peptides of the invention have the formula:

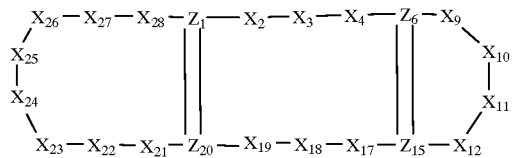

(IV)

wherein ∥ designates a disulfide linkage;

$X_{21}$, $X_{22}$, $X_{24}$, $X_{25}$, $X_{27}$ and $X_{28}$ are each independently present or absent;

$X_2$ is a hydrophobic amino acid;

$X_{22}$ and $X_{27}$ are each independently a hydrophilic amino acid or a small amino acid;

$X_{19}$, $X_{21}$ and $X_{28}$ are each independently a hydrophobic amino acid or a small amino acid;

$X_{23}$, $X_{24}$, $X_{25}$ and $X_{26}$ taken together are a loop;

$Z_1$, $Z_6$, $Z_{15}$ and $Z_{20}$ are each independently cysteine, homocysteine or penicillamine;

$X_9$, $X_{10}$, $X_{11}$ and $X_{12}$ taken together are a β-turn;

at least one of $X_9$, $X_{10}$, $X_{11}$, $X_{12}$, $X_{23}$, $X_{24}$, $X_{25}$ or $X_{26}$ is a basic amino acid; and wherein the peptide has a net positive charge at physiological pH.

Preferred cyclic peptides of formulae IV are as follows:

| | |
|---|---|
| cyclo(CYCRRRFCVCVL) | (SEQ ID NO: 150) |
| cyclo(CYCRRRFCVCVWY) | (SEQ ID NO: 151) |
| cyclo(CYCRGRFCVRW) | (SEQ ID NO: 152) |
| cyclo(CVCFR*R*RCYCLWV) | (SEQ ID NO: 153) |
| cyclo(CYCRRRFCVCVRL) | (SEQ ID NO: 154) |
| cyclo(CVCFR*R*RCYCLRV) | (SEQ ID NO: 155) |
| cyclo(CYCRRRFCVCIFGR) | (SEQ ID NO: 156) |
| cyclo(CYCRRRFCVCISGR) | (SEQ ID NO: 157) |
| cyclo(CYCRRRFCVCIRGV) | (SEQ ID NO: 158) |
| cyclo(CYCRRRFCVCIWGR) | (SEQ ID NO: 159) |
| cyclo(CYCRRRFCVCRFPY) | (SEQ ID NO: 160) |
| cyclo(CYCRRRFCVCRGFL) | (SEQ ID NO: 161) |
| cyclo(CYCRRRFCVCRGWV) | (SEQ ID NO: 162) |
| cyclo(CYCRRRFCVCRGWI) | (SEQ ID NO: 163) |
| cyclo(CYCRRRFCVCRIPA) | (SEQ ID NO: 164) |
| cyclo(CYCRRRFCVCYRGR) | (SEQ ID NO: 165) |
| cyclo(CYCRRRFCVCRLVF) | (SEQ ID NO: 166) |
| cyclo(CYCRRRFCVCVR-Cha) | (SEQ ID NO: 167) |
| cyclo(CYCRPRFCVCVR-Cha) | (SEQ ID NO: 168) |
| cyclo(CYCFRRFCVCVR-Cha) | (SEQ ID NO: 169) |
| cyclo(CYCRRRFCVCVRG-Cha) | (SEQ ID NO: 170) |
| cyclo(CYCRRRFCVCVRW) | (SEQ ID NO: 171) |
| cyclo(CYCRPRFCVCVRW) | (SEQ ID NO: 172) |
| cyclo(CYCRSRFCVCVR-Cha) | (SEQ ID NO: 173) |
| cyclo(CYCVRRFCVCVRW) | (SEQ ID NO: 174) |
| cyclo(CFCVOOFCVCFOV) | (SEQ ID NO: 175) |
| cyclo(CFCVOOYCVCVOW) | (SEQ ID NO: 176) |
| cyclo(CFCOPO*YCVCVO-Cha) | (SEQ ID NO: 177) |
| cyclo(CFCVOTYCVCVO-Cha) | (SEQ ID NO: 178) |
| cyclo(CFCV-MeGly-O*YCVCYOV) | (SEQ ID NO: 179) |
| cyclo(CYCOO*OFCVCVOWL) | (SEQ ID NO: 180) |
| cyclo(CYCOOOFCVCVOWL) | (SEQ ID NO: 181) |
| cyclo(CYCRGRFCVCVGRWL) | (SEQ ID NO: 182) |
| cyclo(CVCFR*R*RCYCLWRGV) | (SEQ ID NO: 183) |
| cyclo(CVCFR*R*RCYCLWGRV) | (SEQ ID NO: 184) |
| cyclo(CYCRRRFCVCVGRWL) (all D) | (SEQ ID NO: 185) |
| cyclo(CYCRPRFCVCVGRWL) | (SEQ ID NO: 186) |
| cyclo(CVCFRPRCYCLWRGV) | (SEQ ID NO: 187) |

-continued

| | |
|---|---|
| cyclo(CVCFPRRCYCLWRGV) | (SEQ ID NO: 188) |
| cyclo(CVCVGPRCYCLRGW) | (SEQ ID NO: 189) |
| cyclo(CYCRRRFCVCVRWL) | (SEQ ID NO: 190) |
| cyclo(CYCRRRFCVCVRGW) | (SEQ ID NO: 191) |
| cyclo(CYCRRRFCVCWRGV) | (SEQ ID NO: 192) |
| cyclo(CYCRPRFCVCWGRV) | (SEQ ID NO: 193) |
| cyclo(CYCRRRFCVCVRGW) | (SEQ ID NO: 194) |
| cyclo(CVCRPRWCYCLWSV) | (SEQ ID NO: 195) |
| cyclo(CYCRRRFCVCVGRWL) | (SEQ ID NO: 196) |
| cyclo(CYCRR*RFCVCVGRWL) | (SEQ ID NO: 197) |
| cyclo(CYCSRRYCVCYPRV) | (SEQ ID NO: 198) |
| cyclo(CYCVRRYCVCYGRWV) | (SEQ ID NO: 199) |
| cyclo(CYCGR*RYCVCYARWV) | (SEQ ID NO: 200) |
| cyclo(CVCRSRFCYCLWRGV) | (SEQ ID NO: 201) |
| cyclo(CVCRPRFCYCLWRGV) | (SEQ ID NO: 202) |
| cyclo(CVCYRFRCYCVWRGF) | (SEQ ID NO: 203) |
| cyclo(CYCRPRFCVCVGRPGWL) | (SEQ ID NO: 204) |
| cyclo(CYCRPRFCVCVGRGWL) | (SEQ ID NO: 205) |
| cyclo(CYCRGRFCVCVRGGRV) | (SEQ ID NO: 206) |
| cyclo(CYCVRRYCVCFGWARV) | (SEQ ID NO: 207) |
| cyclo(CYCRPRFCVCVGRRGWL) | (SEQ ID NO: 208) |
| cyclo(CYCRPRFCVCVGRRGGL) | (SEQ ID NO: 209) |
| cyclo(CYCRRRFCVCVGRRGGRL) | (SEQ ID NO: 210) |
| cyclo(CYCRGRFCVCVGRGGWRL) | (SEQ ID NO: 211) |
| cyclo(CYCRGRFCVCVGRRGLR-Cha) | (SEQ ID NO: 212) |
| cyclo(CYCRGRFCVCVGRRGWRL) | (SEQ ID NO: 213) |
| cyclo(CYCRPRFCVCVGRGRWRL) | (SEQ ID NO: 214) |
| cyclo(CYCRTRFCVCVGRRGWRL) | (SEQ ID NO: 215) |
| cyclo(CFCVRRFCVCFRV) | (SEQ ID NO: 216) |
| cyclo(CFCRPRYCVCVR-Cha) | (SEQ ID NO: 217) |
| cyclo(CFCRF*PYCVCVR-Cha) | (SEQ ID NO: 218) |
| cyclo(CFCVTRYCVCVR-Cha) | (SEQ ID NO: 219) |
| cyclo(CFCV-MeGly-R*YCVCYRV) | (SEQ ID NO: 220) |
| cyclo(CYCRR*RFCVCVRWL) | (SEQ ID NO: 221) |
| cyclo(CYCRRRFCVCVRWL) | (SEQ ID NO: 222) |
| cyclo(CYCVRRYCVCYRWV) | (SEQ ID NO: 223) |
| cyclo(CYCKKKFCVCVL) | (SEQ ID NO: 224) |
| cyclo(CYCKKKFCVCVWY) | (SEQ ID NO: 225) |
| cyclo(CYCKKKFCVCVWL) | (SEQ ID NO: 226) |
| cyclo(CYCKKKFCVCVKL) | (SEQ ID NO: 227) |
| cyclo(CFCKPFCVCVK-Cha) | (SEQ ID NO: 228) |
| cyclo(CYCRRRFCVCVL) | (SEQ ID NO: 229) |
| cyclo(CYCRGRFCVCVGRGGWRL) | (SEQ ID NO: 230) |

The sequences are presented from residue $Z_1$ to $X_{28}$. The prefix "cyclo" indicates the peptides are cyclic. Residues followed with an asterisk (e.g., R*) are D-enantiomers. Sequences composed entirely of D-enantiomers are designated "all-D".

While not intending to be bound by theory, it is believed that preferred cyclic peptides of formulae II–IV have stable amphiphilic β-sheets structures in solution, thereby effecting antimicrobial activity.

In a particularly preferred embodiment of the invention, in the peptides of formulae II–IV amino acid residues comprising the segment of the β-sheets region between the disulfide linkages (residues $X_2$, $X_3$, $X_4$, $X_5$, $X_{16}$, $X_{17}$ $X_{18}$ and $X_{19}$) are selected so as to avoid juxtaposing large bulky aromatic side chains. While not intending to be bound by theory, it is believed that steric hinderance between adjacent aromatic side chains causes significant destabilization of the β-sheets secondary structure, which results in loss of antimicrobial activity.

Thus, in a particularly preferred embodiment, in the peptides of formula II–IV amino acid residues comprising the segment of the β-sheets region between the disulfide linkages which are adjacent to an aromatic residue, either intrastrand-wise or interstrand-wise, are preferably polar or small amino acids. For example, when $X_2$-$X_3$-$X_4$ in formula II is W-R-V, preferred sequences for $X_{19}$-$X_{18}$-$X_{17}$ include, by way of example and not limitation, G-A-F, A-S-F, V-S-W, V-K-F, etc. A person of ordinary skill in the art can easily choose particularly preferred sequences for the peptides of formulae II–IV in a similar fashion without undue experimentation.

Particularly preferred cyclic peptides of formulae II–IV are as follows:

| | |
|---|---|
| cyclo(CYCRRRFCVCVWY) | (SEQ ID NO: 151) |
| cyclo(CYCRRRFCVCVRL) | (SEQ ID NO: 154) |
| cyclo(CYCRRRFCVCVGRWL) | (SEQ ID NO: 196) |
| cyclo(CYCRPRFCVCVGRGWL) | (SEQ ID NO: 205) |
| cyclo(CYCRPRFCVCVGRRGWL) | (SEQ ID NO: 208) |
| cyclo(CYCRRRFCVCVGRRGGRL) | (SEQ ID NO: 210) |
| cyclo(CYCRR*RFCVCVRWL) | (SEQ ID NO: 221) |
| cyclo(CYCRRRFCVCVWL) | (SEQ ID NO: 240) |
| cyclo(CVCFRRRCYCLWRGV) | (SEQ ID NO: 241) |

The sequences are presented from residue $Z_1$ to $X_{28}$. The prefix "cyclo" indicates that the peptides are cyclic. Residues followed with an asterisk (e.g., R*) are D-enantiomers.

5.3 Identification of Active Peptides

Generally, active cyclic peptides of the invention are identified using in vitro screening assay. Indeed, in many instances the cyclic peptides of the invention will be used in vitro as preservatives, topical antimicrobial treatments, etc. Additionally, despite certain apparent limitations of in vitro susceptibility tests, clinical data indicate that a good correlation exists between minimal inhibitory concentration (MIC) test results and in vivo efficacy of antibiotic compounds (Murray, 1994, Antimicrobial Susceptibility Testing, Poupard et al., eds., Plenum Press, New York; Knudsen et al., 1995, Antimicrob. Agents Chemother. 39(6):1253–1258). Thus, cyclic peptides useful for treating infections and diseases related thereto are also conveniently identified by demonstrated in vitro antimicrobial activity against specified microbial targets.

Generally, the in vitro antimicrobial activity of antimicrobial agents is tested using standard NCCLS bacterial inhibition assays, or MIC tests (see, National Committee on Clinical Laboratory Standards "Performance Standards for Antimicrobial Susceptibility Testing," NCCLS Document M100-S5 Vol. 14, No. 16, December 1994; "Methods for dilution antimicrobial susceptibility test for bacteria that grow aerobically-Third Edition," Approved Standard M7-A3, National Committee for Clinical Standards, Villanova, Pa.). It has been discovered, however, that these standard NCCLS MIC assays do not work well for identifying active peptides of the invention. Thus, preferably the compounds are screened using the modified NCCLS MIC assay and other assays provided in the Examples.

It will be appreciated that other assays as are well known in the art or that will become apparent to those having skill in the art upon review of this disclosure may also be used to identify active cyclic peptides of the invention. Such assays include, for example, the assay described in Lehrer et al., 1988, J. Immunol. Methods 108:153 and Steinberg and Lehrer, "Designer Assays for Antimicrobial Peptides: Disputing the 'One Size Fits All' Theory," In: Antibacterial Peptide Protocols, Shafer, Ed., Humana Press, N.J.

Generally, active peptides of the invention will exhibit MICs (as measured using the modified NCCLS assays provided in the Examples) of less than about 64 μg mL, usually less than about 32 μg/mL, preferably less than about 16 μg/mL and most preferably less than about 4 μg/mL.

5.4 Preparation of the Peptides 5.4.1 Chemical Synthesis

The cyclic peptides of the invention may be prepared using virtually any art-known technique for the preparation of cyclic peptides. For example, the peptides may be prepared in linear or non-cyclized form using conventional solution or solid phase peptide syntheses and cyclized using standard chemistries. Preferably, the chemistry used to cyclize the peptide will be sufficiently mild so as to avoid substantially degrading the peptide. Suitable procedures for synthesizing the peptides described herein as well as suitable chemistries for cyclizing the peptides are well known in the art.

For references related to synthesis of cyclic peptides the reader is referred to Dong et al., 1995, *J. Am. Chem. Soc.* 117:2726–2731; Ishida et al., 1995, *J. Org. Chem.* 60:5374–5375; WO 95/33765, published Jun. 6, 1995; Xue and DeGrado, 1994, *J. Org. Chem.* 60(4):946–952; Jacquier et al., 1991, In: *Peptides* 1990 221–222, Giralt and Andreu, Eds., ESCOM Leiden, The Netherlands; Schmidt and Neubert, 1991, In: *Peptides* 1990 214–215, Giralt and Andreu, Eds., ESCOM Leiden, The Netherlands; Toniolo, 1990, *Int. J. Peptide Protein Res.* 35:287–300; Ulysse et al., 1995, *J. Am. Chem. Soc.* 117:8466–8467; Dürr et al., 1991, *Peptides* 1990 216–218, Giralt and Andreu, Eds., ESCOM Leiden, The Netherlands; Lender et al., 1993, *Int. J. Peptide Protein Res.* 42:509–517; Boger and Yohannes, 1990, *J. Org. Chem.* 55:6000–6017; Brady et al., 1979, *J. Org. Chem.* 44(18):3101–3105; Spatola et al., 1986, *J. Am. Chem. Soc.* 108:825–831; Seidel et al., 1991, In: *Peptides* 1990 236–237, Giralt and Andreu, Eds., ESCOM Leiden, The Netherlands; and Tanizawa et al., 1986, *Chem. Phar, Bull.* 34(10):4001–4011.

It is to be understood that the chemical linkage used to covalently cyclize the peptides of the invention need not be an amide linkage. Indeed, in many instances it may be desirable to modify the N- and C-termini of the linear or non-cyclized peptide so as to provide, for example, reactive groups that may be cyclized under mild reaction conditions. Such linkages include, by way of example and not limitation amide, ester, thioester, $CH_2$—NH, etc. Techniques and reagents for synthesizing peptides having modified termini and chemistries suitable for cyclizing such modified peptides are well-known in the art.

Alternatively, in instances where the ends of the peptide are conformationally or otherwise constrained so as to make cyclization difficult, it may be desirable to attach linkers to the N- and/or C-termini to facilitate peptide cyclization. Of course, it will be appreciated that such linkers will bear reactive groups capable of forming covalent bonds with the termini of the peptide. Suitable linkers and chemistries are well-known in the art and include those previously described.

As will be readily appreciated by those having skill in the art, since the peptides of the invention are cyclic, the designation of the N- and C-terminal amino acids is arbitrary. Thus, the peptides of the invention can be synthesized in linear or non-cyclized form starting from any amino acid residue. Preferably, the peptides of the invention are synthesized in a manner so as to provide a linear or non-cyclized peptide that, when subjected to cyclization conditions, yields a substantial amount of cyclic peptide. While not intending to be bound by theory, it is believed that cyclizing the peptides of the invention in the loop region or β-turn region is preferable to cyclizing the peptides in the β-sheet region. Because the amino acid residues in the loop and/or turn region readily adopt relatively stable conformations, thereby juxtaposing the N- and C-termini of the amino acids to be covalently cyclized, it is believed that cyclizing such peptides in these regions is entropically favored as compared to cyclizing the peptides in the β-sheet region of the molecule. Thus, in a preferred embodiment the cyclic peptides of the invention are synthesized so as to provide linear or non-cyclized peptides wherein the N- and C-terminal amino acids reside in either the loop region or the β-turn region of the peptide. One of ordinary skill in the art will be able to choose an appropriate cyclization strategy for a particular peptide sequence without undue experimentation.

Alternatively, the cyclic peptides of the invention may be prepared by way of segment condensation. The preparation of both linear and cyclic peptides using segment condensation techniques is well-described in the art (see, e.g., Liu et al., 1996, *Tetrahedron Lett.* 37(7):933–936; Baca, et al., 1995, *J. Am. Chem. Soc.* 117:1881–1887; Tam et al., 1995, *Int. J. Peptide Protein Res.* 45:209–216; Schnölzer and Kent, 1992, *Science* 256:221–225; Liu and Tam, 1994, *J. Am. Chem. Soc.* 116(10):4149–4153; Liu and Tam, 1994, *Proc. Natl. Acad. Sci. USA* 91:6584–6588; Yamashiro and Li, 1988, *Int. J. Peptide Protein Res.* 31:322–334).

The disulfide linkages in bi-cyclic and tri-cyclic peptides of the invention may be formed before or after cyclizing the peptide. As the disulfide linkages will add stability to the peptide structure, and because the side chain thiol groups are reactive, it is preferable to form the disulfide linkages prior to cyclizing the peptide.

Formation of disulfide linkages, if desired, is generally conducted in the presence of mild oxidizing agents. Chemical oxidizing agents may be used, or the compounds may simply be exposed to atmospheric oxygen to effect these linkages. Various methods are known in the art, including those described, for example, by Tam, J. P. et al., 1979, *Synthesis* 955–957; Stewart et al., 1984, *Solid Phase Peptide Synthesis*, 2d Ed., Pierce Chemical Company Rockford, Ill.; Ahmed et al., 1975, *J. Biol. Chem.* 250:8477–8482; and Pennington et al., 1991 *Peptides* 1990 164–166, Giralt and Andreu, Eds., ESCOM Leiden, The Netherlands. An additional alternative is described by Kamber et al., 1980, *Helv Chim Acta* 63:899–915. A method conducted on solid supports is described by Albericio, 1985, *Int. J. Peptide Protein Res.* 26:92–97. Any of these methods may be used to form disulfide linkages in the peptides of the invention. Preferred methods for effecting disulfide-bridge formation for the peptides described herein are provided in the examples.

5.4.2 Recombinant Synthesis

If the peptide is composed entirely of gene-encoded amino acids, or a portion of it is so composed, the peptide or the relevant portion may also be synthesized using conventional recombinant genetic engineering techniques. The isolated peptides, or segments thereof, are then cyclized or condensed, and optionally oxidized, as previously described, to yield a cyclic peptide.

For recombinant production, a polynucleotide sequence encoding a linear or non-cyclized form of the cyclic peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the linear form of the cyclic peptide. Depending on the expression system used, the expressed peptide is then isolated by procedures well-established in the art. Methods for recombinant protein and peptide production are well known in the art (see, e.g., Maniatis et al., 1989, *Molecular Cloning A Laboratory Manual*, Cold Spring Harbor Laboratory, N.Y.; and Ausubel et al., 1989, *Current Protocols in Molecular Biology*, Greene Publishing Associates and Wiley Interscience, New York).

A variety of host-expression vector systems may be utilized to express linear or non-cyclized forms of the cyclic peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems. Of course, it will be appreciated that as non-cyclized or linear forms of the peptides of the invention may also be antimicrobial (see, e.g., U.S. Ser. No. 08/562,346, filed Nov. 22, 1995, and Attorney Docket No. 22000-20540.26, filed May 17, 1996, each of which is incorporated herein in its entirety by reference), preferably expression hosts are those against which the expressed peptides are not lethal or toxic.

The expression elements of the expression systems vary in their strength and specificities. Depending on the host vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of expression product, SV40-, BPV- and EBV-based vectors may be used with an appropriate selectable marker.

In cases where plant expression vectors are used, the expression of sequences encoding linear or non-cyclized forms of the cyclic peptides of the invention may be driven by any of a number of promoters. For example, viral promoters such as the 35S RNA and 19S RNA promoters of CaMV (Brisson et al., 1984, *Nature* 310:511–514), or the coat protein promoter of TMV (Takamatsu et al., 1987, *EMBO J.* 6:307–311) may be used; alternatively, plant promoters such as the small subunit of RUBISCO (Coruzzi et al., 1984, *EMBO J.* 3:1671–1680; Broglie et al., 1984, *Science* 224:838–843) or heat shock promoters, e.g., soybean hsp17.5-E or hsp17.3-B (Gurley et al., 1986, *Mol. Cell. Biol.* 6:559–565) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach, 1988, *Methods for Plant Molecular Biology*, Academic Press, New York, Section VIII, pp. 421–463; and Grierson & Corey, 1988, *Plant Molecular Biology*, 2d Ed., Blackie, London, Ch. 7–9.

In one insect expression system that may be used to produce linear or non-cyclized forms of the peptides of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (e.g., see Smith et al., 1983, *J. Virol.* 46:584; Smith, U.S. Pat. No. 4,215,051). Further examples of this expression system may be found in *Current Protocols in Molecular Biology*, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., See Logan & Shenk, 1984, *Proc. Natl. Acad. Sci. (USA)* 81:3655–3659). Alternatively, the vaccinia 7.5K promoter may be used, (see, e.g., Mackett et al., 1982, *Proc. Natl. Acad. Sci. (USA)* 79:7415–7419; Mackett et al., 1984, *J. Virol.* 49:857–864; Panicali et al., 1982, *Proc. Natl. Acad. Sci.* 79:4927–4931).

Other expression systems for producing liner or non-cyclized forms of the cyclic peptides of the invention will be apparent to those having skill in the art.

5.4.3 Purification of Cyclic Peptides

The cyclic peptides of the invention can be purified by art-known techniques such as high performance liquid chromatography, ion exchange chromatography, gel electrophoresis, affinity chromatography and the like. The actual conditions used to purify a particular cyclic peptide will depend, in part, on factors such as net charge, hydrophobicity, hydrophilicity, etc., and will be apparent to those having skill in the art.

For affinity chromatography purification, any antibody which specifically binds the cyclic peptide may be used. For the production of antibodies, various host animals, including but not limited to rabbits, mice, rats, etc., may be immunized by injection with a cyclic peptide. The peptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to a cyclic peptide may be prepared using any technique which provides for the production of antibody molecules by continuous cell lines in culture. These include but are not limited to the hybridoma technique originally described by Koehler and Milstein, 1975, *Nature* 256:495–497, the human B-cell hybridoma technique, Kosbor et al., 1983, *Immunology Today* 4:72; Cote et al., 1983, *Proc. Natl. Acad. Sci. U.S.A.* 80:2026–2030 and the EBVhybridoma technique (Cole et al., 1985, *Monoclonal Antibodies and Cancer Therapy,* Alan R. Liss, Inc., pp. 77–96 (1985)). In addition, techniques developed for the production of "chimeric antibodies" (Morrison et al., 1984, *Proc. Natl. Acad. Sci. U.S.A.* 81:6851–6855; Neuberger et al., 1984, *Nature* 312:604–608; Takeda et al., 1985, *Nature* 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce cyclic peptide-specific single chain antibodies.

Antibody fragments which contain deletions of specific binding sites may be generated by known techniques. For example, such fragments include but are not limited to F(ab')$_2$ fragments, which can be produced by pepsin digestion of the antibody molecule and Fab fragments, which can be generated by reducing the disulfide bridges of the F(ab')$_2$ fragments. Alternatively, Fab expression libraries may be constructed (Huse et al., 1989, *Science* 246:1275–1281) to allow rapid and easy identification of monoclonal Fab fragments with the desired specificity for the cyclic peptide of interest.

The antibody or antibody fragment specific for the desired cyclic peptide can be attached, for example, to agarose, and the antibody-agarose complex is used in immunochromatography to purify cyclic peptides of the invention. See, Scopes, 1984, *Protein Purification: Principles and Practice,* Springer-Verlag New York, Inc., New York, Livingstone, 1974, *Methods Enzymology: Immunoaffinity Chromatography of Proteins* 34:723–731.

6. FORMULATION, ADMINISTRATION AND DOSAGES 6.1 Compositions and Administration The cyclic peptides of the invention can be used in a wide variety of applications to inhibit the growth of or kill microorganisms. For example, the cyclic peptides can be used as disinfectants or as preservatives for materials such as foodstuffs, cosmetics, medicaments and other nutrient-containing materials. The cyclic peptides can also be used to treat or prevent diseases related to microbial infection in both plants and animals.

For use as a disinfectant or preservative the cyclic peptides can be added to the desired material singly, as mixtures of several cyclic peptides or in combination with other antimicrobial agents. The cyclic peptides may be supplied as the peptide per se or may be in admixture with a variety of carriers, diluents or excipients as are well known in the art.

When used to treat or prevent infections or diseases related thereto, the cyclic peptides of the invention can be administered or applied singly, as mixtures of cyclic peptides, in combination with other antimicrobial or antibiotic agents or in combination with other pharmaceutically active agents. The cyclic peptides can be administered or applied per se or as pharmaceutical compositions.

Pharmaceutical compositions comprising the cyclic peptides of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active peptides into preparations which can be used pharmaceutically. Proper formulation is dependent upon the route of administration chosen.

For topical administration the cyclic peptides of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal oral or pulmonary administration.

For injection, the peptides of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the peptide may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the compounds can be readily formulated by combining the active peptides with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compositions may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may also be formulated in rectal or vaginal compositions such as suppositories or retention enemas, e.g, containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As the cyclic peptides of the invention may contain charged side chains, they may be included in any of the above-described formulations as the free bases or as pharmaceutically acceptable salts. Pharmaceutically acceptable salts are those salts which substantially retain the antimicrobial activity of the free bases and which are prepared by reaction with inorganic acids. Pharmaceutical salts tend to be more soluble in aqueous and other protic solvents than are the corresponding free base forms.

6.2 Effective Dosages

The cyclic peptides of the invention, or compositions thereof, will generally be used in an amount effective to achieve the intended purpose. Of course, it is to be understood that the amount used will depend on the particular application.

For example, for use as a disinfectant or preservative, an antimicrobially effective amount of a cyclic peptide, or composition thereof, is applied or added to the material to be disinfected or preserved. By antimicrobially effective amount is meant an amount of peptide or composition that inhibits the growth of, or is lethal to, a target microbe population. While the actual antimicrobially effective amount will depend on a particular application, for use as a disinfectant or preservative the cyclic peptides, or compositions thereof, are usually added or applied to the material to be disinfected or preserved in relatively low amounts. Typically, the cyclic peptide comprises less than about 5% by weight of the disinfectant solution or material to be preserved, preferably less than about 1% by weight and more preferably less than about 0.1% by weight. An ordinarily skilled artisan will be able to determine autimicrobially effective amounts of particular peptides for particular applications without undue experimentation using, for example, the in vitro assays provided in the examples.

For use to treat or prevent microbial infections or diseases related thereto, the peptides of the invention, or compositions thereof, are administered or applied in a therapeutically effective amount. By therapeutically effective amount is meant an amount effective ameliorate the symptoms of, or ameliorate, treat or prevent microbial infections or diseases related thereto. Determination of a therapeutically effective amount is well within the capabilities of those skilled in the art, especially in light of the detailed disclosure provided herein.

As in the case of disinfectants and preservatives, for topical administration to treat or prevent bacterial, yeast, fungal or other infections a therapeutically effective dose can be determined using, for example, the in vitro assays provided in the examples. The treatment may be applied while the infection is visible, or even when it is not visible. An ordinarily skilled artisan will be able to determine therapeutically effective amounts to treat topical infections without undue experimentation.

For systemic administration, a therapeutically effective dose can be estimated initially from in vitro assays. For example, a dose can be formulated in animal models to achieve a circulating cyclic peptide concentration range that includes the $I_{50}$ as determined in cell culture (i.e., the concentration of test compound that is lethal to 50% of a cell culture), the MIC, as determined in cell culture (i.e., the minimal inhibitory concentration for growth) or the $I_{100}$ as determined in cell culture (i.e., the concentration of peptide that is lethal to 100% of a cell culture). Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the active peptide which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of peptide may not be related to plasma concentration. One having skill in the art will be able to optimize therapeutically effective local dosages without undue experimentation.

The amount of peptide administered will, of course, be dependent on the subject being treated, on the subject's weight, the severity of the affliction, the manner of administration and the judgment of the prescribing physician.

The antimicrobial therapy may be repeated intermittently while infections are detectable or even when they are not detectable. The therapy may be provided alone or in combination with other drugs, such as for example antibiotics or other antimicrobial peptides.

6.3 Toxicity

Preferably, a therapeutically effective dose of the peptides described herein will provide therapeutic benefit without causing substantial toxicity.

Toxicity of the cyclic peptides described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the peptides described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics,* Ch.1, p.1).

The invention having been described, the following examples are offered by way of illustration and not limitation.

7. EXAMPLE

Peptide Syntheses

The following examples provide preferred methods for synthesizing cyclic peptides of the invention. The following abbreviations are used:

DPPA=diphenylphosphoryl azide
DMF=dimethylformamide
DIEA=diisopropylethylamine
DMSO=dimethylsulfoxide
EDT=1,2-ethanedithiol
DCC=N,N'-dicyclohexylcarbodiimide
HOBT=1-hydroxybenzotriazole
TFA=trifluoroacetic acid

7.1 Synthesis of Cyclo(CYCRRRFCVCVGRWL) (SEQ ID NO:196)

7.1.1 Synthesis of Linear Peptide

Peptide sequence CYCRRRFCVCVGRWL was synthesized on a Fmoc Arg(PMC) HMP solid support resin (Bachem) using Fmoc chemistry on an ABI 433 peptide synthesizer (ABD, Perkin Elmer, Foster City, Calif.) according to the manufacturer's standard protocols. Cleavage was carried out in 10 mL of thioanisole:EDT:TFA (1:1:9) for 2 hours at room temperature. Crude cleavage product was precipitated with t-butyl methyl ether, filtered and dried.

7.1.2 Formation of Disulfide Linkages

The crude linear peptide was dissolved in DMSO and added 20 mM ammonium acetate, pH 7. The final concentration of peptide was about 1–8 mg/mL, the pH ranged from 7.0–7.2 and the DMSO concentration ranged from about 5–20%. The solution was stirred overnight at room temperature, and the pH adjusted to pH 5 with concentrated acetic acid.

The oxidized peptide was loaded onto a preparative reverse-phase HPLC column (Vydac C18, 2.2 cm×25 cm, Cat. No. 218TP101522), the column was washed with buffer (10% v/v acetonitrile, 0.1% v/v TFA in water) until absorbance of the effluent (measured at 235 cm) reached baseline and the pure product was eluted at 10 mL/min. using the following buffers and gradient:

| Gradient | | | |
| --- | --- | --- | --- |
| Time (min.) | Buffer A (%) | Buffer B (%) | Gradient |
| 0 | 90 | 10 | linear |
| 10 | 82 | 18 | linear |
| 80 | 68 | 32 | linear |
| 95 | 5 | 95 | linear |

Buffer A = 0.10% (v/v) aqueous TFA;
Buffer B = 0.08% (v/v) TFA in acetonitrile.

Fractions were analyzed by analytical HPLC. Fractions containing the desired disulfide-bridged peptide (retention time was about 14–15 min.) were pooled, the acetonitrile stripped and the resultant aqueous solution lyophilized to dryness. The sequence of the disulfide-bridged peptide was confirmed by mass spectrometry.

7.1.3 Cyclization of Disulfide Bridged Peptide

Cyclization of the disulfide bridged peptide was carried out using two different methods.

Method A. 224 mg purified disulfide-bridged peptide was dissolved in DMF (22 mL) and NaHCO$_3$ (66 mg) added. The mixture was cooled to 0° C. and 36 mL DPPA added (the peptide concentration was between 1–10 mg/mL and 2–4 equivalents of DPPA were added). The reaction mixture was stirred at 4° C. for 7 days. The formation of cyclized peptide was determined by analytical HPLC (Vydac C18, 0.4 cm×25 cm, Cat. No. 218TP54) using a linear gradient of 30% to 70% Buffer B (0.08% TFA/70% acetonitrile/H$_2$O) over 30 min. at a flow rate of 1 mL/min. (Buffer A was 0.1% TFA/H$_2$O). The formation of cyclized peptide was indicated by a shift in retention time. Starting material eluted at 14.85 min. and cyclized peptide eluted at 20.8 min. HPLC indicated that the conversion yield was about 35%.

The reaction mixture was diluted with 400 mL 0.1% (v/v) aqueous TFA and the cyclized peptide purified by preparative reverse-phase HPLC as described above. Fractions containing the pure cyclized peptide were pooled, the acetonitrile was stripped and the resultant aqueous solution was lyophilized to dryness. The overall yield was about 10–20%. The sequence was confirmed by mass spectrometry (MW 1897.8).

Method B. 435 mg of pure disulfide bridged peptide was dissolved in DMF (40 mL). The mixture was cooled to 0° C. and 500 mg (15 equiv.) of DCC and 370 mg (10 equiv.) of HOBT were added. The reaction mixture was stirred overnight at room temperature. The formation of cyclized peptide was determined by analytical HPLC, as described above. The conversion yield was about 75%.

The reaction mixture was diluted with 900 mL 0.1% (v/v) aqueous TFA and the cyclized peptide purified by preparative HPLC as previously described. The overall yield was about 30–45%. The sequence of the cyclized peptide was confirmed by mass spectrometry (MW 1897.8).

7.2 Other Peptides

Cyclo(CYCRRRFCVCVWL) (SEQ ID NO:240), cyclo (CYCRRRFCVCVWY) (SEQ ID NO:151), cyclo (CYCRRRFCVCVGRWL) (SEQ ID NO:196), cyclo (CYCRRRFCVCVGRRGGRL) (SEQ ID NO:210) and cyclo(CYCRRRFCVCVRL) (SEQ ID NO:154) were synthesized as described above. Other cyclic peptides of the invention may be synthesized using the above-protocols or by techniques that are well-known in the art.

8. EXAMPLE

In Vitro Assays

The following examples provide preferred assays for measuring the antimicrobial activity of the cyclic peptides described herein. The following equipment, reagents, stock solutions and cultures are used in the assays that follow.

Microorganisms: *Escherichia coli* ML-35p and vancomycin-resistant *Enterococcus faecium* (VRE) were obtained from Dr. Robert Lehrer (UCLA, see also, Lehrer et al., 1988, *J. Immunol. Methods* 108:153) and Dr. Gary Schoolnik (Stanford), respectively. *Pseudomonas aeruginosa* (ATCC 9027), *Candida albicans* (ATCC 1023), and methicillin resistant *Staphylococcus aureus* (ATCC 33591) were obtained from the American Type Culture Collection, Rockville, Md.

Microorganisms from other sources, such as, for example, clinical isolates, can be used interchangeably with the above-described microorganisms in the assays described herein.

Media and Reagents:

Trypticase Soy Agar (TSA; Becton-Dickinson, Cockeysville, Md., BBL #4311768): dissolve 40 g in 1 Liter deionized water, autoclave 121° C., 20 minutes.

Trypticase Soy Broth (TSB; Becton-Dickinson, Cockeysville, Md., BBL #4311768): dissolve 30 g in 1 Liter deionized water, autoclave 121° C., 20 minutes, and store at room temperature.

2x Trypticase Soy Broth (2x TSB): dissolve 60 g in 1 Liter deionized water, autoclave 121° C., 20 minutes, and store at room temperature.

Glycerol (20% v/v): mix 20 mL glycerol with 80 mL deionized water, Filter sterilize with $0.20\mu$ filter and store at room temperature.

Monobasic phosphate buffer (100 mM): dissolve 13.7 g sodium phosphate monobasic (Fisher #S368-500) in 1 Liter deionized water. Filter sterilize with $0.20\ \mu$ filter and store at room temperature.

Dibasic phosphate buffer (100 mM): dissolve 14.2 g sodium phosphate dibasic (Fisher #S374-500) in 1 Liter deionized water. Filter sterilize with $0.45\mu$ filter and store at room temperature.

Phosphate-buffered saline (PBS; 10 mM phosphate, 100 mM NaCl, pH 7.4): mix 15 mL dibasic phosphate buffer (100 mM), 5 mL monobasic phosphate buffer (100 mM), 4 mL NaCl (5M) and 176 mL deionized water. Adjust pH if necessary, filter sterilize with $0.45\mu$ filter and store at room temperature.

Phosphate buffer (100 mM, pH 6.5): mix 40 mL dibasic phosphate buffer (100 mM) with 160 mL monobasic phosphate buffer (100 mM). Adjust pH if necessary, filter sterilize with $0.45\mu$ filter and store at room temperature.

Liquid Testing Medium (LTM): aseptically combine the following sterile ingredients: 10 mL Phosphate buffer (100 mM, pH 6.5), 1.0 mL TSB, 2 mL NaCl (5M) and 87 mL deionized water. Store at room temperature.

Acetic acid (0.01% v/v): mix 10 $\mu$L acetic acid with 100 mL sterile deionized water.

Agarose: mix 1 g agarose (Sigma #S6013) in 80 mL deionized water, autoclave 121° C., 20 minutes.

Agarose Underlay Medium: combine 10 mL Phosphate buffer (100 mM, pH 6.5), 1.0 mL TSB, 2 mL NaCl (5M) and 7 mL deionized water with 80 mL tempered (50° C.) agarose.

2x TSB Agarose Overlay Medium: dissolve 60 g TSB and 10 g agarose in 1 Liter deionized water, aliquot 100 mL per bottle, autoclave 121° C., 20 minutes, and store at room temperature.

Equipment & Materials:

Sterile inoculation loops

Sterile Erlenmeyer flasks (50 mL and 250 mL)

Spectrophotometer (LKB Ultrospec II)

Sterile 96 well polypropylene microtiter plates (Costar, Cambridge, Mass.; Cat # 3790)

Sterile polypropylene tips (Rainin Cat # RT20S)

Micropipettor: 10–200 $\mu$L range; P20 and P200.

Multichannel micropipettors: 10–50 $\mu$L and 50–200 $\mu$L range

Sterile pipettes: 1 mL, 10 mL

Sterile polypropylene centrifuge tubes (50 mL)

Vortex mixer

Sterile V-well troughs (Costar; Cat # 4870)

Sterile 24 well microtiter plates (Costar; Cat # 5324)

Square petri dishes (NUNC # 4021)

Stainless steel canula (3 mm i.d.)

Pasteur pipettes

Vacuum pump

Filter flask (1 L)

Preparation of Microorganism Slants: Each strain was cultured on TSA. Isolated colonies were transferred into TSB (10 mL in a sterile 50 mL Erlenmeyer flask) using a sterile, disposable loop and the flask incubated at 37° C. (bacteria) or 30° C. (yeast) with shaking (200 RPM) for 16–18 hours.

Broth cultures were diluted 1:1 with 20% sterile glycerol and stored as 1.0 mL aliquots at −80° C. For daily inocula, liquid was transferred from a thawed vial using a sterile loop and then spread onto the surface of TSA slants. The screw capped tubes were incubated overnight and stored at 4° C. for up to one month.

Preparation of Inoculum:

1. Remove the cap from tube and lightly touch a sterile loop to the area of heavy growth on the TSA slant.
2. Inoculate 10 mL of TSB (50 mL flask) and incubate the flask in a shaking water bath for 18 hours (overnight) at 37° C. (bacteria) or 30° C. (yeast) at 200 RPM.
3. In a cuvette, dilute 50 $\mu$L of the overnight culture 1:20 with TSB and measure the absorbance at 600 nm ($A_{600}$) using TSB as a reference. The $A_{600}$ of the diluted culture should be between 0.1–0.4.
4. In a 250 mL Erlenmeyer flask, dilute 50 $\mu$L of the overnight culture 1:1000 with TSB (bacteria) or 1:100 with TSB (yeast).
5. Incubate the flask in a shaking water bath at 37° C. (bacteria) or 30° C. (yeast) at 200 RPM for approximately 2–3 hours until log-phase is reached, i.e. until the $A_{600}$ of the culture is between 0.200 and 0.400 without further dilution.
6. Transfer 25 mL of the log-phase culture to a sterile centrifuge tube and centrifuge at 2000 rpm and 4° C. for 10 minutes. Decant the supernatant, add 25 mL of sterile PBS and resuspend the pellet by vortexing.
7. Centrifuge the suspension at 2000 rpm and 4° C. for 10 minutes. Decant the supernatant and resuspend the pellet with 5 ml sterile PBS.
8. Measure the $A_{600}$ of the undiluted suspension. If the absorbance is above 0.5, dilute with sterile PBS until the absorbance is between 0.100 and 0.500.
9. Determine the number colony-forming units per milliliter suspension (CFUs/mL) by preparing 10-fold serial dilutions in saline (0.87%) and spreading 100 $\mu$L of the $10^4$-, $10^5$-, and $10^6$-fold dilutions onto TSA plates, one dilution per plate. Incubate overnight, count the number of colonies and determine the CFUs/mL (an accurate determination requires approximately 30–300 colonies per plate).

For the strains reported, the CFUs/mL for a suspension having an $A_{600}$=0.2 have been determined as reported in Table 2, below:

TABLE 2

| Strain | CFUs/mL |
|---|---|
| \multicolumn{2}{c}{CFUs/mL of Suspension ($A_{600}$ = 0.2)} | |
| E. coli | $8.0 \times 10^7$ |
| P. aeruginosa | $7.8 \times 10^7$ |
| MRSA | $2.0 \times 10^7$ |

TABLE 2-continued

| CFUs/mL of Suspension ($A_{600} = 0.2$) | |
|---|---|
| Strain | CFUs/mL |
| VRE | $3.8 \times 10^7$ |
| C. albicans | $9.7 \times 10^5$ |

Preparation of Cyclic Peptide Stock Solutions:
1. weigh approximately 1.0 mg of each cyclic peptide to be tested into a sterile polypropylene cryovial (1.8 mL).
2. Add sufficient acetic acid (0.01%) to make a stock solution having a concentration of 1280 µg/mL. Dispense the stock solution into several vials, 100 µL per vial, and store the aliquots, tightly sealed, at −80° C.

8.1 Radial Diffusion (MCZ) Assay

The MCZ assay uses minimal amounts of test materials to determine the sensitivity of microorganisms to various antimicrobial compounds. Cells are grown to approximately mid-log phase and resuspended in minimal nutrient buffered agarose. Agarose (not agar) is used in this gel to avoid electrostatic interactions between antimicrobial peptides and the polyanionic components of standard agar. Peptides diffuse radially into the gels from small wells and the diameter of the zone of growth inhibition is proportional to the concentration of peptide in the solution (Lehrer et al., 1988, *J. Immunol. Methods* 108:153).

Preparation of MCZ Assay Plates:
1. For each petri plate to be poured, dispense 10 mL of tempered (50° C.) Agarose Underlay Medium into a sterile polypropylene tube (15 mL). Add $4 \times 10^6$ CFUs of the desired strain to each tube. Mix well by inverting tube 3 times. Immediately pour the molten agarose into the petri dishes.
2. After the agarose has solidified, use a sterile canula (3 mm i.d.) to punch 16 wells (4×4 evenly spaced grid) into the agarose. Remove the agarose plugs with a pasteur pipette and trap the agarose in a flask with a side arm port attached to a vacuum.
3. From the peptide stock solution, prepare serial 2-fold dilutions (from 128 82 g/mL to 0.06 µg/mL) using acetic acid (0.01%) as a diluent, or, for peptide concentrations lower than 50 µg/mL, sodium acetate (10 mM, pH 5) containing Human Serum Albumin (HSA; 0.1% w/v) as a diluent.
4. Dispense 5 µL of each serial dilution into the agarose wells, one serial dilution per well.
5. Dispense diluents into wells as negative controls and protegrin-1 (U.S. Pat. No. 5,464,823; 32 µg/mL, 8 µg/mL and 2 µg/mL) into wells as positive controls.
6. Incubate the plates at 37° C. (bacteria) or 30° C. (yeast) for 3 hours.
7. Dispense 2× TSB Agarose Overlay Medium (10 mL) onto the surface of each plate, allow the agar to solidify and incubate plates, inverted, at 37° C. (bacteria) or 30° C. (yeast) for 16–18 hours.
8. Examine the plates and measure (in mm) the diameter of the zone of growth inhibition (area of clearing around each well).
9. Plot the diameter of the zone of growth inhibition (Y-axis) versus the concentration of peptide in the well (X-axis) and obtain the line of best fit using linear regression analysis. The X-intercept of the line of best fit is the minimum concentration for zone of growth inhibition (MCZ) for each peptide concentration.

8.2 Microbroth Dilution (MCB) Assay

The microbroth dilution method accomodates large numbers of samples and is more amenable to automation than the MCZ assay and the data analysis is direct and simple. A key step in this assay is combining microorganisms and peptide in a defined minimal nutrient buffer system that minimizes interference with the peptide's biological activity. In addition, the presence of 0.1% (w/v) human serum albumin (HSA) to the peptide diluent minimizes adsorption of peptide to the container.

Preparation of MCB assay plates:
1. Dispense 100 µL of log-phase cells in LTM ($4 \times 10^5$ CFUs/mL) into each well of a sterile 96-well microtiter plate.
2. From the peptide stock solution, prepare serial two-fold dilutions (from 1280 µg/mL to 0.625 µg/mL) using acetic acid (0.01%) as a diluent, or, for peptide concentrations lower than 50 µg/mL, sodium acetate (10 mM, pH 5) containing Human Serum Albumin (HSA; 0.1% w/v) as a diluent.
3. Dispense triplicate aliquots (11 µL) of each serial two-fold dilution into the wells of the microtiter plate.
4. Incubate the plate at 37° C. (bacteria) or 30° C. (yeast) for 3 hours.
5. Add 100 µL of 2× TSB to each well, mix, and incubate at 37° C. (bacteria) or 30° C. (yeast) for an additional 16–18 hours.
6. Examine the plates and evaluate each well for turbidity (cell growth). Often, MRSA will settle out and form a pellet at the bottom of the well. MRSA can be evaluated by placing the microtiter plate on a stand and examining the bottom of the well using a tilted mirror.
7. The minimum concentration for inhibition of growth in broth medium (MCB) is defined as the lowest concentration of peptide that inhibits all visible growth. If the MCB values for each of the triplicate samples differ, the MCB is obtained by averaging the results of the three samples.
8. The minimum concentration of peptide showing 100% biocidal activity is determined by incubating a 10 µL aliquot from each well on a TSA plate for 24 hours at 37° C. (bacteria) or 30° C. (yeast) (for plating, 1.5 mL TSA in each well of a 24-well plate minimizes cross contamination).

8.3 Modified NCCLS Minimum Inhibitory Concentration (MIC) Assay

The National Committee for Clinical Standards (NCCLS) requires that test compounds be prepared as stock solutions in Meuller-Hinton Broth ("MHB") at 512 µg/mL. The stock solutions are serially diluted (two-fold) in medium and each serial dilution added 1:1 to medium containing $1 \times 10^6$ CFU/mL bacteria (National Committee on Clinical Laboratory Standards, December 1994, "Performance Standards for Antimicrobial Susceptibility Testing," *NCCLS Document M100-S5* Vol. 14, No. 16; *Methods for Dilution Antimicrobial Susceptibility Test for Bacteria that Grow Aerobically*, 3d Ed., Approved Standard M7-A3, National Committee for Clinical Standards, Villanova, Pa.).

It has been found that the cyclic peptides of the invention precipitate in MHB at concentrations greater than 128 µg/mL. Thus, following the NCCLS protocol would result in serial two-fold dilutions containing less peptide than calculated, yielding erroneously high MIC values.

To overcome this problem, the following modified NCCLS assay is the preferred method for determining MICs of the cyclic peptides of the invention. In the method, precipitation is avoided by preparing concentrated (10×) stock solutions of test peptide in a buffer that is suitable for the peptide and which does not exhibit deleterious effects on the microorganisms (0.01% v/v acetic acid, 0.1% w/v HSA) and diluting the stock 1:10 into MHB containing the microorganisms.

Preparation of MIC assay plates:
1. Prepare a fresh overnight culture of test organism in Meuller-Hinton broth (MHB; Becton-Dickinson, Cockysville, Md., BB2 #11443).
2. Dilute the culture to approximately $4 \times 10^5$ CFUs/mL with fresh MHB and dispense 100 μL aliquots into each well of a sterile 96-well microtiter plate.
3. From the peptide stock solution, prepare serial two-fold dilutions (from 1280 μg/mL to 0.625 μg/mL) using acetic acid (0.01%) as a diluent, or, for peptide concentrations lower than 50 μg/mL, sodium acetate (10 mM, pH 5) containing Human Serum Albumin (HSA; 0.1% w/v) as a diluent.
4. Dispense triplicate aliquots (11 μL) of each serial dilution into the wells of the microtiter plate.
5. Incubate the plate for 16–18 hours, without aeration, at 37° C. (bacteria) or 30° C. (yeast).
6. Examine the plates and evaluate each well for turbidity (cell growth). Often, MRSA will settle out and form a pellet at the bottom of the well. MRSA can be evaluated by placing the microtiter plate on a stand and examining the bottom of the well using a tilted mirror.
7. The minimum inhibitory concentration (MIC) is defined as the lowest peptide concentration that inhibits all visible growth. If the MIC values for each of the triplicate samples differ, the MIC is obtained by averaging the results of the three samples.
8. The minimum concentration of peptide showing 100% biocidal activity is determined by incubating a 10 μL aliquot from each well on a TSA plate for 24 hours at 37° C. (bacteria) or 30° C. (yeast) (for plating, 1.5 mL TSA in each well of a 24-well plate minimizes cross contamination).

The MIC values for protegrin-1 (U.S. Pat. No. 5,464,823) against *P. aeruginosa*, MRSA and VRE (obtained in different diluents) is provided in Table 3, below.

TABLE 3

MIC (μg/mL) Values for Protegrin-1

| Organism | Acetic Acid Diluent | Sodium Acetate-HSA Diluent |
|---|---|---|
| *Pseudomonas aeruginosa* | 8 | 1.3 |
| MRSA | 13.3 | 5.3 |
| VRE | 2 | ≤0.25 |

8.4 Kinetic Bactericidal Assay

The following assay is used to determine the rate at which a cyclic peptide kills a target microorganism, as well as to determine if a cyclic peptide is bactericidal or bacteriostatic.

Assay
1. Dispense 200 μL of log-phase cells in LTM ($4 \times 10^5$ CFUs/mL) into each well of a 96-well microtiter plate solution.
2. At time T=0 minutes, add 22 μL of 1280 μg/mL peptide to well A1 and mix by triturating 3 times.
3. Wait 30 seconds and add 22 μL of a second concentration of peptide the to the next well (A2) and mix by triturating 3 times.
4. Repeat the process, staggering each peptide addition by 30 seconds, until all concentrations of peptide have been added. Typically, 4-fold serial dilutions of stock peptide (i.e., 1280, 320, 80, 20 and 5 μg/mL peptide diluted 1:10 into each well) produces good comparative kill curves. Add 22 μL of 0.01% acetic acid to one well as a control.
5. At time T=15 minutes, mix well A1 by triturating 3 times and transfer 20 μL to an empty sterile petri dish (100 mm×15 mm).
6. Quickly add 20 mL of tempered (50° C.) TSA and gently swirl plate to mix.
7. Repeat steps 5–6 until all peptide concentrations have been plated.
8. For the control well, dilute the sample 1:100 with LTM and plate 50 μL of the dilution to obtain an accurate determinations of CFUs.
9. After the agar has solidified, invert the plates and incubate at 37° C. (bacteria) 30° C. (yeast) for 18–24 hours.
10. Repeat steps 5–9 for all peptide concentrations and control samples at times T=30, 60, 120, and 240 minutes.
11. Count the number of CFUs per plate and estimate the reduction in CFUs for each peptide concentration. In order to assess an effect using this assay, the peptide must reduce the CFUs by at least one log (i.e., at least 800 CFUs per plate). Although such numbers are higher than recommended for accuracy (30–300 CFUs/plate), log-order changes in recoverable CFUs indicate significant bacteriocidal efficacy.
12. To obtain comparative kill curves, plot the log of fractional survival versus peptide concentration.

8.5 Results

The results obtained from the above-described assays for exemplary cyclic peptides of the invention are set forth in Table 4, below.

TABLE 4

In Vitro Assay Data for Selected Strains and Cyclic Peptides

| | MIC Values (μg/mL) | | MRSA Kill Kinetics (2 μg/mL; log reduction*) | |
|---|---|---|---|---|
| Sequence | Psa | MRSA | 15 min | 120 min |
| RGGRLCYCRRRFCVCVGR† (protegrin-1) | 1.67 | 4 | 0.73 | 0.71 |
| RGGRLCYCRRRFCVCVGR | 0.5 | 4 | | |
| cyclo(CYCRRRFCVCVGRRGGRL) (SEQ ID NO: 210) | 8 | 5.33 | 1.2 | 1.17 |
| WLCYCRRRFCVCV† | >32 | 3.33 | 2.12 | 2.89 |
| WLCYCRRRFCVCV | 13 | 32 | | |
| cyclo(CYCRRRFCVCVWL) (SEQ ID NO: 240) | >32 | 4 | 2.65 | 2.18 |
| RLCYCRRRFCVCVV† | 4 | 2 | | |
| RLCYCRRRFCVCV | 2 | 10.7 | | |
| cyclo(CYCRRRFCVCVRL) (SEQ ID NO: 154) | 2.67 | 16 | | |
| WYCYCRRRFCVCV | 32 | 43 | | |
| cyco(CYCRRRFCVCVWY) (SEQ ID NO: 151) | 32 | 8 | | |
| WLCYCRRRFCVCVGR† | | | 1.79 | 2.26 |
| WLCYCRRRFCVCVGR | 32 | 32 | <0.46 | <0.46 |

TABLE 4-continued

In Vitro Assay Data for Selected Strains and Cyclic Peptides

| Sequence | MIC Values (μg/mL) | | MRSA Kill Kinetics (2 μg/mL; log reduction*) | |
|---|---|---|---|---|
| | Psa | MRSA | 15 min | 120 min |
| cyclo(CYCRRRFCVCVGRWL) (SEQ ID NO: 196) | 8 | 2 | 3.06 | >3.44 |

†Indicates C-terminal amidation
Psa is *Pseudomonas aeruginosa*
*log reduction values are measured from an initial value of $3.3 \times 10^5$ CFUs The present invention is not to be limited in scope by the exemplified embodiments, which are intended as illustrations of single aspects of the invention, and any sequences which are functionally equivalent are within the scope of the invention. Indeed, various modifications of the invention in addition to those described above will become apparent to those skilled in the art from the foregoing description and accompanying drawings. Such modifications are intended to fall within the scope of the appended claims.

All references cited herein are hereby incorporated herein in their entireties by reference.

What is claimed is:

1. A cyclic peptide comprising an amphiphilic antiparallel β-sheet region, a loop region and a β-turn region, wherein:

the cyclic peptide has a net positive charge at physiological pH;

at least one amino acid residue in either the loop region or the β-turn region is a basic amino acid, wherein the peptide has antimicrobial activity against *E. coil, Pseudomonas aeruginosa*, methicillin-resistant *Staphylococcus aureus* or vancomycin-resistant *Enterococcus faecium* and said cyclic peptide is cyclized by way of backbone atoms.

2. The cyclic peptide of claim 1, wherein the β-turn region is a four amino acid residue peptide segment selected from the group consisting of:

| | |
|---|---|
| ARTE | (SEQ ID NO: 1); |
| GFRE | (SEQ ID NO: 2); |
| GNRG | (SEQ ID NO: 3); |
| LPRE | (SEQ ID NO: 4); |
| RFGE | (SEQ ID NO: 5); |
| SYRE | (SEQ ID NO: 6); |
| AFLK | (SEQ ID NO: 7); |
| AGIR | (SEQ ID NO: 8); |
| APRV | (SEQ ID NO: 9); |
| FQNR | (SEQ ID NO: 10); |
| GFRS | (SEQ ID NO: 11); |
| HFGG | (SEQ ID NO: 12); |
| IFGR | (SEQ ID NO: 13); |
| IGGR | (SEQ ID NO: 14); |
| IPIR | (SEQ ID NO: 15); |
| IRGV | (SEQ ID NO: 16); |
| ISGR | (SEQ ID NO: 17); |
| IWGR | (SEQ ID NO: 18); |
| LWGR | (SEQ ID NO: 19); |
| RFPY | (SEQ ID NO: 20); |
| RFYL | (SEQ ID NO: 21); |
| RGFL | (SEQ ID NO: 22); |
| RGGI | (SEQ ID NO: 23); |
| RGWI | (SEQ ID NO: 24); |
| RGWV | (SEQ ID NO: 25); |
| RIGA | (SEQ ID NO: 26); |

| | |
|---|---|
| RIPA | (SEQ ID NO: 27); |
| RIPI | (SEQ ID NO: 28); |
| RIPV | (SEQ ID NO: 29); |
| RLVF | (SEQ ID NO: 30); |
| RTSS | (SEQ ID NO: 31); |
| TTRT | (SEQ ID NO: 32); |
| VPIR | (SEQ ID NO: 33); |
| VWGR | (SEQ ID NO: 34); |
| GPRI | (SEQ ID NO: 35); |
| GPRV | (SEQ ID NO: 36); |
| GRAV | (SEQ ID NO: 37); |
| GRPV | (SEQ ID NO: 38); |
| INRG | (SEQ ID NO: 39); |
| LLNR | (SEQ ID NO: 40); |
| LNGR | (SEQ ID NO: 41); |
| LPNR | (SEQ ID NO: 42); |
| RNGG | (SEQ ID NO: 43); |
| RNPL | (SEQ ID NO: 44); |
| YQGR | (SEQ ID NO: 45); |
| FQHR | (SEQ ID NO: 46); |
| KGRE | (SEQ ID NO: 47); |
| RARG | (SEQ ID NO: 48); |
| RRTE | (SEQ ID NO: 49); |
| IRGR | (SEQ ID NO: 50); |
| KGHL | (SEQ ID NO: 51); |
| RFHL | (SEQ ID NO: 52); |
| RKSG | (SEQ ID NO: 53); |
| RPRV | (SEQ ID NO: 54); |
| RRAL | (SEQ ID NO: 55); |
| RRFS | (SEQ ID NO: 56); |
| RRGS | (SEQ ID NO: 57); |
| RSRG | (SEQ ID NO: 58); |
| RSTR | (SEQ ID NO: 59); |
| RTGR | (SEQ ID NO: 60); |
| RTRG | (SEQ ID NO: 61); |
| YRGR | (SEQ ID NO: 62); |
| RKNG | (SEQ ID NO: 63); |
| RNKG | (SEQ ID NO: 64); |
| KRRE | (SEQ ID NO: 65); |
| RKRG | (SEQ ID NO: 66); |
| RRRF | (SEQ ID NO: 67); and |
| RRTR | (SEQ ID NO: 68). |

3. The cyclic peptide of claim 1 wherein the loop region is a three or four amino acid residue peptide sequence selected from the group consisting of:

| | |
|---|---|
| ARTE | (SEQ ID NO: 1); |
| GFRE | (SEQ ID NO: 2); |
| GNRG | (SEQ ID NO: 3); |
| LPRE | (SEQ ID NO: 4); |
| RFGE | (SEQ ID NO: 5); |
| SYRE | (SEQ ID NO: 6); |
| AFLK | (SEQ ID NO: 7); |
| AGIR | (SEQ ID NO: 8); |
| APRV | (SEQ ID NO: 9); |
| FQNR | (SEQ ID NO: 10); |
| GFRS | (SEQ ID NO: 11); |
| HFGG | (SEQ ID NO: 12); |
| IFGR | (SEQ ID NO: 13); |
| IGGR | (SEQ ID NO: 14); |
| IPIR | (SEQ ID NO: 15); |
| IRGV | (SEQ ID NO: 16); |
| ISGR | (SEQ ID NO: 17); |
| IWGR | (SEQ ID NO: 18); |
| LWGR | (SEQ ID NO: 19); |
| RFPY | (SEQ ID NO: 20); |
| RFYL | (SEQ ID NO: 21); |
| RGFL | (SEQ ID NO: 22); |
| RGGI | (SEQ ID NO: 23); |
| RGWI | (SEQ ID NO: 24); |
| RGWV | (SEQ ID NO: 25); |
| RIGA | (SEQ ID NO: 26); |
| RIPA | (SEQ ID NO: 27); |
| RIPI | (SEQ ID NO: 28); |
| RIPV | (SEQ ID NO: 29); |
| RLVF | (SEQ ID NO: 30); |
| RTSS | (SEQ ID NO: 31); |
| TTRT | (SEQ ID NO: 32); |
| VPIR | (SEQ ID NO: 33); |
| VWGR | (SEQ ID NO: 34); |
| GPRI | (SEQ ID NO: 35); |
| GPRV | (SEQ ID NO: 36); |
| GRAV | (SEQ ID NO: 37); |
| GRPV | (SEQ ID NO: 38); |
| INRG | (SEQ ID NO: 39); |
| LLNR | (SEQ ID NO: 40); |
| LNGR | (SEQ ID NO: 41); |
| LPNR | (SEQ ID NO: 42); |
| RNGG | (SEQ ID NO: 43); |
| RNPL | (SEQ ID NO: 44); |
| YQGR | (SEQ ID NO: 45); |
| FQHR | (SEQ ID NO: 46); |
| KGRE | (SEQ ID NO: 47); |
| RARG | (SEQ ID NO: 48); |
| RRTE | (SEQ ID NO: 49); |
| IRGR | (SEQ ID NO: 50); |
| KGHL | (SEQ ID NO: 51); |
| RFHL | (SEQ ID NO: 52); |
| RKSG | (SEQ ID NO: 53); |
| RPRV | (SEQ ID NO: 54); |
| RRAL | (SEQ ID NO: 55); |
| RRFS | (SEQ ID NO: 56); |
| RRGS | (SEQ ID NO: 57); |
| RSRG | (SEQ ID NO: 58); |
| RSTR | (SEQ ID NO: 59); |
| RTGR | (SEQ ID NO: 60); |
| RTRG | (SEQ ID NO: 61); |
| YRGR | (SEQ ID NO: 62); |
| RKNG | (SEQ ID NO: 63); |
| RNKG | (SEQ ID NO: 64); |
| KRRE | (SEQ ID NO: 65); |
| RKRG | (SEQ ID NO: 66); |
| RRRF | (SEQ ID NO: 67); |
| RRTR | (SEQ ID NO: 68); |
| GFGE | (SEQ ID NO: 70); |
| GSGE | (SEQ ID NO: 71); |
| IAGE | (SEQ ID NO: 72); |
| LPLE | (SEQ ID NO: 73); |
| PWSE | (SEQ ID NO: 74); |
| VSGE | (SEQ ID NO: 75); |
| YSTE | (SEQ ID NO: 76); |
| IGGV | (SEQ ID NO: 77); |
| IPIS | (SEQ ID NO: 78); |
| IWGV | (SEQ ID NO: 79); |
| VWGA | (SEQ ID NO: 80); |
| VWGI | (SEQ ID NO: 81); |
| VWGV | (SEQ ID NO: 82); |
| INGV | (SEQ ID NO: 83); |
| TNGG | (SEQ ID NO: 84); |
| VNGA | (SEQ ID NO: 85); |
| VNGV | (SEQ ID NO: 86); |
| WNMG | (SEQ ID NO: 87); |
| GPQI | (SEQ ID NO: 88); |
| VPW | (SEQ ID NO: 89); |
| VGW | (SEQ ID NO: 90); |
| LPF | (SEQ ID NO: 91); |
| RGW | (SEQ ID NO: 92); |
| WAL | (SEQ ID NO: 93); |
| VRW | (SEQ ID NO: 94); and |
| VRL | (SEQ ID NO: 95). |

4. A cyclic peptide having antimicrobiol activity against *E. coli, Pseudomonas aeruginosa*, methicillin-resistant *Staphylococcus aureus* or vancomycin-resistant *entereococcus faecium* having the formula:

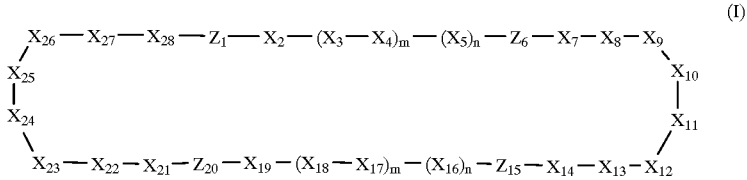

(I)

wherein m=0,1,2 and n=0,1 with the proviso that when m=2, n=0;

$X_{21}$, $X_{22}$, $X_{24}$, $x_{25}$, $X_{27}$ and $X_{28}$ are each independently present or absent;

$X_7$ and $X_{14}$ are either both present or both absent;

$X_8$ and $X_{13}$ are either both present or both absent;

$X_2$, $X_3$, $X_4$, $X_5$, $X_7$, $X_8$, $X_{13}$, $X_{14}$, $X_{16}$, $X_{17}$, $X_{18}$ $X_{19}$, $X_{20}$, $X_{22}$, $X_{27}$ and $X_{28}$ are each independently a hydrophobic amino acid, a hydrophilic amino acid or a small amino acid, with the provisos that (i) when $X_2$ is a hydrophobic amino acid $X_7$, $X_{14}$, $X_{19}$, $X_{21}$, and $X_{28}$ are each independently a hydrophobic amino acid or a small amino acid and $X_3$, $X_8$, $X_{13}$, $X_{18}$, $X_{22}$ and $X_{27}$ are each independently a hydrophilic amino acid or a small amino acid; and (ii) when $X_2$ is a hydrophilic amino acid $X_7$, $X_{14}$, $X_{19}$, $X_{21}$ and $X_{28}$ are each independently a hydrophilic amino acid or a small amino acid and $X_3$, $X_8$, $X_{13}$, $X_{18}$, $X_{22}$ and $X_{27}$ are each independently a hydrophobic amino acid or a small amino acid;

$X_{23}$, $X_{24}$, $X_{25}$ and $X_{26}$ taken together are a loop;

$Z_1$, $Z_6$, $Z_{15}$ and $Z_{20}$ are each independently a hydrophilic amino acid, a small amino acid or a cysteine-like amino acid;

$X_9$, $X_{10}$, $X_{11}$ and $X_{12}$ taken together are a β-turn;

at least one of $X_9$, $X_{10}$, $X_{11}$, $X_{12}$, $X_{23}$, $X_{24}$, $X_{25}$ or $X_{26}$ is a basic amino acid; and the peptide has a net positive charge at physiological pH.

5. The cyclic peptide of claim 4 wherein the peptide is selected from the group consisting of:

| | |
|---|---|
| cyclo(SVRGFRVRGF) | (SEQ ID NO: 100); |
| cyclo(SVR*GFSVR*GF) | (SEQ ID NO: 101); |
| cyclo(FVRSYVLRSV) | (SEQ ID NO: 102); |
| cyclo(FVPRYVLPRV) | (SEQ ID NO: 103); |
| cyclo(YVRGFVFGRV) | (SEQ ID NO: 104); |
| cyclo(CVRRYCLWRGV) | (SEQ ID NO: 105); |
| cycld(CVTRYCLWRGV) | (SEQ ID NO: 106); |
| cyclo(CVRTYCLRGW) | (SEQ ID NO: 107); |
| cyclo(CVPRYCLWRGV) | (SEQ ID NO: 108); |
| cyclo(CVRRYCLGRW) | (SEQ ID NO: 109); |
| cyclo(CVRRYCLGW) | (SEQ ID NO: 110); |
| cyclo(CVR*RYCLWRGW) | (SEQ ID NO: 111); |
| cyclo(CRRRFCYDLWRGV-Dpr-V) | (SEQ ID NO: 112); |
| cyclo(CV-Dpr-RPRFDYCLWRGV) | (SEQ ID NO: 113); |
| cyclo(CV-Dpr-RPRFDYCLPRW) | (SEQ ID NO: 114); |
| cyclo(Dpr-VDRPRF-Dpr-YDLWRGV) | (SEQ ID NO: 115); |
| cyclo(SVOGFSVOGF) | (SEQ ID NO: 116); |
| cyclo(FVGOYVLGOV) | (SEQ ID NO: 117); |
| cyclo(FVGOYVWPOV) | (SEQ ID NO: 118); |
| cyclo(YVRGFVFGOV) | (SEQ ID NO: 119); |
| cyclo(YVOGFVFOGV) | (SEQ ID NO: 120); |
| cyclo(CYSOYCLWOGV) | (SEQ ID NO: 121); |
| cyclo(CVPOYCLWOGV) | (SEQ ID NO: 122); |
| cyclo(CVOOYCLWOGF) | (SEQ ID NO: 123); |
| cyclo(SVKGFKVKGF) | (SEQ ID NO: 124); |
| cyclo(FVGKYVLGKV) | (SEQ ID NO: 125); |
| cyclo(FVGKYVWPKV) | (SEQ ID NO: 126); |
| cyclo(YVKGFVFGKV) | (SEQ ID NO: 127); |

-continued

| | |
|---|---|
| cyclo(YAKGFVFGKV) | (SEQ ID NO: 128); |
| cyclo(CVKKYCLWKGV) | (SEQ ID NO: 129); |
| cyclo(CVSKYCLWKGV) | (SEQ ID NO: 130); |
| cyclo(CVSKYCLGW) | (SEQ ID NO: 131); |
| cyclo(CVPKYCLKGW) | (SEQ ID NO: 132); |
| cyclo(CGFRSCVGRWL) | (SEQ ID NO: 133); |
| cyclo(CIRGVCLWKGY) | (SEQ ID NO: 134); |
| cyclo(CGFRSCVGRW) | (SEQ ID NO: 135); and |
| cyclo(CRGVCWRGY) | (SEQ ID NO: 136). |

6. The cyclic peptide of claim 4 having the formula:

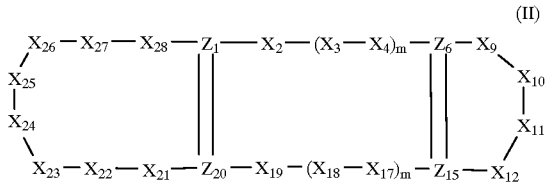

(II)

wherein m=2;

‖ designates a disulfide linkage;

$X_{21}$, $X_{22}$, $X_{24}$, $X_{25}$, $X_{27}$ and $X_{28}$ are each independently present or absent;

$X_2$ is a hydrophobic amino acid;

$X_3$, $X_{18}$, $X_{22}$ and $X_{27}$ are each independently a hydrophilic amino acid or a small amino acid;

$X_4$, $X_{17}$, $X_{19}$, $X_{21}$ and $X_{28}$ are each independently a hydrophobic amino acid or a small amino acid;

$X_{23}$, $X_{24}$, $X_{25}$ and $X_{26}$ taken together are a loop;

$Z_1$, $Z_6$, $Z_{15}$ and $Z_{20}$ are each cysteine, homocysteine or penicillamine;

$x_9$, $X_{10}$, $X_{11}$ and $X_{12}$ taken together are a β-turn;

at least one of $X_9$, $X_{10}$, $X_{11}$, $X_{12}$, $X_{23}$, $X_{24}$, $X_{25}$ or $X_{26}$ is a basic amino acid; and the peptide has a net positive charge at physiological pH.

7. The cyclic peptide of claim 4 having the formula:

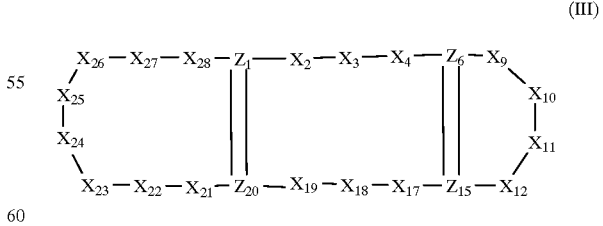

(III)

wherein ‖ designates a disulfide linkage;

$X_{21}$, $X_{22}$, $X_{24}$, $X_{25}$, $X_{27}$ and $X_{28}$ are each independently present or absent;

$X_2$ is a hydrophobic amino acid;

$X_3$, $X_{18}$, $X_{22}$ and $X_{27}$ are each independently a hydrophilic amino acid or a small amino acid;

$X_4$, $X_{17}$, $X_{19}$, $X_{21}$ and $X_{28}$ are each independently a hydrophobic amino acid or a small amino acid;

$X_{23}$, $X_{24}$, $X_{25}$ and $X_{26}$ taken together are a loop;

$Z_1$, $Z_6$, $Z_{15}$ and $Z_{20}$ are each cysteine, homocysteine or penicillamine;

$X_9$, $X_{10}$, $X_{11}$ and $X_{12}$ taken together are a β-turn;

at least one of $X_9$, $X_{10}$, $X_{11}$, $X_{12}$, $X_{23}$, $X_{24}$, $X_{25}$ or $X_{26}$ is a basic amino acid; and the peptide has a net positive charge at physiological pH.

8. The cyclic peptide of claim 7 wherein the peptide is selected from the group consisting of:

| | |
|---|---|
| cyclo(CLRYCRRRFCVRFCLWF) | (SEQ ID NO: 140); |
| cyclo(CLRYCRR*FCVRFCLWF) | (SEQ ID NO: 141); |
| cyclo(CLRYCRPFCVSYCVRWF) | (SEQ ID NO: 142); |
| cyclo(CLRYCRIPICVRFCVPRW) | (SEQ ID NO: 143); |
| cyclo(CLRYCRF*PFCVRFCLSRW) | (SEQ ID NO: 144); |
| cyclo(CL-Dpr-YCRRRFCVDYCVRGW) | (SEQ ID NO: 145); |
| cyclo(CL-Dpr-YCVRRFCVDYCVGW) | (SEQ ID NO: 146); and |
| cyclo(CL-Dpr-YCRSRFCVDYCVGW) | (SEQ ID NO: 147). |

9. The cyclic peptide of claim 4 having the structure:

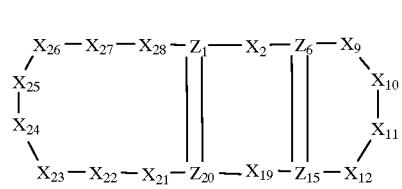

(IV)

wherein ‖ designates a disulfide linkage;

$X_{21}$, $X_{22}$, $X_{24}$, $X_{25}$, $X_{27}$ and $X_{28}$ are each independently present or absent;

$X_2$ is a hydrophobic amino acid;

$X_{22}$ and $X_{27}$ are each independently a hydrophilic amino acid or a small amino acid;

$X_{19}$, $X_{21}$ and $X_{28}$ are each independently a hydrophobic amino acid or a small amino acid;

$X_{23}$, $X_{24}$, $X_{25}$ and $X_{26}$ taken together are a loop;

$Z_1$, $Z_6$, $Z_{15}$ and $Z_{20}$ are each independently cysteine, homocysteine or penicillamine;

$X_9$, $X_{10}$, $X_{11}$ and $X_{12}$ taken together are a β-turn;

at least one of $X_9$, $X_{10}$, $X_{11}$, $X_{12}$, $X_{23}$, $X_{24}$, $X_{25}$ or $X_{26}$ is a basic amino acid; and the peptide has a net positive charge at physiological pH.

10. The cyclic peptide of claim 9 wherein the peptide is selected from the group consisting of:

| | |
|---|---|
| cyclo(CYCRRRFCVCVL) | (SEQ ID NO: 150); |
| cyclo(CYCRRRFCVCVWY) | (SEQ ID NO: 151); |
| cyclo(CYCRGRFCVRW) | (SEQ ID NO: 152); |
| cyclo(CVCFR*R*RCYCLWV) | (SEQ ID NO: 153); |
| cyclo(CYCRRRFCVCVRL) | (SEQ ID NO: 154); |
| cyclo(CVCFR*R*RCYCLRV) | (SEQ ID NO: 155); |
| cyclo(CYCRRRFCVCIFGR) | (SEQ ID NO: 156); |
| cyclo(CYCRRRFCVCISGR) | (SEQ ID NO: 157); |
| cyclo(CYCRRRFCVCIRGV) | (SEQ ID NO: 158); |
| cyclo(CYCRRRFCVCIWGR) | (SEQ ID NO: 159); |
| cyclo(CYCRRRFCVCRFPY) | (SEQ ID NO: 160); |
| cyclo(CYCRRRFCVCRGFL) | (SEQ ID NO: 161); |
| cyclo(CYCRRRFCVCRGWV) | (SEQ ID NO: 162); |
| cyclo(CYCRRRFCVCRGWI) | (SEQ ID NO: 163); |
| cyclo(CYCRRRFCVCRIPA) | (SEQ ID NO: 164); |
| cyclo(CYCRRRFCVCYRGR) | (SEQ ID NO: 165); |

-continued

| | |
|---|---|
| cyclo(CYCRRRFCVCRLVF) | (SEQ ID NO: 166); |
| cyclo(CYCRRRFCVCVR-Cha) | (SEQ ID NO: 167); |
| cyclo(CYCRPRFCVCVR-Cha) | (SEQ ID NO: 168); |
| cyclo(CYCFRRFCVCVR-Cha) | (SEQ ID NO: 169); |
| cyclo(CYCRRRFCVCVRG-Cha) | (SEQ ID NO: 170); |
| cyclo(CYCRRRFCVCVRW) | (SEQ ID NO: 171); |
| cyclo(CYCRPRFCVCVRW) | (SEQ ID NO: 172); |
| cyclo(CYCRSRFCVCVR-Cha) | (SEQ ID NO: 173); |
| cyclo(CYCVRRFCVCVRW) | (SEQ ID NO: 174); |
| cyclo(CFCVOOFCVCFOV) | (SEQ ID NO: 175); |
| cyclo(CFCVOOYCVCVOW) | (SEQ ID NO: 176); |
| cyclo(CFCOPO*YCVCVO-Cha) | (SEQ ID NO: 177); |
| cyclo(CFCVOTYCVCVO-Cha) | (SEQ ID NO: 178); |
| cyclo(CFCV-MeGly-O*YCVCYOV) | (SEQ ID NO: 179); |
| cyclo(CYCOO*OFCVCVOWL) | (SEQ ID NO: 180); |
| cyclo(CYCOOOFCVCVOWL) | (SEQ ID NO: 181); |
| cyclo(CYCRGRFCVCVGRWL) | (SEQ ID NO: 182); |
| cyclo(CVCFR*R*RCYCLWRGV) | (SEQ ID NO: 183); |
| cyclo(CVCFR*R*RCYCLWGRV) | (SEQ ID NO: 184); |
| cyclo(CYCRRRFCVCVGRWL) (all D) | (SEQ ID NO: 185); |
| cyclo(CYCRPRFCVCVGRWL) | (SEQ ID NO: 186); |
| cyclo(CVCFRPRCYCLWRGV) | (SEQ ID NO: 187); |
| cyclo(CVCFPRRCYCLWRGV) | (SEQ ID NO: 188); |
| cyclo(CVCVGPRCYCLRGW) | (SEQ ID NO: 189); |
| cyclo(CYCRRRFCVCVRWL) | (SEQ ID NO: 190); |
| cyclo(CYCRRRFCVCVRGW) | (SEQ ID NO: 191); |
| cyclo(CYCRRRFCVCWRGV) | (SEQ ID NO: 192); |
| cyclo(CYCRPRFCVCWGRV) | (SEQ ID NO: 193); |
| cyclo(CYCRRRFCVCVRGW) | (SEQ ID NO: 194); |
| cyclo(CVCRPRWCYCLWSV) | (SEQ ID NO: 195); |
| cyclo(CYCRRRFCVCVGRWL) | (SEQ ID NO: 196); |
| cyclo(CYCRR*RFCVCVGRWL) | (SEQ ID NO: 197); |
| cyclo(CYCSRRYCVCYPRV) | (SEQ ID NO: 198); |
| cyclo(CYCVRRYCVCYGRWV) | (SEQ ID NO: 199); |
| cyclo(CYCGR*RYCVCYARWV) | (SEQ ID NO: 200); |
| cyclo(CVCRSRFCYCLWRGV) | (SEQ ID NO: 201); |
| cyclo(CVCRPRFCYCLWRGV) | (SEQ ID NO: 202); |
| cyclo(CVCYRFRCYCVWRGF) | (SEQ ID NO: 203); |
| cyclo(CYCRPRFCVCVGRPGWL) | (SEQ ID NO: 204); |
| cyclo(CYCRPRFCVCVGRGWL) | (SEQ ID NO: 205); |
| cyclo(CYCRGRFCVCVRGGRV) | (SEQ ID NO: 206); |
| cyclo(CVCVRRYCVCFGWARV) | (SEQ ID NO: 207); |
| cyclo(CYCRPRFCVCVGRRGWL) | (SEQ ID NO: 208); |
| cyclo(CYCRPRFCVCVGRRGGL) | (SEQ ID NO: 209); |
| cyclo(CYCRRRFCVCVGRRGGRL) | (SEQ ID NO: 210); |
| cyclo(CYCRGRFCVCVGRGGWRL) | (SEQ ID NO: 211); |
| cyclo(CYCRGRFCVCVGRRGLR-Cha) | (SEQ ID NO: 212); |
| cyclo(CYCRGRFCVCVGRRGWRL) | (SEQ ID NO: 213); |
| cyclo(CYCRPRFCVCVGRGRWRL) | (SEQ ID NO: 214); |
| cyclo(CYCRTRFCVCVGRRGWRL) | (SEQ ID NO: 215); |
| cyclo(CFCVRRFCVCFRV) | (SEQ ID NO: 216); |
| cyclo(CFCRPRYCVCVR-Cha) | (SEQ ID NO: 217); |
| cyclo(CFCRF*PYCVCVR-Cha) | (SEQ ID NO: 218); |
| cyclo(CFCVTRYCVCVR-Cha) | (SEQ ID NO: 219); |
| cyclo(CFCV-MeGly-R*YCVCYRV) | (SEQ ID NO: 220); |
| cyclo(CYCRR*RFCVCVRWL) | (SEQ ID NO: 221); |
| cyclo(CYCRRRFCVCVRWL) | (SEQ ID NO: 222); |
| cyclo(CYCVRRYCVCYRWV) | (SEQ ID NO: 223); |
| cyclo(CYCKKKFCVCVL) | (SEQ ID NO: 224); |
| cyclo(CYCKKKFCVCVWY) | (SEQ ID NO: 225); |
| cyclo(CYCKKKFCVCVWL) | (SEQ ID NO: 226); |
| cyclo(CYCKKKFCVCVKL) | (SEQ ID NO: 227); |
| cyclo(CFCKPFCVCVK-Cha) | (SEQ ID NO: 228); |
| cyclo(CYCRRRFCVCVL) | (SEQ ID NO: 229); and |
| cyclo(CYCRGRFCVCVGRGGWRL) | (SEQ ID NO: 230). |

11. A cyclic peptide having antimicrobial activity against *E. coli*, *Pseudomonas aeruginosa*, methicillin-resistant *Staphylococcus aureus* or vancomycin-resistant *Enterococcus faecium* and having the formula:

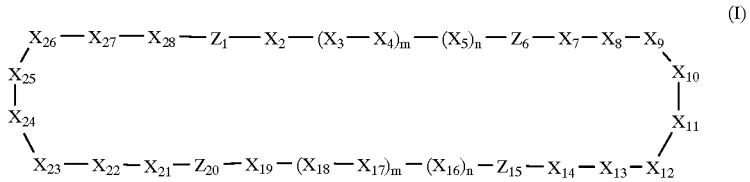

(I)

wherein m=0,1,2 and n=0,1 with the proviso that when m=2, n=0;

- $X_{21}$, $X_{22}$, $X_{24}$, $X_{25}$, $X_{27}$ and $X_{28}$ are each independently present or absent;
- $X_7$ and $X_{14}$ are either both present or both absent;
- $X_8$ and $X_{13}$ are either both present or both absent;
- $X_2$, $X_3$, $X_4$, $X_5$, $X_7$, $X_8$, $X_{13}$, $X_{14}$, $X_{16}$, $X_{17}$, $X_{18}$, $X_{19}$, $X_{21}$, $X_{22}$, $X_{27}$ and $X_{28}$ are each independently a hydrophobic amino acid, a hydrophilic amino acid or a small amino acid, with the provisos that (i) when $X_2$ is a hydrophobic amino acid $X_7$, $X_{14}$, $X_{19}$, $X_{21}$ and $X_{28}$ are each independently a hydrophobic amino acid or a small amino acid and $X_3$, $X_8$, $X_{13}$, $X_{18}$, $X_{22}$ and $X_{27}$ are each independently a hydrophilic amino acid or a small amino acid; and (ii) when $X_2$ is a hydrophilic amino acid $X_7$, $X_{14}$, $X_{19}$, $X_{21}$ and $X_{28}$ are each independently a hydrophilic amino acid or a small amino acid and $X_3$, $X_8$, $X_{13}$, $X_{18}$, $X_{22}$ and $X_{27}$ are each independently a hydrophobic amino acid or a small amino acid;
- $X_{23}$, $X_{24}$, $X_{25}$ and $X_{26}$ taken together are a peptide loop;
- $Z_1$, $Z_6$, $Z_{15}$ and $Z_{20}$ are each independently a hydrophilic amino acid, a small amino acid or a cysteine-like amino acid;
- $X_9$, $X_{10}$, $X_{11}$, and $X_{12}$ taken together are a peptide β-turn;
- at least one of $X_9$, $X_{10}$, $X_{11}$, $X_{12}$, $X_{23}$, $X_{24}$, $X_{25}$ or $X_{26}$ is a basic amino acid; and wherein the peptide has a net positive charge at physiological pH.

12. A cyclic peptide having antimicrobial activity against *E. coli*, *Pseudomonas aeruginosa*, methicillin-resistant *Staphylococcus aureus* or vancomycin-resistant *Entereococcus faecium* comprising:

- an amphiphilic anti-parallel β-sheet composed of first and second anti-parallel strands, each strand containing 3 to 11 amino acid residues and having an N-terminus and a C-terminus;
- a first means for covalently linking the N-terminus of the first strand to the C-terminus of the second strand; and
- a second means for covalently linking the C-terminus of the first strand to the N-terminus of the second strand.

13. The cyclic peptide of claim 12, wherein said first means is a loop and said second means is a β-turn.

14. The cyclic peptide of claim 13, wherein said loop is a peptide loop and said β-turn is a peptide β-turn.

15. A composition comprising a cyclic peptide according to claim 1 in admixture with a carrier or excipient.

16. A method of inhibiting the growth of a microbe, the method comprising the step of contacting a microbe with an antimicrobially effective amount of a cyclic peptide according to claim 1.

17. A method of treating a microbial infection, the method comprising the step of administering to a subject in need thereof an effective amount of a compound according to claim 1.

18. The method of claim 17, wherein the infection is caused by vancomycin-resistant *Enterococcus faecium*, methicillin-resistant *Staphylococcus aureus*, penicillin-resistant *Streptococcus pneumoniae* or *Pseudomonas aeruginosa*.

\* \* \* \* \*

```
SEQUENCE LISTING (1) GENERAL INFORMATION:

(iii) NUMBER OF SEQUENCES: 222

(2) INFORMATION FOR SEQ ID NO:1:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:1:

Ala Arg Thr Glu
1

(2) INFORMATION FOR SEQ ID NO:2:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:2:

Gly Phe Arg Glu
1
```

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:3:

Gly Asn Arg Gly
1

(2) INFORMATION FOR SEQ ID NO:4:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:4:

Leu Pro Arg Glu
1

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:5:

Arg Phe Gly Glu
1

(2) INFORMATION FOR SEQ ID NO:6:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:6:

-continued

```
Ser Tyr Arg Glu
1

(2) INFORMATION FOR SEQ ID NO:7:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:7:

Ala Phe Leu Lys
1

(2) INFORMATION FOR SEQ ID NO:8:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:8:

Ala Gly Ile Arg
1

(2) INFORMATION FOR SEQ ID NO:9:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:9:

Ala Pro Arg Val
1

(2) INFORMATION FOR SEQ ID NO:10:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
```

(D) OTHER INFORMATION: /product= "Beta-turn"

(xi) SEQUENCE DESCRIPTION: SEQ ID NO:10:

Phe Gln Asn Arg
1

(2) INFORMATION FOR SEQ ID NO:11:

(i) SEQUENCE CHARACTERISTICS:
            (A) LENGTH: 4 amino acids
            (B) TYPE: amino acid
            (C) STRANDEDNESS: unknown
            (D) TOPOLOGY: Not Relevant (ii) MOLECULE TYPE: peptide (ix) FEATURE:
            (A) NAME/KEY: Peptide
            (B) LOCATION: 1..4
            (D) OTHER INFORMATION: /product= "Beta-turn"

(xi) SEQUENCE DESCRIPTION: SEQ ID NO:11:

Gly Phe Arg Ser
1

(2) INFORMATION FOR SEQ ID NO:12:

(i) SEQUENCE CHARACTERISTICS:
            (A) LENGTH: 4 amino acids
            (B) TYPE: amino acid
            (C) STRANDEDNESS: unknown
            (D) TOPOLOGY: Not Relevant (ii) MOLECULE TYPE: peptide (ix) FEATURE:
            (A) NAME/KEY: Peptide
            (B) LOCATION: 1..4
            (D) OTHER INFORMATION: /product= "Beta-turn"

(xi) SEQUENCE DESCRIPTION: SEQ ID NO:12:

His Phe Gly Gly
1

(2) INFORMATION FOR SEQ ID NO:13:

(i) SEQUENCE CHARACTERISTICS:
            (A) LENGTH: 4 amino acids
            (B) TYPE: amino acid
            (C) STRANDEDNESS: unknown
            (D) TOPOLOGY: Not Relevant (ii) MOLECULE TYPE: peptide (ix) FEATURE:
            (A) NAME/KEY: Peptide
            (B) LOCATION: 1..4
            (D) OTHER INFORMATION: /product= "Beta-turn"

(xi) SEQUENCE DESCRIPTION: SEQ ID NO:13:

Ile Phe Gly Arg
1

(2) INFORMATION FOR SEQ ID NO:14:

(i) SEQUENCE CHARACTERISTICS:
            (A) LENGTH: 4 amino acids
            (B) TYPE: amino acid
            (C) STRANDEDNESS: unknown
            (D) TOPOLOGY: Not Relevant (ii) MOLECULE TYPE: peptide (ix) FEATURE:
    (A) NAME/KEY: Peptide
    (B) LOCATION: 1..4
    (D) OTHER INFORMATION: /product= "Beta-turn"

(xi) SEQUENCE DESCRIPTION: SEQ ID NO:14:

Ile Gly Gly Arg
1

(2) INFORMATION FOR SEQ ID NO:15:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:15:

Ile Pro Ile Arg
1

(2) INFORMATION FOR SEQ ID NO:16:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:16:

Ile Arg Gly Val
1

(2) INFORMATION FOR SEQ ID NO:17:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:17:

Ile Ser Gly Arg
1

(2) INFORMATION FOR SEQ ID NO:18:

(i) SEQUENCE CHARACTERISTICS:
        (A) LENGTH: 4 amino acids
        (B) TYPE: amino acid (C) STRANDEDNESS: unknown
            (D) TOPOLOGY: Not Relevant (ii) MOLECULE TYPE: peptide (ix) FEATURE:
            (A) NAME/KEY: Peptide
            (B) LOCATION: 1..4
            (D) OTHER INFORMATION: /product= "Beta-turn"

(xi) SEQUENCE DESCRIPTION: SEQ ID NO:18:

Ile Trp Gly Arg
1

(2) INFORMATION FOR SEQ ID NO:19:

(i) SEQUENCE CHARACTERISTICS:
            (A) LENGTH: 4 amino acids
            (B) TYPE: amino acid
            (C) STRANDEDNESS: unknown
            (D) TOPOLOGY: Not Relevant (ii) MOLECULE TYPE: peptide (ix) FEATURE:
            (A) NAME/KEY: Peptide
            (B) LOCATION: 1..4
            (D) OTHER INFORMATION: /product= "Beta-turn"

(xi) SEQUENCE DESCRIPTION: SEQ ID NO:19:

Leu Trp Gly Arg
1

(2) INFORMATION FOR SEQ ID NO:20:

(i) SEQUENCE CHARACTERISTICS:
            (A) LENGTH: 4 amino acids
            (B) TYPE: amino acid
            (C) STRANDEDNESS: unknown
            (D) TOPOLOGY: Not Relevant (ii) MOLECULE TYPE: peptide (ix) FEATURE:
            (A) NAME/KEY: Peptide
            (B) LOCATION: 1..4
            (D) OTHER INFORMATION: /product= "Beta-turn"

(xi) SEQUENCE DESCRIPTION: SEQ ID NO:20:

Arg Phe Pro Tyr
1

(2) INFORMATION FOR SEQ ID NO:21:

(i) SEQUENCE CHARACTERISTICS:
            (A) LENGTH: 4 amino acids
            (B) TYPE: amino acid
            (C) STRANDEDNESS: unknown
            (D) TOPOLOGY: Not Relevant (ii) MOLECULE TYPE: peptide (ix) FEATURE:
            (A) NAME/KEY: Peptide
            (B) LOCATION: 1..4
            (D) OTHER INFORMATION: /product= "Beta-turn"

(xi) SEQUENCE DESCRIPTION: SEQ ID NO:21:

Arg Phe Tyr Leu
1

(2) INFORMATION FOR SEQ ID NO:22:

(i) SEQUENCE CHARACTERISTICS:
    (A) LENGTH: 4 amino acids
    (B) TYPE: amino acid
    (C) STRANDEDNESS: unknown
    (D) TOPOLOGY: Not Relevant (ii) MOLECULE TYPE: peptide (ix) FEATURE:
    (A) NAME/KEY: Peptide
    (B) LOCATION: 1..4
    (D) OTHER INFORMATION: /product= "Beta-turn"

(xi) SEQUENCE DESCRIPTION: SEQ ID NO:22:

Arg Gly Phe Leu
1

(2) INFORMATION FOR SEQ ID NO:23:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:23:

Arg Gly Gly Ile
1

(2) INFORMATION FOR SEQ ID NO:24:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:24:

Arg Gly Trp Ile
1

(2) INFORMATION FOR SEQ ID NO:25:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:25:

Arg Gly Trp Val

-continued (2) INFORMATION FOR SEQ ID NO:26:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:26:

Arg Ile Gly Ala
1

(2) INFORMATION FOR SEQ ID NO:27:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:27:

Arg Ile Pro Ala
1

(2) INFORMATION FOR SEQ ID NO:28:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:28:

Arg Ile Pro Ile
1

(2) INFORMATION FOR SEQ ID NO:29:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:29:

Arg Ile Pro Val
1

(2) INFORMATION FOR SEQ ID NO:30:

(i) SEQUENCE CHARACTERISTICS:
            (A) LENGTH: 4 amino acids
            (B) TYPE: amino acid
            (C) STRANDEDNESS: unknown
            (D) TOPOLOGY: Not Relevant (ii) MOLECULE TYPE: peptide (ix) FEATURE:
            (A) NAME/KEY: Peptide
            (B) LOCATION: 1..4
            (D) OTHER INFORMATION: /product= "Beta-turn"

(xi) SEQUENCE DESCRIPTION: SEQ ID NO:30:

Arg Leu Val Phe
1

(2) INFORMATION FOR SEQ ID NO:31:

(i) SEQUENCE CHARACTERISTICS:
            (A) LENGTH: 4 amino acids
            (B) TYPE: amino acid
            (C) STRANDEDNESS: unknown
            (D) TOPOLOGY: Not Relevant (ii) MOLECULE TYPE: peptide (ix) FEATURE:
            (A) NAME/KEY: Peptide
            (B) LOCATION: 1..4
            (D) OTHER INFORMATION: /product= "Beta-turn"

(xi) SEQUENCE DESCRIPTION: SEQ ID NO:31:

Arg Thr Ser Ser
1

(2) INFORMATION FOR SEQ ID NO:32:

(i) SEQUENCE CHARACTERISTICS:
            (A) LENGTH: 4 amino acids
            (B) TYPE: amino acid
            (C) STRANDEDNESS: unknown
            (D) TOPOLOGY: Not Relevant (ii) MOLECULE TYPE: peptide (ix) FEATURE:
            (A) NAME/KEY: Peptide
            (B) LOCATION: 1..4
            (D) OTHER INFORMATION: /product= "Beta-turn"

(xi) SEQUENCE DESCRIPTION: SEQ ID NO:32:

Thr Thr Arg Thr
1

(2) INFORMATION FOR SEQ ID NO:33:

(i) SEQUENCE CHARACTERISTICS:
            (A) LENGTH: 4 amino acids
            (B) TYPE: amino acid
            (C) STRANDEDNESS: unknown
            (D) TOPOLOGY: Not Relevant (ii) MOLECULE TYPE: peptide (ix) FEATURE:
              (A) NAME/KEY: Peptide
              (B) LOCATION: 1..4
              (D) OTHER INFORMATION: /product= "Beta-turn"

(xi) SEQUENCE DESCRIPTION: SEQ ID NO:33:

Val Pro Ile Arg
1

(2) INFORMATION FOR SEQ ID NO:34:

(i) SEQUENCE CHARACTERISTICS:
              (A) LENGTH: 4 amino acids
              (B) TYPE: amino acid
              (C) STRANDEDNESS: unknown
              (D) TOPOLOGY: Not Relevant (ii) MOLECULE TYPE: peptide (ix) FEATURE:
              (A) NAME/KEY: Peptide
              (B) LOCATION: 1..4
              (D) OTHER INFORMATION: /product= "Beta-turn"

(xi) SEQUENCE DESCRIPTION: SEQ ID NO:34:

Val Trp Gly Arg
1

(2) INFORMATION FOR SEQ ID NO:35:

(i) SEQUENCE CHARACTERISTICS:
              (A) LENGTH: 4 amino acids
              (B) TYPE: amino acid
              (C) STRANDEDNESS: unknown
              (D) TOPOLOGY: Not Relevant (ii) MOLECULE TYPE: peptide (ix) FEATURE:
              (A) NAME/KEY: Peptide
              (B) LOCATION: 1..4
              (D) OTHER INFORMATION: /product= "Beta-turn"

(xi) SEQUENCE DESCRIPTION: SEQ ID NO:35:

Gly Pro Arg Ile
1

(2) INFORMATION FOR SEQ ID NO:36:

(i) SEQUENCE CHARACTERISTICS:
              (A) LENGTH: 4 amino acids
              (B) TYPE: amino acid
              (C) STRANDEDNESS: unknown
              (D) TOPOLOGY: Not Relevant (ii) MOLECULE TYPE: peptide (ix) FEATURE:
              (A) NAME/KEY: Peptide
              (B) LOCATION: 1..4
              (D) OTHER INFORMATION: /product= "Beta-turn"

(xi) SEQUENCE DESCRIPTION: SEQ ID NO:36:

Gly Pro Arg Val
1

(2) INFORMATION FOR SEQ ID NO:37:

(i) SEQUENCE CHARACTERISTICS:
              (A) LENGTH: 4 amino acids
              (B) TYPE: amino acid
              (C) STRANDEDNESS: unknown (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:37:

Gly Arg Ala Val
1

(2) INFORMATION FOR SEQ ID NO:38:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:38:

Gly Arg Pro Val
1

(2) INFORMATION FOR SEQ ID NO:39:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:39:

Ile Asn Arg Gly
1

(2) INFORMATION FOR SEQ ID NO:40:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:40:

Leu Leu Asn Arg
1

(2) INFORMATION FOR SEQ ID NO:41:

```
    (i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:41:

Leu Asn Gly Arg
 1

(2) INFORMATION FOR SEQ ID NO:42:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:42:

Leu Pro Asn Arg
 1

(2) INFORMATION FOR SEQ ID NO:43:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:43:

Arg Asn Gly Gly
 1

(2) INFORMATION FOR SEQ ID NO:44:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:44:

Arg Asn Pro Leu
 1
```

(2) INFORMATION FOR SEQ ID NO:45:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:45:

Tyr Gln Gly Arg
1

(2) INFORMATION FOR SEQ ID NO:46:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:46:

Phe Gln His Arg
1

(2) INFORMATION FOR SEQ ID NO:47:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:47:

Lys Gly Arg Glu
1

(2) INFORMATION FOR SEQ ID NO:48:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:48:

Arg Ala Arg Gly
1

(2) INFORMATION FOR SEQ ID NO:49:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:49:

Arg Arg Thr Glu
1

(2) INFORMATION FOR SEQ ID NO:50:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:50:

Ile Arg Gly Arg
1

(2) INFORMATION FOR SEQ ID NO:51:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:51:

Lys Gly His Leu
1

(2) INFORMATION FOR SEQ ID NO:52:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:

```
        (A) NAME/KEY: Peptide
        (B) LOCATION: 1..4
        (D) OTHER INFORMATION: /product= "Beta-turn"

(xi) SEQUENCE DESCRIPTION: SEQ ID NO:52:

Arg Phe His Leu
1

(2) INFORMATION FOR SEQ ID NO:53:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:53:

Arg Lys Ser Gly
1

(2) INFORMATION FOR SEQ ID NO:54:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:54:

Arg Pro Arg Val
1

(2) INFORMATION FOR SEQ ID NO:55:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:55:

Arg Arg Ala Leu
1

(2) INFORMATION FOR SEQ ID NO:56:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant
```

(ii) MOLECULE TYPE: peptide (ix) FEATURE:
             (A) NAME/KEY: Peptide
             (B) LOCATION: 1..4
             (D) OTHER INFORMATION: /product= "Beta-turn"

(xi) SEQUENCE DESCRIPTION: SEQ ID NO:56:

Arg Arg Phe Ser
1

(2) INFORMATION FOR SEQ ID NO:57:

(i) SEQUENCE CHARACTERISTICS:
             (A) LENGTH: 4 amino acids
             (B) TYPE: amino acid
             (C) STRANDEDNESS: unknown
             (D) TOPOLOGY: Not Relevant (ii) MOLECULE TYPE: peptide (ix) FEATURE:
             (A) NAME/KEY: Peptide
             (B) LOCATION: 1..4
             (D) OTHER INFORMATION: /product= "Beta-turn"

(xi) SEQUENCE DESCRIPTION: SEQ ID NO:57:

Arg Arg Gly Ser
1

(2) INFORMATION FOR SEQ ID NO:58:

(i) SEQUENCE CHARACTERISTICS:
             (A) LENGTH: 4 amino acids
             (B) TYPE: amino acid
             (C) STRANDEDNESS: unknown
             (D) TOPOLOGY: Not Relevant (ii) MOLECULE TYPE: peptide (ix) FEATURE:
             (A) NAME/KEY: Peptide
             (B) LOCATION: 1..4
             (D) OTHER INFORMATION: /product= "Beta-turn"

(xi) SEQUENCE DESCRIPTION: SEQ ID NO:58:

Arg Ser Arg Gly
1

(2) INFORMATION FOR SEQ ID NO:59:

(i) SEQUENCE CHARACTERISTICS:
             (A) LENGTH: 4 amino acids
             (B) TYPE: amino acid
             (C) STRANDEDNESS: unknown
             (D) TOPOLOGY: Not Relevant (ii) MOLECULE TYPE: peptide (ix) FEATURE:
             (A) NAME/KEY: Peptide
             (B) LOCATION: 1..4
             (D) OTHER INFORMATION: /product= "Beta-turn"

(xi) SEQUENCE DESCRIPTION: SEQ ID NO:59:

Arg Ser Thr Arg
1

(2) INFORMATION FOR SEQ ID NO:60:

(i) SEQUENCE CHARACTERISTICS:

(A) LENGTH: 4 amino acids
            (B) TYPE: amino acid
            (C) STRANDEDNESS: unknown
            (D) TOPOLOGY: Not Relevant (ii) MOLECULE TYPE: peptide (ix) FEATURE:
            (A) NAME/KEY: Peptide
            (B) LOCATION: 1..4
            (D) OTHER INFORMATION: /product= "Beta-turn"

(xi) SEQUENCE DESCRIPTION: SEQ ID NO:60:

Arg Thr Gly Arg
1

(2) INFORMATION FOR SEQ ID NO:61:

(i) SEQUENCE CHARACTERISTICS:
            (A) LENGTH: 4 amino acids
            (B) TYPE: amino acid
            (C) STRANDEDNESS: unknown
            (D) TOPOLOGY: Not Relevant (ii) MOLECULE TYPE: peptide (ix) FEATURE:
            (A) NAME/KEY: Peptide
            (B) LOCATION: 1..4
            (D) OTHER INFORMATION: /product= "Beta-turn"

(xi) SEQUENCE DESCRIPTION: SEQ ID NO:61:

Arg Thr Arg Gly
1

(2) INFORMATION FOR SEQ ID NO:62:

(i) SEQUENCE CHARACTERISTICS:
            (A) LENGTH: 4 amino acids
            (B) TYPE: amino acid
            (C) STRANDEDNESS: unknown
            (D) TOPOLOGY: Not Relevant (ii) MOLECULE TYPE: peptide (ix) FEATURE:
            (A) NAME/KEY: Peptide
            (B) LOCATION: 1..4
            (D) OTHER INFORMATION: /product= "Beta-turn"

(xi) SEQUENCE DESCRIPTION: SEQ ID NO:62:

Tyr Arg Gly Arg
1

(2) INFORMATION FOR SEQ ID NO:63:

(i) SEQUENCE CHARACTERISTICS:
            (A) LENGTH: 4 amino acids
            (B) TYPE: amino acid
            (C) STRANDEDNESS: unknown
            (D) TOPOLOGY: Not Relevant (ii) MOLECULE TYPE: peptide (ix) FEATURE:
            (A) NAME/KEY: Peptide
            (B) LOCATION: 1..4
            (D) OTHER INFORMATION: /product= "Beta-turn"

(xi) SEQUENCE DESCRIPTION: SEQ ID NO:63:

Arg Lys Asn Gly
1

(2) INFORMATION FOR SEQ ID NO:64:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:64:

Arg Asn Lys Gly
1

(2) INFORMATION FOR SEQ ID NO:65:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:65:

Lys Arg Arg Glu
1

(2) INFORMATION FOR SEQ ID NO:66:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:66:

Arg Lys Arg Gly
1

(2) INFORMATION FOR SEQ ID NO:67:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:67:

Arg Arg Arg Phe
1

(2) INFORMATION FOR SEQ ID NO:68:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (ix) FEATURE:
        (A) NAME/KEY: Peptide
        (B) LOCATION: 1..4
        (D) OTHER INFORMATION: /product= "Beta-turn"

(xi) SEQUENCE DESCRIPTION: SEQ ID NO:68:

Arg Arg Thr Arg
1

(2) INFORMATION FOR SEQ ID NO:69:

(i) SEQUENCE CHARACTERISTICS:

(xi) SEQUENCE DESCRIPTION: SEQ ID NO:69:

This sequence has been intentionally skipped (2) INFORMATION FOR SEQ ID NO:70:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:70:

Gly Phe Gly Glu
1

(2) INFORMATION FOR SEQ ID NO:71:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:71:

Gly Ser Gly Glu
1

(2) INFORMATION FOR SEQ ID NO:72:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:72:

Ile Ala Gly Glu (2) INFORMATION FOR SEQ ID NO:73:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:73:

Leu Pro Leu Glu
1

(2) INFORMATION FOR SEQ ID NO:74:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:74:

Pro Trp Ser Glu
1

(2) INFORMATION FOR SEQ ID NO:75:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:75:

Val Ser Gly Glu
1

(2) INFORMATION FOR SEQ ID NO:76:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:76:

Tyr Ser Thr Glu
1

(2) INFORMATION FOR SEQ ID NO:77:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:77:

Ile Gly Gly Val (2) INFORMATION FOR SEQ ID NO:78:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:78:

Ile Pro Ile Ser
1

(2) INFORMATION FOR SEQ ID NO:79:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:79:

Ile Trp Gly Val
1

(2) INFORMATION FOR SEQ ID NO:80:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:80:

Val Trp Gly Ala
1

(2) INFORMATION FOR SEQ ID NO:81:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:81:

Val Trp Gly Ile
1

(2) INFORMATION FOR SEQ ID NO:82:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:82:

Val Trp Gly Val (2) INFORMATION FOR SEQ ID NO:83:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:83:

Ile Asn Gly Val
1

(2) INFORMATION FOR SEQ ID NO:84:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:84:

Thr Asn Gly Gly
1

(2) INFORMATION FOR SEQ ID NO:85:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:85:

Val Asn Gly Ala
1

(2) INFORMATION FOR SEQ ID NO:86:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:86:

Val Asn Gly Val
1

(2) INFORMATION FOR SEQ ID NO:87:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:87:

Trp Asn Met Gly (2) INFORMATION FOR SEQ ID NO:88:

(i) SEQUENCE CHARACTERISTICS:
        (A) LENGTH: 4 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:88:

Gly Pro Gln Ile
1

(2) INFORMATION FOR SEQ ID NO:89:

(i) SEQUENCE CHARACTERISTICS:
        (A) LENGTH: 3 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:89:

Val Pro Trp
1

(2) INFORMATION FOR SEQ ID NO:90:

(i) SEQUENCE CHARACTERISTICS:
        (A) LENGTH: 3 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:90:

Val Gly Trp
1

(2) INFORMATION FOR SEQ ID NO:91:

(i) SEQUENCE CHARACTERISTICS:
        (A) LENGTH: 3 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:91:

Leu Pro Phe
1

(2) INFORMATION FOR SEQ ID NO:92:

(i) SEQUENCE CHARACTERISTICS:
        (A) LENGTH: 3 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:92:

Arg Gly Trp (2) INFORMATION FOR SEQ ID NO:93:

(i) SEQUENCE CHARACTERISTICS:
        (A) LENGTH: 3 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:93:

Trp Ala Leu
1

(2) INFORMATION FOR SEQ ID NO:94:

(i) SEQUENCE CHARACTERISTICS:
        (A) LENGTH: 3 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:94:

Val Arg Trp
1

(2) INFORMATION FOR SEQ ID NO:95:

(i) SEQUENCE CHARACTERISTICS:
        (A) LENGTH: 3 amino acids
        (B) TYPE: amino acid
        (C) STRANDEDNESS: unknown
        (D) TOPOLOGY: Not Relevant (ii) MOLECULE TYPE: peptide (xi) SEQUENCE DESCRIPTION: SEQ ID NO:95:

Val Arg Leu
1

(2) INFORMATION FOR SEQ ID NO:96:

(i) SEQUENCE CHARACTERISTICS:

(xi) SEQUENCE DESCRIPTION: SEQ ID NO:96:

This sequence has been intentionally skipped (2) INFORMATION FOR SEQ ID NO:97:

(i) SEQUENCE CHARACTERISTICS:

(xi) SEQUENCE DESCRIPTION: SEQ ID NO:97:

This sequence has been intentionally skipped (2) INFORMATION FOR SEQ ID NO:98:

(i) SEQUENCE CHARACTERISTICS:

(xi) SEQUENCE DESCRIPTION: SEQ ID NO:98:

This sequence has been intentionally skipped (2) INFORMATION FOR SEQ ID NO:99:

(i) SEQUENCE CHARACTERISTICS:

(xi) SEQUENCE DESCRIPTION: SEQ ID NO:99:

This sequence has been intentionally skipped (2) INFORMATION FOR SEQ ID NO:100:

(i) SEQUENCE CHARACTERISTICS:
            (A) LENGTH: 10 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..10
            (D) OTHER INFORMATION: /product= "Cyclic"

(xi) SEQUENCE DESCRIPTION: SEQ ID NO:100:

Ser Val Arg Gly Phe Arg Val Arg Gly Phe
1               5                   10

(2) INFORMATION FOR SEQ ID NO:101:

(i) SEQUENCE CHARACTERISTICS:
            (A) LENGTH: 10 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..10
            (D) OTHER INFORMATION: /product= "Cyclic"

(ix) FEATURE:
            (A) NAME/KEY: Peptide
            (B) LOCATION: 3
            (D) OTHER INFORMATION: /product= "Xaa=D-arginine"

(ix) FEATURE:
            (A) NAME/KEY: Peptide
            (B) LOCATION: 8
            (D) OTHER INFORMATION: /product= "Xaa=D-arginine"

(xi) SEQUENCE DESCRIPTION: SEQ ID NO:101:

Ser Val Xaa Gly Phe Ser Val Xaa Gly Phe
1               5                   10

(2) INFORMATION FOR SEQ ID NO:102:

(i) SEQUENCE CHARACTERISTICS:
            (A) LENGTH: 10 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..10
            (D) OTHER INFORMATION: /product= "Cyclic"

(xi) SEQUENCE DESCRIPTION: SEQ ID NO:102:

Phe Val Arg Ser Tyr Val Leu Arg Ser Val
1               5                   10

(2) INFORMATION FOR SEQ ID NO:103:

(i) SEQUENCE CHARACTERISTICS:
        (A) LENGTH: 10 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..10
        (D) OTHER INFORMATION: /product= "Cyclic"

(xi) SEQUENCE DESCRIPTION: SEQ ID NO:103:

Phe Val Pro Arg Tyr Val Leu Pro Arg Val
1               5                   10

(2) INFORMATION FOR SEQ ID NO:104:

(i) SEQUENCE CHARACTERISTICS:
        (A) LENGTH: 10 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..10
        (D) OTHER INFORMATION: /product= "Cyclic"

(xi) SEQUENCE DESCRIPTION: SEQ ID NO:104:

Tyr Val Arg Gly Phe Val Phe Gly Arg Val
1               5                   10

(2) INFORMATION FOR SEQ ID NO:105:

(i) SEQUENCE CHARACTERISTICS:
        (A) LENGTH: 11 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..11
        (D) OTHER INFORMATION: /product= "Cyclic"

(xi) SEQUENCE DESCRIPTION: SEQ ID NO:105:

Cys Val Arg Arg Tyr Cys Leu Trp Arg Gly Val
1               5                   10

(2) INFORMATION FOR SEQ ID NO:106:

(i) SEQUENCE CHARACTERISTICS:
        (A) LENGTH: 11 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..11
        (D) OTHER INFORMATION: /product= "Cyclic"

(xi) SEQUENCE DESCRIPTION: SEQ ID NO:106:

```
Cys Val Thr Arg Tyr Cys Leu Trp Arg Gly Val
1               5                   10
```

(2) INFORMATION FOR SEQ ID NO:107:

(i) SEQUENCE CHARACTERISTICS:
        (A) LENGTH: 10 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..10
        (D) OTHER INFORMATION: /product= "Cyclic"

(xi) SEQUENCE DESCRIPTION: SEQ ID NO:107:

```
Cys Val Arg Thr Tyr Cys Leu Arg Gly Trp
1               5                   10
```

(2) INFORMATION FOR SEQ ID NO:108:

(i) SEQUENCE CHARACTERISTICS:
        (A) LENGTH: 11 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..11
        (D) OTHER INFORMATION: /product= "Cyclic"

(xi) SEQUENCE DESCRIPTION: SEQ ID NO:108:

```
Cys Val Pro Arg Tyr Cys Leu Trp Arg Gly Val
1               5                   10
```

(2) INFORMATION FOR SEQ ID NO:109:

(i) SEQUENCE CHARACTERISTICS:
        (A) LENGTH: 10 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..10
        (D) OTHER INFORMATION: /product= "Cyclic"

(xi) SEQUENCE DESCRIPTION: SEQ ID NO:109:

```
Cys Val Arg Arg Tyr Cys Leu Gly Arg Trp
1               5                   10
```

(2) INFORMATION FOR SEQ ID NO:110:

(i) SEQUENCE CHARACTERISTICS:
        (A) LENGTH: 9 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..9

(D) OTHER INFORMATION: /product= "Cyclic"

(xi) SEQUENCE DESCRIPTION: SEQ ID NO:110:

Cys Val Arg Arg Tyr Cys Leu Gly Trp
1               5

(2) INFORMATION FOR SEQ ID NO:111:

(i) SEQUENCE CHARACTERISTICS:
        (A) LENGTH: 11 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..11
        (D) OTHER INFORMATION: /product= "Cyclic"

(ix) FEATURE:
        (A) NAME/KEY: Peptide
        (B) LOCATION: 3
        (D) OTHER INFORMATION: /product= "Xaa=D-Arginine"

(xi) SEQUENCE DESCRIPTION: SEQ ID NO:111:

Cys Val Xaa Arg Tyr Cys Leu Trp Arg Gly Trp
1               5                   10

(2) INFORMATION FOR SEQ ID NO:112:

(i) SEQUENCE CHARACTERISTICS:
        (A) LENGTH: 15 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Modified-site
        (B) LOCATION: 1..15
        (D) OTHER INFORMATION: /product= "Cyclic"

(ix) FEATURE:
        (A) NAME/KEY: Peptide
        (B) LOCATION: 14
        (D) OTHER INFORMATION: /product=
            "Xaa=Dpr=2,3-diaminopropionic acid"

(xi) SEQUENCE DESCRIPTION: SEQ ID NO:112:

Cys Arg Arg Arg Phe Cys Tyr Asp Leu Trp Arg Gly Val Xaa Val
1               5                   10                  15

(2) INFORMATION FOR SEQ ID NO:113:

(i) SEQUENCE CHARACTERISTICS:
        (A) LENGTH: 15 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..15
        (D) OTHER INFORMATION: /product= "Cyclic"

(ix) FEATURE:
        (A) NAME/KEY: Peptide
        (B) LOCATION: 3
        (D) OTHER INFORMATION: /product=

"Xaa=Dpr=2,3-diaminopropionic acid"

(xi) SEQUENCE DESCRIPTION: SEQ ID NO:113:

Cys Val Xaa Arg Pro Arg Phe Asp Tyr Cys Leu Trp Arg Gly Val
1               5                   10                  15

(2) INFORMATION FOR SEQ ID NO:114:

(i) SEQUENCE CHARACTERISTICS:
        (A) LENGTH: 14 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..14
        (D) OTHER INFORMATION: /product= "Cyclic"

(ix) FEATURE:
        (A) NAME/KEY: Modified-site
        (B) LOCATION: 3
        (D) OTHER INFORMATION: /product=
            "Xaa=Dpr=2,3-diaminopropionic acid"

(xi) SEQUENCE DESCRIPTION: SEQ ID NO:114:

Cys Val Xaa Arg Pro Arg Phe Asp Tyr Cys Leu Pro Arg Trp
1               5                   10

(2) INFORMATION FOR SEQ ID NO:115:

(i) SEQUENCE CHARACTERISTICS:
        (A) LENGTH: 15 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..15
        (D) OTHER INFORMATION: /product= "Cyclic"

(ix) FEATURE:
        (A) NAME/KEY: Modified-site
        (B) LOCATION: 1
        (D) OTHER INFORMATION: /product=
            "Xaa=Dpr=2,3-diaminopropionic acid"

(ix) FEATURE:
        (A) NAME/KEY: Modified-site
        (B) LOCATION: 8
        (D) OTHER INFORMATION: /product=
            "Xaa=Dpr=2,3-diaminopropionic acid"

(xi) SEQUENCE DESCRIPTION: SEQ ID NO:115:

Xaa Val Asp Arg Pro Arg Phe Xaa Tyr Asp Leu Trp Arg Gly Val
1               5                   10                  15

(2) INFORMATION FOR SEQ ID NO:116:

(i) SEQUENCE CHARACTERISTICS:
        (A) LENGTH: 10 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide (B) LOCATION: 1..10
            (D) OTHER INFORMATION: /product= "Cyclic"

(ix) FEATURE:
            (A) NAME/KEY: Modified-site
            (B) LOCATION: 3
            (D) OTHER INFORMATION: /product= "Xaa=O=Ornithine"

(ix) FEATURE:
            (A) NAME/KEY: Modified-site
            (B) LOCATION: 8
            (D) OTHER INFORMATION: /product= "Xaa=O=Ornithine"

(xi) SEQUENCE DESCRIPTION: SEQ ID NO:116:

Ser Val Xaa Gly Phe Ser Val Xaa Gly Phe
1               5                   10

(2) INFORMATION FOR SEQ ID NO:117:

(i) SEQUENCE CHARACTERISTICS:
            (A) LENGTH: 10 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..10
            (D) OTHER INFORMATION: /product= "Cyclic"

(ix) FEATURE:
            (A) NAME/KEY: Modified-site
            (B) LOCATION: 4
            (D) OTHER INFORMATION: /product= "Xaa=O=Ornithine"

(ix) FEATURE:
            (A) NAME/KEY: Modified-site
            (B) LOCATION: 9
            (D) OTHER INFORMATION: /product= "Xaa=O=Ornithine"

(xi) SEQUENCE DESCRIPTION: SEQ ID NO:117:

Phe Val Gly Xaa Tyr Val Leu Gly Xaa Val
1               5                   10

(2) INFORMATION FOR SEQ ID NO:118:

(i) SEQUENCE CHARACTERISTICS:
            (A) LENGTH: 10 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..10
            (D) OTHER INFORMATION: /product= "Cyclic"

(ix) FEATURE:
            (A) NAME/KEY: Modified-site
            (B) LOCATION: 4
            (D) OTHER INFORMATION: /product= "Xaa=O=Ornithine"

(ix) FEATURE:
            (A) NAME/KEY: Modified-site
            (B) LOCATION: 9
            (D) OTHER INFORMATION: /product= "Xaa=O=Ornithine"

(xi) SEQUENCE DESCRIPTION: SEQ ID NO:118:

Phe Val Gly Xaa Tyr Val Trp Pro Xaa Val
1               5                   10

(2) INFORMATION FOR SEQ ID NO:119:

(i) SEQUENCE CHARACTERISTICS:
        (A) LENGTH: 10 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..10
        (D) OTHER INFORMATION: /product= "Cyclic"

(ix) FEATURE:
        (A) NAME/KEY: Modified-site
        (B) LOCATION: 9
        (D) OTHER INFORMATION: /product= "Xaa=O=Ornithine"

(xi) SEQUENCE DESCRIPTION: SEQ ID NO:119:

```
Tyr Val Arg Gly Phe Val Phe Gly Xaa Val
1               5                   10
```

(2) INFORMATION FOR SEQ ID NO:120:

(i) SEQUENCE CHARACTERISTICS:
        (A) LENGTH: 10 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..10
        (D) OTHER INFORMATION: /product= "Cyclic"

(ix) FEATURE:
        (A) NAME/KEY: Modified-site
        (B) LOCATION: 3
        (D) OTHER INFORMATION: /product= "Xaa=O=Ornithine"

(ix) FEATURE:
        (A) NAME/KEY: Modified-site
        (B) LOCATION: 8
        (D) OTHER INFORMATION: /product= "Xaa=O=Ornithine"

(xi) SEQUENCE DESCRIPTION: SEQ ID NO:120:

```
Tyr Val Xaa Gly Phe Val Phe Xaa Gly Val
1               5                   10
```

(2) INFORMATION FOR SEQ ID NO:121:

(i) SEQUENCE CHARACTERISTICS:
        (A) LENGTH: 11 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..11
        (D) OTHER INFORMATION: /product= "Cyclic"

(ix) FEATURE:
        (A) NAME/KEY: Modified-site
        (B) LOCATION: 4
        (D) OTHER INFORMATION: /product= "Xaa=O=Ornithine"

(ix) FEATURE:
        (A) NAME/KEY: Modified-site (B) LOCATION: 9
        (D) OTHER INFORMATION: /product= "Xaa=O=Ornithine"

(xi) SEQUENCE DESCRIPTION: SEQ ID NO:121:

Cys Tyr Ser Xaa Tyr Cys Leu Trp Xaa Gly Val
1               5                   10

(2) INFORMATION FOR SEQ ID NO:122:

(i) SEQUENCE CHARACTERISTICS:
        (A) LENGTH: 11 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..11
        (D) OTHER INFORMATION: /product= "Cyclic"

(ix) FEATURE:
        (A) NAME/KEY: Modified-site
        (B) LOCATION: 4
        (D) OTHER INFORMATION: /product= "Xaa=O=Ornithine"

(ix) FEATURE:
        (A) NAME/KEY: Modified-site
        (B) LOCATION: 9
        (D) OTHER INFORMATION: /product= "Xaa=O=Ornithine"

(xi) SEQUENCE DESCRIPTION: SEQ ID NO:122:

Cys Val Pro Xaa Tyr Cys Leu Trp Xaa Gly Val
1               5                   10

(2) INFORMATION FOR SEQ ID NO:123:

(i) SEQUENCE CHARACTERISTICS:
        (A) LENGTH: 11 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..11
        (D) OTHER INFORMATION: /product= "Cyclic"

(ix) FEATURE:
        (A) NAME/KEY: Modified-site
        (B) LOCATION: 3, 4
        (D) OTHER INFORMATION: /product= "Xaa=O=Ornithine"

(ix) FEATURE:
        (A) NAME/KEY: Modified-site
        (B) LOCATION: 9
        (D) OTHER INFORMATION: /product= "Xaa=O=Ornithine"

(xi) SEQUENCE DESCRIPTION: SEQ ID NO:123:

Cys Val Xaa Xaa Tyr Cys Leu Trp Xaa Gly Phe
1               5                   10

(2) INFORMATION FOR SEQ ID NO:124:

(i) SEQUENCE CHARACTERISTICS:
        (A) LENGTH: 10 amino acids
        (B) TYPE: amino acid
        (C) STRANDEDNESS: unknown
        (D) TOPOLOGY: circular (ii) MOLECULE TYPE: peptide (ix) FEATURE:
            (A) NAME/KEY: Peptide
            (B) LOCATION: 1..10
            (D) OTHER INFORMATION: /product= "Cyclic"

(xi) SEQUENCE DESCRIPTION: SEQ ID NO:124:

Ser Val Lys Gly Phe Lys Val Lys Gly Phe
1               5                   10

(2) INFORMATION FOR SEQ ID NO:125:

(i) SEQUENCE CHARACTERISTICS:
            (A) LENGTH: 10 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..10
            (D) OTHER INFORMATION: /product= "Cyclic"

(xi) SEQUENCE DESCRIPTION: SEQ ID NO:125:

Phe Val Gly Lys Tyr Val Leu Gly Lys Val
1               5                   10

(2) INFORMATION FOR SEQ ID NO:126:

(i) SEQUENCE CHARACTERISTICS:
            (A) LENGTH: 10 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..10
            (D) OTHER INFORMATION: /product= "Cyclic"

(xi) SEQUENCE DESCRIPTION: SEQ ID NO:126:

Phe Val Gly Lys Tyr Val Trp Pro Lys Val
1               5                   10

(2) INFORMATION FOR SEQ ID NO:127:

(i) SEQUENCE CHARACTERISTICS:
            (A) LENGTH: 10 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..10
            (D) OTHER INFORMATION: /product= "Cyclic"

(xi) SEQUENCE DESCRIPTION: SEQ ID NO:127:

Tyr Val Lys Gly Phe Val Phe Gly Lys Val
1               5                   10

(2) INFORMATION FOR SEQ ID NO:128:

(i) SEQUENCE CHARACTERISTICS:
            (A) LENGTH: 10 amino acids
            (B) TYPE: amino acid (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..10
        (D) OTHER INFORMATION: /product= "Cyclic"

(xi) SEQUENCE DESCRIPTION: SEQ ID NO:128:

Tyr Ala Lys Gly Phe Val Phe Gly Lys Val
1               5                   10

(2) INFORMATION FOR SEQ ID NO:129:

(i) SEQUENCE CHARACTERISTICS:
        (A) LENGTH: 11 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..11
        (D) OTHER INFORMATION: /product= "Cyclic"

(xi) SEQUENCE DESCRIPTION: SEQ ID NO:129:

Cys Val Lys Lys Tyr Cys Leu Trp Lys Gly Val
1               5                   10

(2) INFORMATION FOR SEQ ID NO:130:

(i) SEQUENCE CHARACTERISTICS:
        (A) LENGTH: 11 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..11
        (D) OTHER INFORMATION: /product= "Cyclic"

(xi) SEQUENCE DESCRIPTION: SEQ ID NO:130:

Cys Val Ser Lys Tyr Cys Leu Trp Lys Gly Val
1               5                   10

(2) INFORMATION FOR SEQ ID NO:131:

(i) SEQUENCE CHARACTERISTICS:
        (A) LENGTH: 9 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..9
        (D) OTHER INFORMATION: /product= "Cyclic"

(xi) SEQUENCE DESCRIPTION: SEQ ID NO:131:

Cys Val Ser Lys Tyr Cys Leu Gly Trp
1               5

(2) INFORMATION FOR SEQ ID NO:132:

(i) SEQUENCE CHARACTERISTICS:
            (A) LENGTH: 10 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..10
            (D) OTHER INFORMATION: /product= "Cyclic"

(xi) SEQUENCE DESCRIPTION: SEQ ID NO:132:

Cys Val Pro Lys Tyr Cys Leu Lys Gly Trp
1               5                   10

(2) INFORMATION FOR SEQ ID NO:133:

(i) SEQUENCE CHARACTERISTICS:
            (A) LENGTH: 11 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..11
            (D) OTHER INFORMATION: /product= "Cyclic"

(xi) SEQUENCE DESCRIPTION: SEQ ID NO:133:

Cys Gly Phe Arg Ser Cys Val Gly Arg Trp Leu
1               5                   10

(2) INFORMATION FOR SEQ ID NO:134:

(i) SEQUENCE CHARACTERISTICS:
            (A) LENGTH: 11 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..11
            (D) OTHER INFORMATION: /product= "Cyclic"

(xi) SEQUENCE DESCRIPTION: SEQ ID NO:134:

Cys Ile Arg Gly Val Cys Leu Trp Lys Gly Tyr
1               5                   10

(2) INFORMATION FOR SEQ ID NO:135:

(i) SEQUENCE CHARACTERISTICS:
            (A) LENGTH: 10 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..10
            (D) OTHER INFORMATION: /product= "Cyclic"

(xi) SEQUENCE DESCRIPTION: SEQ ID NO:135:

Cys Gly Phe Arg Ser Cys Val Gly Arg Trp

```
                        1               5                   10
```

(2) INFORMATION FOR SEQ ID NO:136:

(i) SEQUENCE CHARACTERISTICS:
        (A) LENGTH: 9 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..9
        (D) OTHER INFORMATION: /product= "Cyclic"

(xi) SEQUENCE DESCRIPTION: SEQ ID NO:136:

```
Cys Arg Gly Val Cys Trp Arg Gly Tyr
1               5
```

(2) INFORMATION FOR SEQ ID NO:137:

(i) SEQUENCE CHARACTERISTICS:

(xi) SEQUENCE DESCRIPTION: SEQ ID NO:137:

This sequence has been intentionally skipped (2) INFORMATION FOR SEQ ID NO:138:

(i) SEQUENCE CHARACTERISTICS:

(xi) SEQUENCE DESCRIPTION: SEQ ID NO:138:

This sequence has been intentionally skipped (2) INFORMATION FOR SEQ ID NO:139:

(i) SEQUENCE CHARACTERISTICS:

(xi) SEQUENCE DESCRIPTION: SEQ ID NO:139:

This sequence has been intentionally skipped (2) INFORMATION FOR SEQ ID NO:140:

(i) SEQUENCE CHARACTERISTICS:
        (A) LENGTH: 17 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..17
        (D) OTHER INFORMATION: /product= "Cyclic"

(xi) SEQUENCE DESCRIPTION: SEQ ID NO:140:

```
Cys Leu Arg Tyr Cys Arg Arg Arg Phe Cys Val Arg Phe Cys Leu Trp
1               5                   10                  15

Phe
```

(2) INFORMATION FOR SEQ ID NO:141:

(i) SEQUENCE CHARACTERISTICS:
        (A) LENGTH: 16 amino acids
        (B) TYPE: amino acid
        (C) STRANDEDNESS: unknown (D) TOPOLOGY: circular (ii) MOLECULE TYPE: peptide (ix) FEATURE:
          (A) NAME/KEY: Peptide
          (B) LOCATION: 1..16
          (D) OTHER INFORMATION: /product= "Cyclic"

(ix) FEATURE:
          (A) NAME/KEY: Modified-site
          (B) LOCATION: 7
          (D) OTHER INFORMATION: /product= "Xaa=D-Arginine"

(xi) SEQUENCE DESCRIPTION: SEQ ID NO:141:

Cys Leu Arg Tyr Cys Arg Xaa Phe Cys Val Arg Phe Cys Leu Trp
1               5                  10                  15

Phe (2) INFORMATION FOR SEQ ID NO:142:

(i) SEQUENCE CHARACTERISTICS:
          (A) LENGTH: 17 amino acids
          (B) TYPE: amino acid
          (C) STRANDEDNESS: unknown
          (D) TOPOLOGY: circular (ii) MOLECULE TYPE: peptide (ix) FEATURE:
          (A) NAME/KEY: Peptide
          (B) LOCATION: 1..17
          (D) OTHER INFORMATION: /product= "Cyclic"

(xi) SEQUENCE DESCRIPTION: SEQ ID NO:142:

Cys Leu Arg Tyr Cys Arg Pro Phe Cys Val Ser Tyr Cys Val Arg Trp
1               5                  10                  15

Phe (2) INFORMATION FOR SEQ ID NO:143:

(i) SEQUENCE CHARACTERISTICS:
          (A) LENGTH: 18 amino acids
          (B) TYPE: amino acid
          (C) STRANDEDNESS: unknown
          (D) TOPOLOGY: circular (ii) MOLECULE TYPE: peptide (ix) FEATURE:
          (A) NAME/KEY: Peptide
          (B) LOCATION: 1..18
          (D) OTHER INFORMATION: /product= "Cyclic"

(xi) SEQUENCE DESCRIPTION: SEQ ID NO:143:

Cys Leu Arg Tyr Cys Arg Ile Pro Ile Cys Val Arg Phe Cys Val Pro
1               5                  10                  15

Arg Trp (2) INFORMATION FOR SEQ ID NO:144:

(i) SEQUENCE CHARACTERISTICS:
          (A) LENGTH: 18 amino acids
          (B) TYPE: amino acid
          (C) STRANDEDNESS: unknown
          (D) TOPOLOGY: circular (ii) MOLECULE TYPE: peptide (ix) FEATURE:
          (A) NAME/KEY: Peptide (B) LOCATION: 1..18
            (D) OTHER INFORMATION: /product= "Cyclic"

(ix) FEATURE:
            (A) NAME/KEY: Modified-site
            (B) LOCATION: 7
            (D) OTHER INFORMATION: /product= "Xaa=D-Phenylalanine"

(xi) SEQUENCE DESCRIPTION: SEQ ID NO:144:

Cys Leu Arg Tyr Cys Arg Xaa Pro Phe Cys Val Arg Phe Cys Leu
1               5                   10                  15

Ser Arg Trp (2) INFORMATION FOR SEQ ID NO:145:

(i) SEQUENCE CHARACTERISTICS:
            (A) LENGTH: 18 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..18
            (D) OTHER INFORMATION: /product= "Cyclic"

(ix) FEATURE:
            (A) NAME/KEY: Modified-site
            (B) LOCATION: 3
            (D) OTHER INFORMATION: /product=
                "Xaa=Dpr=2,3-diaminopropionic acid"

(xi) SEQUENCE DESCRIPTION: SEQ ID NO:145:

Cys Leu Xaa Tyr Cys Arg Arg Arg Phe Cys Val Asp Tyr Cys Val
1               5                   10                  15

Arg Gly Trp (2) INFORMATION FOR SEQ ID NO:146:

(i) SEQUENCE CHARACTERISTICS:
            (A) LENGTH: 17 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..17
            (D) OTHER INFORMATION: /product= "Cyclic"

(ix) FEATURE:
            (A) NAME/KEY: Modified-site
            (B) LOCATION: 3
            (D) OTHER INFORMATION: /product=
                "Xaa=Dpr=2,3-diaminopropionic acid"

(xi) SEQUENCE DESCRIPTION: SEQ ID NO:146:

Cys Leu Xaa Tyr Cys Val Arg Arg Phe Cys Val Asp Tyr Cys Val
1               5                   10                  15

Gly Trp (2) INFORMATION FOR SEQ ID NO:147:

(i) SEQUENCE CHARACTERISTICS:
            (A) LENGTH: 17 amino acids
            (B) TYPE: amino acid
            (C) STRANDEDNESS: unknown (D) TOPOLOGY: circular (ii) MOLECULE TYPE: peptide (ix) FEATURE:
           (A) NAME/KEY: Peptide
           (B) LOCATION: 1..17
           (D) OTHER INFORMATION: /product= "Cyclic"

(ix) FEATURE:
           (A) NAME/KEY: Modified-site
           (B) LOCATION: 3
           (D) OTHER INFORMATION: /product=
               "Xaa=Dpr=2,3-diaminopropionic acid"

(xi) SEQUENCE DESCRIPTION: SEQ ID NO:147:

Cys Leu Xaa Tyr Cys Arg Ser Arg Phe Cys Val Asp Tyr Cys Val
1               5                   10                  15

Gly Trp (2) INFORMATION FOR SEQ ID NO:148:

(i) SEQUENCE CHARACTERISTICS:

(xi) SEQUENCE DESCRIPTION: SEQ ID NO:148:

This sequence has been intentionally skipped (2) INFORMATION FOR SEQ ID NO:149:

(i) SEQUENCE CHARACTERISTICS:

(xi) SEQUENCE DESCRIPTION: SEQ ID NO:149:

This sequence has been intentionally skipped (2) INFORMATION FOR SEQ ID NO:150:

(i) SEQUENCE CHARACTERISTICS:
          (A) LENGTH: 12 amino acids
          (B) TYPE: amino acid
          (C) STRANDEDNESS: unknown
          (D) TOPOLOGY: circular (ii) MOLECULE TYPE: peptide (ix) FEATURE:
           (A) NAME/KEY: Peptide
           (B) LOCATION: 1..12
           (D) OTHER INFORMATION: /product= "Cyclic"

(xi) SEQUENCE DESCRIPTION: SEQ ID NO:150:

Cys Tyr Cys Arg Arg Arg Phe Cys Val Cys Val Leu
1               5                   10

(2) INFORMATION FOR SEQ ID NO:151:

(i) SEQUENCE CHARACTERISTICS:
          (A) LENGTH: 13 amino acids
          (B) TYPE: amino acid
          (C) STRANDEDNESS: unknown
          (D) TOPOLOGY: circular (ii) MOLECULE TYPE: peptide (ix) FEATURE:
           (A) NAME/KEY: Peptide
           (B) LOCATION: 1..13
           (D) OTHER INFORMATION: /product= "Cyclic"

(xi) SEQUENCE DESCRIPTION: SEQ ID NO:151:

Cys Tyr Cys Arg Arg Arg Phe Cys Val Cys Val Trp Tyr

```
                    1               5                   10

(2) INFORMATION FOR SEQ ID NO:152:

(i) SEQUENCE CHARACTERISTICS:
          (A) LENGTH: 11 amino acids
          (B) TYPE: amino acid
          (C) STRANDEDNESS: unknown
          (D) TOPOLOGY: circular (ii) MOLECULE TYPE: peptide (ix) FEATURE:
          (A) NAME/KEY: Peptide
          (B) LOCATION: 1..11
          (D) OTHER INFORMATION: /product= "Cyclic"

(xi) SEQUENCE DESCRIPTION: SEQ ID NO:152:

Cys Tyr Cys Arg Gly Arg Phe Cys Val Arg Trp
1               5                   10

(2) INFORMATION FOR SEQ ID NO:153:

(i) SEQUENCE CHARACTERISTICS:
          (A) LENGTH: 13 amino acids
          (B) TYPE: amino acid
          (C) STRANDEDNESS: unknown
          (D) TOPOLOGY: circular (ii) MOLECULE TYPE: peptide (ix) FEATURE:
          (A) NAME/KEY: Peptide
          (B) LOCATION: 1..13
          (D) OTHER INFORMATION: /product= "Cyclic"

(ix) FEATURE:
          (A) NAME/KEY: Modified-site
          (B) LOCATION: 5
          (D) OTHER INFORMATION: /product= "Xaa=D-Arginine"

(ix) FEATURE:
          (A) NAME/KEY: Modified-site
          (B) LOCATION: 6
          (D) OTHER INFORMATION: /product= "Xaa=D-Arginine"

(xi) SEQUENCE DESCRIPTION: SEQ ID NO:153:

Cys Val Cys Phe Xaa Xaa Arg Cys Tyr Cys Leu Trp Val
1               5                   10

(2) INFORMATION FOR SEQ ID NO:154:

(i) SEQUENCE CHARACTERISTICS:
          (A) LENGTH: 13 amino acids
          (B) TYPE: amino acid
          (C) STRANDEDNESS: unknown
          (D) TOPOLOGY: circular (ii) MOLECULE TYPE: peptide (ix) FEATURE:
          (A) NAME/KEY: Peptide
          (B) LOCATION: 1..13
          (D) OTHER INFORMATION: /product= "Cyclic"

(xi) SEQUENCE DESCRIPTION: SEQ ID NO:154:

Cys Tyr Cys Arg Arg Arg Phe Cys Val Cys Val Arg Leu
1               5                   10

(2) INFORMATION FOR SEQ ID NO:155:

(i) SEQUENCE CHARACTERISTICS:
          (A) LENGTH: 13 amino acids
```

```
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..13
        (D) OTHER INFORMATION: /product= "Cyclic"

(ix) FEATURE:
        (A) NAME/KEY: Modified-site
        (B) LOCATION: 5
        (D) OTHER INFORMATION: /product= "Xaa=D-Arginine"

(ix) FEATURE:
        (A) NAME/KEY: Modified-site
        (B) LOCATION: 6
        (D) OTHER INFORMATION: /product= "Xaa=D-Arginine"

(xi) SEQUENCE DESCRIPTION: SEQ ID NO:155:

Cys Val Cys Phe Xaa Xaa Arg Cys Tyr Cys Leu Arg Val
1               5                   10

(2) INFORMATION FOR SEQ ID NO:156:

(i) SEQUENCE CHARACTERISTICS:
        (A) LENGTH: 14 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..14
        (D) OTHER INFORMATION: /product= "Cyclic"

(xi) SEQUENCE DESCRIPTION: SEQ ID NO:156:

Cys Tyr Cys Arg Arg Arg Phe Cys Val Cys Ile Phe Gly Arg
1               5                   10

(2) INFORMATION FOR SEQ ID NO:157:

(i) SEQUENCE CHARACTERISTICS:
        (A) LENGTH: 14 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..14
        (D) OTHER INFORMATION: /product= "Cyclic"

(xi) SEQUENCE DESCRIPTION: SEQ ID NO:157:

Cys Tyr Cys Arg Arg Arg Phe Cys Val Cys Ile Ser Gly Arg
1               5                   10

(2) INFORMATION FOR SEQ ID NO:158:

(i) SEQUENCE CHARACTERISTICS:
        (A) LENGTH: 14 amino acids
        (B) TYPE: amino acid
        (C) STRANDEDNESS: unknown
        (D) TOPOLOGY: circular (ii) MOLECULE TYPE: peptide (ix) FEATURE:
```

(A) NAME/KEY: Peptide
        (B) LOCATION: 1..14
        (D) OTHER INFORMATION: /product= "Cyclic"

(xi) SEQUENCE DESCRIPTION: SEQ ID NO:158:

Cys Tyr Cys Arg Arg Arg Phe Cys Val Cys Ile Arg Gly Val
1               5                   10

(2) INFORMATION FOR SEQ ID NO:159:

(i) SEQUENCE CHARACTERISTICS:
        (A) LENGTH: 14 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..14
        (D) OTHER INFORMATION: /product= "Cyclic"

(xi) SEQUENCE DESCRIPTION: SEQ ID NO:159:

Cys Tyr Cys Arg Arg Arg Phe Cys Val Cys Ile Trp Gly Arg
1               5                   10

(2) INFORMATION FOR SEQ ID NO:160:

(i) SEQUENCE CHARACTERISTICS:
        (A) LENGTH: 14 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..14
        (D) OTHER INFORMATION: /product= "Cyclic"

(xi) SEQUENCE DESCRIPTION: SEQ ID NO:160:

Cys Tyr Cys Arg Arg Arg Phe Cys Val Cys Arg Phe Pro Tyr
1               5                   10

(2) INFORMATION FOR SEQ ID NO:161:

(i) SEQUENCE CHARACTERISTICS:
        (A) LENGTH: 14 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..14
        (D) OTHER INFORMATION: /product= "Cyclic"

(xi) SEQUENCE DESCRIPTION: SEQ ID NO:161:

Cys Tyr Cys Arg Arg Arg Phe Cys Val Cys Arg Gly Phe Leu
1               5                   10

(2) INFORMATION FOR SEQ ID NO:162:

(i) SEQUENCE CHARACTERISTICS:
        (A) LENGTH: 14 amino acids
        (B) TYPE: amino acid
        (C) STRANDEDNESS: unknown
        (D) TOPOLOGY: circular (ii) MOLECULE TYPE: peptide (ix) FEATURE:
            (A) NAME/KEY: Peptide
            (B) LOCATION: 1..14
            (D) OTHER INFORMATION: /product= "Cyclic"

(xi) SEQUENCE DESCRIPTION: SEQ ID NO:162:

Cys Tyr Cys Arg Arg Arg Phe Cys Val Cys Arg Gly Trp Val
1               5                   10

(2) INFORMATION FOR SEQ ID NO:163:

(i) SEQUENCE CHARACTERISTICS:
            (A) LENGTH: 14 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..14
            (D) OTHER INFORMATION: /product= "Cyclic"

(xi) SEQUENCE DESCRIPTION: SEQ ID NO:163:

Cys Tyr Cys Arg Arg Arg Phe Cys Val Cys Arg Gly Trp Ile
1               5                   10

(2) INFORMATION FOR SEQ ID NO:164:

(i) SEQUENCE CHARACTERISTICS:
            (A) LENGTH: 14 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..14
            (D) OTHER INFORMATION: /product= "Cyclic"

(xi) SEQUENCE DESCRIPTION: SEQ ID NO:164:

Cys Tyr Cys Arg Arg Arg Phe Cys Val Cys Arg Ile Pro Ala
1               5                   10

(2) INFORMATION FOR SEQ ID NO:165:

(i) SEQUENCE CHARACTERISTICS:
            (A) LENGTH: 14 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..14
            (D) OTHER INFORMATION: /product= "Cyclic"

(xi) SEQUENCE DESCRIPTION: SEQ ID NO:165:

Cys Tyr Cys Arg Arg Arg Phe Cys Val Cys Tyr Arg Gly Arg
1               5                   10

(2) INFORMATION FOR SEQ ID NO:166:

(i) SEQUENCE CHARACTERISTICS:

(A) LENGTH: 14 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..14
        (D) OTHER INFORMATION: /product= "Cyclic"

(xi) SEQUENCE DESCRIPTION: SEQ ID NO:166:

Cys Tyr Cys Arg Arg Arg Phe Cys Val Cys Arg Leu Val Phe
1               5                   10

(2) INFORMATION FOR SEQ ID NO:167:

(i) SEQUENCE CHARACTERISTICS:
        (A) LENGTH: 13 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..13
        (D) OTHER INFORMATION: /product= "Cyclic"

(ix) FEATURE:
        (A) NAME/KEY: Modified-site
        (B) LOCATION: 13
        (D) OTHER INFORMATION: /product= "Xaa=Cha=cyclohexylalanine"

(xi) SEQUENCE DESCRIPTION: SEQ ID NO:167:

Cys Tyr Cys Arg Arg Arg Phe Cys Val Cys Val Arg Xaa
1               5                   10

(2) INFORMATION FOR SEQ ID NO:168:

(i) SEQUENCE CHARACTERISTICS:
        (A) LENGTH: 13 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..13
        (D) OTHER INFORMATION: /product= "Cyclic"

(ix) FEATURE:
        (A) NAME/KEY: Modified-site
        (B) LOCATION: 13
        (D) OTHER INFORMATION: /product= "Xaa=Cha=cyclohexylalanine"

(xi) SEQUENCE DESCRIPTION: SEQ ID NO:168:

Cys Tyr Cys Arg Pro Arg Phe Cys Val Cys Val Arg Xaa
1               5                   10

(2) INFORMATION FOR SEQ ID NO:169:

(i) SEQUENCE CHARACTERISTICS:
        (A) LENGTH: 13 amino acids
        (B) TYPE: amino acid
        (C) STRANDEDNESS: unknown
        (D) TOPOLOGY: circular (ii) MOLECULE TYPE: peptide (ix) FEATURE:
    (A) NAME/KEY: Peptide
    (B) LOCATION: 1..13
    (D) OTHER INFORMATION: /product= "Cyclic"

(ix) FEATURE:
    (A) NAME/KEY: Modified-site
    (B) LOCATION: 13
    (D) OTHER INFORMATION: /product= "Xaa=Cha=cyclohexylalanine"

(xi) SEQUENCE DESCRIPTION: SEQ ID NO:169:

Cys Tyr Cys Phe Arg Arg Phe Cys Val Cys Val Arg Xaa
1               5                   10

(2) INFORMATION FOR SEQ ID NO:170:

(i) SEQUENCE CHARACTERISTICS:
        (A) LENGTH: 14 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..14
        (D) OTHER INFORMATION: /product= "Cyclic"

(ix) FEATURE:
        (A) NAME/KEY: Modified-site
        (B) LOCATION: 14
        (D) OTHER INFORMATION: /product= "Xaa=Cha=cyclohexylalanine"

(xi) SEQUENCE DESCRIPTION: SEQ ID NO:170:

Cys Tyr Cys Arg Arg Arg Phe Cys Val Cys Val Arg Gly Xaa
1               5                   10

(2) INFORMATION FOR SEQ ID NO:171:

(i) SEQUENCE CHARACTERISTICS:
        (A) LENGTH: 13 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..13
        (D) OTHER INFORMATION: /product= "Cyclic"

(xi) SEQUENCE DESCRIPTION: SEQ ID NO:171:

Cys Tyr Cys Arg Arg Arg Phe Cys Val Cys Val Arg Trp
1               5                   10

(2) INFORMATION FOR SEQ ID NO:172:

(i) SEQUENCE CHARACTERISTICS:
        (A) LENGTH: 13 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..13
        (D) OTHER INFORMATION: /product= "Cyclic"

(xi) SEQUENCE DESCRIPTION: SEQ ID NO:172:

```
Cys Tyr Cys Arg Pro Arg Phe Cys Val Cys Val Arg Trp
1               5                   10
```

(2) INFORMATION FOR SEQ ID NO:173:

(i) SEQUENCE CHARACTERISTICS:
        (A) LENGTH: 13 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..13
        (D) OTHER INFORMATION: /product= "Cyclic"

(ix) FEATURE:
        (A) NAME/KEY: Modified-site
        (B) LOCATION: 13
        (D) OTHER INFORMATION: /product= "Xaa=Cha=cyclohexylalanine"

(xi) SEQUENCE DESCRIPTION: SEQ ID NO:173:

```
Cys Tyr Cys Arg Ser Arg Phe Cys Val Cys Val Arg Xaa
1               5                   10
```

(2) INFORMATION FOR SEQ ID NO:174:

(i) SEQUENCE CHARACTERISTICS:
        (A) LENGTH: 13 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..13
        (D) OTHER INFORMATION: /product= "Cyclic"

(xi) SEQUENCE DESCRIPTION: SEQ ID NO:174:

```
Cys Tyr Cys Val Arg Arg Phe Cys Val Cys Val Arg Trp
1               5                   10
```

(2) INFORMATION FOR SEQ ID NO:175:

(i) SEQUENCE CHARACTERISTICS:
        (A) LENGTH: 13 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..13
        (D) OTHER INFORMATION: /product= "Cyclic"

(ix) FEATURE:
        (A) NAME/KEY: Modified-site
        (B) LOCATION: 5
        (D) OTHER INFORMATION: /product= "Xaa=O=Ornithine"

(ix) FEATURE:
        (A) NAME/KEY: Modified-site
        (B) LOCATION: 6
        (D) OTHER INFORMATION: /product= "Xaa=O=Ornithine"

(ix) FEATURE:
        (A) NAME/KEY: Modified-site
        (B) LOCATION: 12
        (D) OTHER INFORMATION: /product= "Xaa=O=Ornithine"

(xi) SEQUENCE DESCRIPTION: SEQ ID NO:175:

Cys Phe Cys Val Xaa Xaa Phe Cys Val Cys Phe Xaa Val
1               5                   10

(2) INFORMATION FOR SEQ ID NO:176:

(i) SEQUENCE CHARACTERISTICS:
        (A) LENGTH: 13 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..13
        (D) OTHER INFORMATION: /product= "Cyclic"

(ix) FEATURE:
        (A) NAME/KEY: Modified-site
        (B) LOCATION: 5
        (D) OTHER INFORMATION: /product= "Xaa=O=Ornithine"

(ix) FEATURE:
        (A) NAME/KEY: Modified-site
        (B) LOCATION: 6
        (D) OTHER INFORMATION: /product= "Xaa=O=Ornithine"

(ix) FEATURE:
        (A) NAME/KEY: Modified-site
        (B) LOCATION: 12
        (D) OTHER INFORMATION: /product= "Xaa=O=Ornithine"

(xi) SEQUENCE DESCRIPTION: SEQ ID NO:176:

Cys Phe Cys Val Xaa Xaa Tyr Cys Val Cys Val Xaa Trp
1               5                   10

(2) INFORMATION FOR SEQ ID NO:177:

(i) SEQUENCE CHARACTERISTICS:
        (A) LENGTH: 13 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..13
        (D) OTHER INFORMATION: /product= "Cyclic"

(ix) FEATURE:
        (A) NAME/KEY: Modified-site
        (B) LOCATION: 4
        (D) OTHER INFORMATION: /product= "Xaa=O=Ornithine"

(ix) FEATURE:
        (A) NAME/KEY: Modified-site
        (B) LOCATION: 6
        (D) OTHER INFORMATION: /product= "Xaa=D-Ornithine"

(ix) FEATURE:
        (A) NAME/KEY: Modified-site
        (B) LOCATION: 12
        (D) OTHER INFORMATION: /product= "Xaa=O=Ornithine"

(ix) FEATURE:
        (A) NAME/KEY: Modified-site
        (B) LOCATION: 13
        (D) OTHER INFORMATION: /product= "Xaa=Cha=cyclohexylalanine"

(xi) SEQUENCE DESCRIPTION: SEQ ID NO:177:

```
Cys Phe Cys Xaa Pro Xaa Tyr Cys Val Cys Val Xaa Xaa
1               5                   10
```

(2) INFORMATION FOR SEQ ID NO:178:

(i) SEQUENCE CHARACTERISTICS:
        (A) LENGTH: 13 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..13
        (D) OTHER INFORMATION: /product= "Cyclic"

(ix) FEATURE:
        (A) NAME/KEY: Modified-site
        (B) LOCATION: 5
        (D) OTHER INFORMATION: /product= "Xaa=O=Ornithine"

(ix) FEATURE:
        (A) NAME/KEY: Modified-site
        (B) LOCATION: 12
        (D) OTHER INFORMATION: /product= "Xaa=O=Ornithine"

(ix) FEATURE:
        (A) NAME/KEY: Modified-site
        (B) LOCATION: 13
        (D) OTHER INFORMATION: /product= "Xaa=Cha=cyclohexylalanine"

(xi) SEQUENCE DESCRIPTION: SEQ ID NO:178:

```
Cys Phe Cys Val Xaa Thr Tyr Cys Val Cys Val Xaa Xaa
1               5                   10
```

(2) INFORMATION FOR SEQ ID NO:179:

(i) SEQUENCE CHARACTERISTICS:
        (A) LENGTH: 13 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..13
        (D) OTHER INFORMATION: /product= "Cyclic"

(ix) FEATURE:
        (A) NAME/KEY: Peptide
        (B) LOCATION: 5
        (D) OTHER INFORMATION: /product= "Xaa=MeGly"

(ix) FEATURE:
        (A) NAME/KEY: Modified-site
        (B) LOCATION: 6
        (D) OTHER INFORMATION: /product= "Xaa=D-ornithine"

(ix) FEATURE:
        (A) NAME/KEY: Peptide
        (B) LOCATION: 12
        (D) OTHER INFORMATION: /product= "Xaa=O=Ornithine"

(xi) SEQUENCE DESCRIPTION: SEQ ID NO:179:

```
Cys Phe Cys Val Xaa Xaa Tyr Cys Val Cys Tyr Xaa Val
1               5                   10
```

(2) INFORMATION FOR SEQ ID NO:180:

(i) SEQUENCE CHARACTERISTICS:
        (A) LENGTH: 14 amino acids (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..14
        (D) OTHER INFORMATION: /product= "Cyclic"

(ix) FEATURE:
        (A) NAME/KEY: Modified-site
        (B) LOCATION: 4
        (D) OTHER INFORMATION: /product= "Xaa=O=Ornithine"

(ix) FEATURE:
        (A) NAME/KEY: Modified-site
        (B) LOCATION: 5
        (D) OTHER INFORMATION: /product= "Xaa=D-Ornithine"

(ix) FEATURE:
        (A) NAME/KEY: Modified-site
        (B) LOCATION: 6
        (D) OTHER INFORMATION: /product= "Xaa=O=Ornithine"

(ix) FEATURE:
        (A) NAME/KEY: Modified-site
        (B) LOCATION: 12
        (D) OTHER INFORMATION: /product= "Xaa=O=Ornithine"

(xi) SEQUENCE DESCRIPTION: SEQ ID NO:180:

Cys Tyr Cys Xaa Xaa Xaa Phe Cys Val Cys Val Xaa Trp Leu
1               5                   10

(2) INFORMATION FOR SEQ ID NO:181:

(i) SEQUENCE CHARACTERISTICS:
        (A) LENGTH: 14 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..14
        (D) OTHER INFORMATION: /product= "Cyclic"

(ix) FEATURE:
        (A) NAME/KEY: Modified-site
        (B) LOCATION: 4
        (D) OTHER INFORMATION: /product= "Xaa=O=Ornithine"

(ix) FEATURE:
        (A) NAME/KEY: Modified-site
        (B) LOCATION: 5
        (D) OTHER INFORMATION: /product= "Xaa=O=Ornithine"

(ix) FEATURE:
        (A) NAME/KEY: Modified-site
        (B) LOCATION: 6
        (D) OTHER INFORMATION: /product= "Xaa=O=Ornithine"

(ix) FEATURE:
        (A) NAME/KEY: Modified-site
        (B) LOCATION: 12
        (D) OTHER INFORMATION: /product= "Xaa=O=Ornithine"

(xi) SEQUENCE DESCRIPTION: SEQ ID NO:181:

Cys Tyr Cys Xaa Xaa Xaa Phe Cys Val Cys Val Xaa Trp Leu
1               5                   10

(2) INFORMATION FOR SEQ ID NO:182:

(i) SEQUENCE CHARACTERISTICS:
    (A) LENGTH: 15 amino acids
    (B) TYPE: amino acid
    (C) STRANDEDNESS: unknown
    (D) TOPOLOGY: circular (ii) MOLECULE TYPE: peptide (ix) FEATURE:
    (A) NAME/KEY: Peptide
    (B) LOCATION: 1..15
    (D) OTHER INFORMATION: /product= "Cyclic"

(xi) SEQUENCE DESCRIPTION: SEQ ID NO:182:

Cys Tyr Cys Arg Gly Arg Phe Cys Val Cys Val Gly Arg Trp Leu
1               5                   10                  15

(2) INFORMATION FOR SEQ ID NO:183:

(i) SEQUENCE CHARACTERISTICS:
        (A) LENGTH: 15 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..15
        (D) OTHER INFORMATION: /product= "Cyclic"

(ix) FEATURE:
        (A) NAME/KEY: Modified-site
        (B) LOCATION: 5
        (D) OTHER INFORMATION: /product= "Xaa=D-Arginine"

(ix) FEATURE:
        (A) NAME/KEY: Modified-site
        (B) LOCATION: 6
        (D) OTHER INFORMATION: /product= "Xaa=D-Arginine"

(xi) SEQUENCE DESCRIPTION: SEQ ID NO:183:

Cys Val Cys Phe Xaa Xaa Arg Cys Tyr Cys Leu Trp Arg Gly Val
1               5                   10                  15

(2) INFORMATION FOR SEQ ID NO:184:

(i) SEQUENCE CHARACTERISTICS:
        (A) LENGTH: 15 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..15
        (D) OTHER INFORMATION: /product= "Cyclic"

(ix) FEATURE:
        (A) NAME/KEY: Modified-site
        (B) LOCATION: 5
        (D) OTHER INFORMATION: /product= "Xaa=D-Arginine"

(ix) FEATURE:
        (A) NAME/KEY: Modified-site
        (B) LOCATION: 6
        (D) OTHER INFORMATION: /product= "Xaa=D-Arginine"

(xi) SEQUENCE DESCRIPTION: SEQ ID NO:184:

Cys Val Cys Phe Xaa Xaa Arg Cys Tyr Cys Leu Trp Gly Arg Val
1               5                   10                  15

(2) INFORMATION FOR SEQ ID NO:185:

(i) SEQUENCE CHARACTERISTICS:
        (A) LENGTH: 15 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..15
        (D) OTHER INFORMATION: /product= "Cyclic"

(ix) FEATURE:
        (A) NAME/KEY: Peptide
        (B) LOCATION: 1..15
        (D) OTHER INFORMATION: /product= "all amino acids are
            D- enantiomers"

(xi) SEQUENCE DESCRIPTION: SEQ ID NO:185:

```
Cys Tyr Cys Arg Arg Arg Phe Cys Val Cys Val Gly Arg Trp Leu
1               5                   10                  15
```

(2) INFORMATION FOR SEQ ID NO:186:

(i) SEQUENCE CHARACTERISTICS:
        (A) LENGTH: 15 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..15
        (D) OTHER INFORMATION: /product= "Cyclic"

(xi) SEQUENCE DESCRIPTION: SEQ ID NO:186:

```
Cys Tyr Cys Arg Pro Arg Phe Cys Val Cys Val Gly Arg Trp Leu
1               5                   10                  15
```

(2) INFORMATION FOR SEQ ID NO:187:

(i) SEQUENCE CHARACTERISTICS:
        (A) LENGTH: 15 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..15
        (D) OTHER INFORMATION: /product= "Cyclic"

(xi) SEQUENCE DESCRIPTION: SEQ ID NO:187:

```
Cys Val Cys Phe Arg Pro Arg Cys Tyr Cys Leu Trp Arg Gly Val
1               5                   10                  15
```

(2) INFORMATION FOR SEQ ID NO:188:

(i) SEQUENCE CHARACTERISTICS:
        (A) LENGTH: 15 amino acids
        (B) TYPE: amino acid
        (C) STRANDEDNESS: unknown
        (D) TOPOLOGY: circular (ii) MOLECULE TYPE: peptide (ix) FEATURE:
            (A) NAME/KEY: Peptide
            (B) LOCATION: 1..15
            (D) OTHER INFORMATION: /product= "Cyclic"

(xi) SEQUENCE DESCRIPTION: SEQ ID NO:188:

Cys Val Cys Phe Pro Arg Arg Cys Tyr Cys Leu Trp Arg Gly Val
1               5                   10                  15

(2) INFORMATION FOR SEQ ID NO:189:

(i) SEQUENCE CHARACTERISTICS:
            (A) LENGTH: 14 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..14
            (D) OTHER INFORMATION: /product= "Cyclic"

(xi) SEQUENCE DESCRIPTION: SEQ ID NO:189:

Cys Val Cys Val Gly Pro Arg Cys Tyr Cys Leu Arg Gly Trp
1               5                   10

(2) INFORMATION FOR SEQ ID NO:190:

(i) SEQUENCE CHARACTERISTICS:
            (A) LENGTH: 14 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..14
            (D) OTHER INFORMATION: /product= "Cyclic"

(xi) SEQUENCE DESCRIPTION: SEQ ID NO:190:

Cys Tyr Cys Arg Arg Arg Phe Cys Val Cys Val Arg Trp Leu
1               5                   10

(2) INFORMATION FOR SEQ ID NO:191:

(i) SEQUENCE CHARACTERISTICS:
            (A) LENGTH: 14 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..14
            (D) OTHER INFORMATION: /product= "Cyclic"

(xi) SEQUENCE DESCRIPTION: SEQ ID NO:191:

Cys Tyr Cys Arg Arg Arg Phe Cys Val Cys Val Arg Gly Trp
1               5                   10

(2) INFORMATION FOR SEQ ID NO:192:

(i) SEQUENCE CHARACTERISTICS:
            (A) LENGTH: 14 amino acids
            (B) TYPE: amino acid
            (C) STRANDEDNESS: unknown (D) TOPOLOGY: circular (ii) MOLECULE TYPE: peptide (ix) FEATURE:
            (A) NAME/KEY: Peptide
            (B) LOCATION: 1..14
            (D) OTHER INFORMATION: /product= "Cyclic"

(xi) SEQUENCE DESCRIPTION: SEQ ID NO:192:

Cys Tyr Cys Arg Arg Arg Phe Cys Val Cys Trp Arg Gly Val
1               5                   10

(2) INFORMATION FOR SEQ ID NO:193:

(i) SEQUENCE CHARACTERISTICS:
            (A) LENGTH: 14 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..14
            (D) OTHER INFORMATION: /product= "Cyclic"

(xi) SEQUENCE DESCRIPTION: SEQ ID NO:193:

Cys Tyr Cys Arg Pro Arg Phe Cys Val Cys Trp Gly Arg Val
1               5                   10

(2) INFORMATION FOR SEQ ID NO:194:

(i) SEQUENCE CHARACTERISTICS:
            (A) LENGTH: 14 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..14
            (D) OTHER INFORMATION: /product= "Cyclic"

(xi) SEQUENCE DESCRIPTION: SEQ ID NO:194:

Cys Tyr Cys Arg Arg Arg Phe Cys Val Cys Val Arg Gly Trp
1               5                   10

(2) INFORMATION FOR SEQ ID NO:195:

(i) SEQUENCE CHARACTERISTICS:
            (A) LENGTH: 14 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..14
            (D) OTHER INFORMATION: /product= "Cyclic"

(xi) SEQUENCE DESCRIPTION: SEQ ID NO:195:

Cys Val Cys Arg Pro Arg Trp Cys Tyr Cys Leu Trp Ser Val
1               5                   10

(2) INFORMATION FOR SEQ ID NO:196:

(i) SEQUENCE CHARACTERISTICS:
          (A) LENGTH: 15 amino acids
          (B) TYPE: amino acid
          (C) STRANDEDNESS: unknown
          (D) TOPOLOGY: circular (ii) MOLECULE TYPE: peptide (ix) FEATURE:
          (A) NAME/KEY: Peptide
          (B) LOCATION: 1..15
          (D) OTHER INFORMATION: /product= "Cyclic"

(xi) SEQUENCE DESCRIPTION: SEQ ID NO:196:

Cys Tyr Cys Arg Arg Arg Phe Cys Val Cys Val Gly Arg Trp Leu
1               5                   10                  15

(2) INFORMATION FOR SEQ ID NO:197:

(i) SEQUENCE CHARACTERISTICS:
          (A) LENGTH: 15 amino acids
          (B) TYPE: amino acid
          (C) STRANDEDNESS: unknown
          (D) TOPOLOGY: circular (ii) MOLECULE TYPE: peptide (ix) FEATURE:
          (A) NAME/KEY: Peptide
          (B) LOCATION: 1..15
          (D) OTHER INFORMATION: /product= "Cyclic"

(ix) FEATURE:
          (A) NAME/KEY: Peptide
          (B) LOCATION: 5
          (D) OTHER INFORMATION: /product = "Xaa=D-Arginine"

(xi) SEQUENCE DESCRIPTION: SEQ ID NO:197:

Cys Tyr Cys Arg Xaa Arg Phe Cys Val Cys Val Gly Arg Trp Leu
1               5                   10                  15

(2) INFORMATION FOR SEQ ID NO:198:

(i) SEQUENCE CHARACTERISTICS:
          (A) LENGTH: 14 amino acids
          (B) TYPE: amino acid
          (C) STRANDEDNESS: unknown
          (D) TOPOLOGY: circular (ii) MOLECULE TYPE: peptide (ix) FEATURE:
          (A) NAME/KEY: Peptide
          (B) LOCATION: 1..14
          (D) OTHER INFORMATION: /product= "Cyclic"

(xi) SEQUENCE DESCRIPTION: SEQ ID NO:198:

Cys Tyr Cys Ser Arg Arg Tyr Cys Val Cys Tyr Pro Arg Val
1               5                   10

(2) INFORMATION FOR SEQ ID NO:199:

(i) SEQUENCE CHARACTERISTICS:
          (A) LENGTH: 15 amino acids
          (B) TYPE: amino acid
          (C) STRANDEDNESS: unknown
          (D) TOPOLOGY: circular (ii) MOLECULE TYPE: peptide (ix) FEATURE:
          (A) NAME/KEY: Peptide
          (B) LOCATION: 1..15
          (D) OTHER INFORMATION: /product= "Cyclic"

(xi) SEQUENCE DESCRIPTION: SEQ ID NO:199:

Cys Tyr Cys Val Arg Arg Tyr Cys Val Cys Tyr Gly Arg Trp Val
1               5                   10                  15

(2) INFORMATION FOR SEQ ID NO:200:

(i) SEQUENCE CHARACTERISTICS:
        (A) LENGTH: 15 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..15
        (D) OTHER INFORMATION: /product= "Cyclic"

(ix) FEATURE:
        (A) NAME/KEY: Peptide
        (B) LOCATION: 5
        (D) OTHER INFORMATION: /product="Xaa=D-Arginine"

(xi) SEQUENCE DESCRIPTION: SEQ ID NO:200:

Cys Tyr Cys Gly Xaa Arg Tyr Cys Val Cys Tyr Ala Arg Trp Val
1               5                   10                  15

(2) INFORMATION FOR SEQ ID NO:201:

(i) SEQUENCE CHARACTERISTICS:
        (A) LENGTH: 15 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..15
        (D) OTHER INFORMATION: /product= "Cyclic"

(xi) SEQUENCE DESCRIPTION: SEQ ID NO:201:

Cys Val Cys Arg Ser Arg Phe Cys Tyr Cys Leu Trp Arg Gly Val
1               5                   10                  15

(2) INFORMATION FOR SEQ ID NO:202:

(i) SEQUENCE CHARACTERISTICS:
        (A) LENGTH: 15 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..15
        (D) OTHER INFORMATION: /product= "Cyclic"

(xi) SEQUENCE DESCRIPTION: SEQ ID NO:202:

Cys Val Cys Arg Pro Arg Phe Cys Tyr Cys Leu Trp Arg Gly Val
1               5                   10                  15

(2) INFORMATION FOR SEQ ID NO:203:

(i) SEQUENCE CHARACTERISTICS:
        (A) LENGTH: 15 amino acids
        (B) TYPE: amino acid (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..15
        (D) OTHER INFORMATION: /product= "Cyclic"

(xi) SEQUENCE DESCRIPTION: SEQ ID NO:203:

Cys Val Cys Tyr Arg Phe Arg Cys Tyr Cys Val Trp Arg Gly Phe
1               5                   10                  15

(2) INFORMATION FOR SEQ ID NO:204:

(i) SEQUENCE CHARACTERISTICS:
        (A) LENGTH: 17 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..17
        (D) OTHER INFORMATION: /product= "Cyclic"

(xi) SEQUENCE DESCRIPTION: SEQ ID NO:204:

Cys Tyr Cys Arg Pro Arg Phe Cys Val Cys Val Gly Arg Pro Gly
1               5                   10                  15

Trp Leu (2) INFORMATION FOR SEQ ID NO:205:

(i) SEQUENCE CHARACTERISTICS:
        (A) LENGTH: 16 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..16
        (D) OTHER INFORMATION: /product= "Cyclic"

(xi) SEQUENCE DESCRIPTION: SEQ ID NO:205:

Cys Tyr Cys Arg Pro Arg Phe Cys Val Cys Val Gly Arg Gly Trp
1               5                   10                  15

Leu (2) INFORMATION FOR SEQ ID NO:206:

(i) SEQUENCE CHARACTERISTICS:
        (A) LENGTH: 16 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..16
        (D) OTHER INFORMATION: /product= "Cyclic"

(xi) SEQUENCE DESCRIPTION: SEQ ID NO:206:

Cys Tyr Cys Arg Gly Arg Phe Cys Val Cys Val Arg Gly Gly Arg

```
            1               5              10              15
Val (2) INFORMATION FOR SEQ ID NO:207:

(i) SEQUENCE CHARACTERISTICS:
        (A) LENGTH: 16 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..16
        (D) OTHER INFORMATION: /product= "Cyclic"

(xi) SEQUENCE DESCRIPTION: SEQ ID NO:207:

Cys Tyr Cys Val Arg Arg Tyr Cys Val Cys Phe Gly Trp Ala Arg
1               5              10              15
Val (2) INFORMATION FOR SEQ ID NO:208:

(i) SEQUENCE CHARACTERISTICS:
        (A) LENGTH: 17 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..17
        (D) OTHER INFORMATION: /product= "Cyclic"

(xi) SEQUENCE DESCRIPTION: SEQ ID NO:208:

Cys Tyr Cys Arg Pro Arg Phe Cys Val Cys Val Gly Arg Arg Gly
1               5              10              15
Trp Leu (2) INFORMATION FOR SEQ ID NO:209:

(i) SEQUENCE CHARACTERISTICS:
        (A) LENGTH: 17 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..17
        (D) OTHER INFORMATION: /product= "Cyclic"

(xi) SEQUENCE DESCRIPTION: SEQ ID NO:209:

Cys Tyr Cys Arg Pro Arg Phe Cys Val Cys Val Gly Arg Arg Gly
1               5              10              15
Gly Leu (2) INFORMATION FOR SEQ ID NO:210:

(i) SEQUENCE CHARACTERISTICS:
        (A) LENGTH: 18 amino acids
        (B) TYPE: amino acid
        (C) STRANDEDNESS: unknown
```

(D) TOPOLOGY: circular (ii) MOLECULE TYPE: peptide (ix) FEATURE:
           (A) NAME/KEY: Peptide
           (B) LOCATION: 1..18
           (D) OTHER INFORMATION: /product= "Cyclic"

(xi) SEQUENCE DESCRIPTION: SEQ ID NO:210:

Cys Tyr Cys Arg Arg Arg Phe Cys Val Cys Val Gly Arg Arg Gly
1               5                  10                  15

Gly Arg Leu (2) INFORMATION FOR SEQ ID NO:211:

(i) SEQUENCE CHARACTERISTICS:
           (A) LENGTH: 18 amino acids
           (B) TYPE: amino acid
           (C) STRANDEDNESS: unknown
           (D) TOPOLOGY: circular (ii) MOLECULE TYPE: peptide (ix) FEATURE:
           (A) NAME/KEY: Peptide
           (B) LOCATION: 1..18
           (D) OTHER INFORMATION: /product= "Cyclic"

(xi) SEQUENCE DESCRIPTION: SEQ ID NO:211:

Cys Tyr Cys Arg Gly Arg Phe Cys Val Cys Val Gly Arg Gly Gly
1               5                  10                  15

Trp Arg Leu (2) INFORMATION FOR SEQ ID NO:212:

(i) SEQUENCE CHARACTERISTICS:
           (A) LENGTH: 18 amino acids
           (B) TYPE: amino acid
           (C) STRANDEDNESS: unknown
           (D) TOPOLOGY: circular (ii) MOLECULE TYPE: peptide (ix) FEATURE:
           (A) NAME/KEY: Peptide
           (B) LOCATION: 1..18
           (D) OTHER INFORMATION: /product= "Cyclic"

(ix) FEATURE:
           (A) NAME/KEY: Modified-site
           (B) LOCATION: 18
           (D) OTHER INFORMATION: /product= "Xaa=Cha=cyclohexylalanine"

(xi) SEQUENCE DESCRIPTION: SEQ ID NO:212:

Cys Tyr Cys Arg Gly Arg Phe Cys Val Cys Val Gly Arg Arg Gly
1               5                  10                  15

Leu Arg Xaa (2) INFORMATION FOR SEQ ID NO:213:

(i) SEQUENCE CHARACTERISTICS:
           (A) LENGTH: 19 amino acids
           (B) TYPE: amino acid
           (C) STRANDEDNESS: unknown
           (D) TOPOLOGY: circular (ii) MOLECULE TYPE: peptide (ix) FEATURE:
           (A) NAME/KEY: Peptide (B) LOCATION: 1..19
            (D) OTHER INFORMATION: /product= "Cyclic"

(xi) SEQUENCE DESCRIPTION: SEQ ID NO:213:

Cys Tyr Cys Arg Gly Arg Phe Cys Val Cys Val Gly Arg Arg Gly
1               5                   10                  15

Gly Trp Arg Leu (2) INFORMATION FOR SEQ ID NO:214:

(i) SEQUENCE CHARACTERISTICS:
            (A) LENGTH: 18 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..18
            (D) OTHER INFORMATION: /product= "Cyclic"

(xi) SEQUENCE DESCRIPTION: SEQ ID NO:214:

Cys Tyr Cys Arg Pro Arg Phe Cys Val Cys Val Gly Arg Gly Arg
1               5                   10                  15

Trp Arg Leu (2) INFORMATION FOR SEQ ID NO:215:

(i) SEQUENCE CHARACTERISTICS:
            (A) LENGTH: 18 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..18
            (D) OTHER INFORMATION: /product= "Cyclic"

(xi) SEQUENCE DESCRIPTION: SEQ ID NO:215:

Cys Tyr Cys Arg Thr Arg Phe Cys Val Cys Val Gly Arg Arg Gly
1               5                   10                  15

Trp Arg Leu (2) INFORMATION FOR SEQ ID NO:216:

(i) SEQUENCE CHARACTERISTICS:
            (A) LENGTH: 13 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..13
            (D) OTHER INFORMATION: /product= "Cyclic"

(xi) SEQUENCE DESCRIPTION: SEQ ID NO:216:

Cys Phe Cys Val Arg Arg Phe Cys Val Cys Phe Arg Val
1               5                   10

(2) INFORMATION FOR SEQ ID NO:217:

```
        (i) SEQUENCE CHARACTERISTICS:
             (A) LENGTH: 13 amino acids
             (B) TYPE: amino acid
             (C) STRANDEDNESS: unknown
             (D) TOPOLOGY: circular (ii) MOLECULE TYPE: peptide (ix) FEATURE:
             (A) NAME/KEY: Peptide
             (B) LOCATION: 1..13
             (D) OTHER INFORMATION: /product= "Cyclic"

(ix) FEATURE:
             (A) NAME/KEY: Modified-site
             (B) LOCATION: 13
             (D) OTHER INFORMATION: /product= "Xaa=Cha=cyclohexylalanine"

(xi) SEQUENCE DESCRIPTION: SEQ ID NO:217:

Cys Phe Cys Arg Pro Arg Tyr Cys Val Cys Val Arg Xaa
      1               5                   10

(2) INFORMATION FOR SEQ ID NO:218:

(i) SEQUENCE CHARACTERISTICS:
             (A) LENGTH: 13 amino acids
             (B) TYPE: amino acid
             (C) STRANDEDNESS: Not Relevant
             (D) TOPOLOGY: circular (ii) MOLECULE TYPE: peptide (ix) FEATURE:
             (A) NAME/KEY: Peptide
             (B) LOCATION: 1..13
             (D) OTHER INFORMATION: /product= "Cyclic"

(ix) FEATURE:
             (A) NAME/KEY: Modified-site
             (B) LOCATION: 5
             (D) OTHER INFORMATION: /product= "Xaa=D-Phenylalanine"

(ix) FEATURE:
             (A) NAME/KEY: Modified-site
             (B) LOCATION: 13
             (D) OTHER INFORMATION:/product="Xaa=Cha=cyclohexylalanine"

(xi) SEQUENCE DESCRIPTION: SEQ ID NO:218:

Cys Phe Cys Arg Xaa Pro Tyr Cys Val Cys Val Arg Xaa
1               5                   10

(2) INFORMATION FOR SEQ ID NO:219:

(i) SEQUENCE CHARACTERISTICS:
             (A) LENGTH: 13 amino acids
             (B) TYPE: amino acid
             (C) STRANDEDNESS: unknown
             (D) TOPOLOGY: circular (ii) MOLECULE TYPE: peptide (ix) FEATURE:
             (A) NAME/KEY: Modified-site
             (B) LOCATION: 13
             (D) OTHER INFORMATION:/product="Xaa=Cha=cyclohexylalanine"

(xi) SEQUENCE DESCRIPTION: SEQ ID NO:219:

Cys Phe Cys Val Thr Arg Tyr Cys Val Cys Val Arg Xaa
1               5                   10

(2) INFORMATION FOR SEQ ID NO:220:

(i) SEQUENCE CHARACTERISTICS:
             (A) LENGTH: 13 amino acids
```

(B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..13
        (D) OTHER INFORMATION: /product= "Cyclic"

(ix) FEATURE:
        (A) NAME/KEY: Modified-site
        (B) LOCATION: 5
        (D) OTHER INFORMATION: /product= "Xaa=MeGly"

(ix) FEATURE:
        (A) NAME/KEY: Modified-site
        (B) LOCATION: 6
        (D) OTHER INFORMATION: /product= "Xaa=D-Arginine"

(xi) SEQUENCE DESCRIPTION: SEQ ID NO:220:

Cys Phe Cys Val Xaa Xaa Tyr Cys Val Cys Tyr Arg Val
1               5                   10

(2) INFORMATION FOR SEQ ID NO:221:

(i) SEQUENCE CHARACTERISTICS:
        (A) LENGTH: 14 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..14
        (D) OTHER INFORMATION: /product= "Cyclic"

(ix) FEATURE:
        (A) NAME/KEY: Peptide
        (B) LOCATION: 5
        (D) OTHER INFORMATION: /product= "Xaa=D-Arginine"

(xi) SEQUENCE DESCRIPTION: SEQ ID NO:221:

Cys Tyr Cys Arg Xaa Arg Phe Cys Val Cys Val Arg Trp Leu
1               5                   10

(2) INFORMATION FOR SEQ ID NO:222:

(i) SEQUENCE CHARACTERISTICS:
        (A) LENGTH: 14 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..14
        (D) OTHER INFORMATION: /product= "Cyclic"

(xi) SEQUENCE DESCRIPTION: SEQ ID NO:222:

Cys Tyr Cys Arg Arg Arg Phe Cys Val Cys Val Arg Trp Leu
1               5                   10

(2) INFORMATION FOR SEQ ID NO:223:

(i) SEQUENCE CHARACTERISTICS:
        (A) LENGTH: 14 amino acids
        (B) TYPE: amino acid
        (C) STRANDEDNESS: unknown (D) TOPOLOGY: circular (ii) MOLECULE TYPE: peptide (ix) FEATURE:
            (A) NAME/KEY: Peptide
            (B) LOCATION: 1..14
            (D) OTHER INFORMATION: /product= "Cyclic"

(xi) SEQUENCE DESCRIPTION: SEQ ID NO:223:

Cys Tyr Cys Val Arg Arg Tyr Cys Val Cys Tyr Arg Trp Val
1               5                   10

(2) INFORMATION FOR SEQ ID NO:224:

(i) SEQUENCE CHARACTERISTICS:
            (A) LENGTH: 12 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..12
            (D) OTHER INFORMATION: /product= "Cyclic"

(xi) SEQUENCE DESCRIPTION: SEQ ID NO:224:

Cys Tyr Cys Lys Lys Lys Phe Cys Val Cys Val Leu
1               5                   10

(2) INFORMATION FOR SEQ ID NO:225:

(i) SEQUENCE CHARACTERISTICS:
            (A) LENGTH: 13 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..13
            (D) OTHER INFORMATION: /product= "Cyclic"

(xi) SEQUENCE DESCRIPTION: SEQ ID NO:225:

Cys Tyr Cys Lys Lys Lys Phe Cys Val Cys Val Trp Tyr
1               5                   10

(2) INFORMATION FOR SEQ ID NO:226:

(i) SEQUENCE CHARACTERISTICS:
            (A) LENGTH: 13 amino acids
            (B) TYPE: amino acid
            (C) STRANDEDNESS: unknown
            (D) TOPOLOGY: circular (ii) MOLECULE TYPE: peptide (ix) FEATURE:
            (A) NAME/KEY: Peptide
            (B) LOCATION: 1..13
            (D) OTHER INFORMATION: /product= "Cyclic"

(xi) SEQUENCE DESCRIPTION: SEQ ID NO:226:

Cys Tyr Cys Lys Lys Lys Phe Cys Val Cys Val Trp Leu
1               5                   10

(2) INFORMATION FOR SEQ ID NO:227:

(i) SEQUENCE CHARACTERISTICS:
        (A) LENGTH: 13 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..13
        (D) OTHER INFORMATION: /product= "Cyclic"

(xi) SEQUENCE DESCRIPTION: SEQ ID NO:227:

Cys Tyr Cys Lys Lys Lys Phe Cys Val Cys Val Lys Leu
1               5                   10

(2) INFORMATION FOR SEQ ID NO:228:

(i) SEQUENCE CHARACTERISTICS:
        (A) LENGTH: 12 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..12
        (D) OTHER INFORMATION: /product= "Cyclic"

(ix) FEATURE:
        (A) NAME/KEY: Modified-site
        (B) LOCATION: 12
        (D) OTHER INFORMATION: /product= "Xaa=Cha=cyclohexylalanine"

(xi) SEQUENCE DESCRIPTION: SEQ ID NO:228:

Cys Phe Cys Lys Pro Phe Cys Val Cys Val Lys Xaa
1               5                   10

(2) INFORMATION FOR SEQ ID NO:229:

(i) SEQUENCE CHARACTERISTICS:
        (A) LENGTH: 12 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..12
        (D) OTHER INFORMATION: /product= "Cyclic"

(xi) SEQUENCE DESCRIPTION: SEQ ID NO:229:

Cys Tyr Cys Arg Arg Arg Phe Cys Val Cys Val Leu
1               5                   10

(2) INFORMATION FOR SEQ ID NO:230:

(i) SEQUENCE CHARACTERISTICS:
        (A) LENGTH: 18 amino acids
        (B) TYPE: amino acid
        (C) STRANDEDNESS: unknown
        (D) TOPOLOGY: circular (ii) MOLECULE TYPE: peptide (ix) FEATURE:
        (A) NAME/KEY: Peptide
        (B) LOCATION: 1..18
        (D) OTHER INFORMATION: /product= "Cyclic"

(xi) SEQUENCE DESCRIPTION: SEQ ID NO:230:

Cys Tyr Cys Arg Gly Arg Phe Cys Val Cys Val Gly Arg Gly Gly
1               5                   10                  15

Trp Arg Leu (2) INFORMATION FOR SEQ ID NO:231:

(i) SEQUENCE CHARACTERISTICS:

(xi) SEQUENCE DESCRIPTION: SEQ ID NO:231:

This sequence has been intentionally skipped (2) INFORMATION FOR SEQ ID NO:232:

(i) SEQUENCE CHARACTERISTICS:

(xi) SEQUENCE DESCRIPTION: SEQ ID NO:232:

This sequence has been intentionally skipped (2) INFORMATION FOR SEQ ID NO:233:

(i) SEQUENCE CHARACTERISTICS:

(xi) SEQUENCE DESCRIPTION: SEQ ID NO:233:

This sequence has been intentionally skipped (2) INFORMATION FOR SEQ ID NO:234:

(i) SEQUENCE CHARACTERISTICS:

(xi) SEQUENCE DESCRIPTION: SEQ ID NO:234:

This sequence has been intentionally skipped (2) INFORMATION FOR SEQ ID NO:235:

(i) SEQUENCE CHARACTERISTICS:

(xi) SEQUENCE DESCRIPTION: SEQ ID NO:235:

This sequence has been intentionally skipped (2) INFORMATION FOR SEQ ID NO:236:

(i) SEQUENCE CHARACTERISTICS:

(xi) SEQUENCE DESCRIPTION: SEQ ID NO:236:

This sequence has been intentionally skipped (2) INFORMATION FOR SEQ ID NO:237:

(i) SEQUENCE CHARACTERISTICS:

(xi) SEQUENCE DESCRIPTION: SEQ ID NO:237:

This sequence has been intentionally skipped (2) INFORMATION FOR SEQ ID NO:238:

(i) SEQUENCE CHARACTERISTICS:

(xi) SEQUENCE DESCRIPTION: SEQ ID NO:238:

This sequence has been intentionally skipped (2) INFORMATION FOR SEQ ID NO:239:

(i) SEQUENCE CHARACTERISTICS:

(xi) SEQUENCE DESCRIPTION: SEQ ID NO:239:

This sequence has been intentionally skipped (2) INFORMATION FOR SEQ ID NO:240:

(i) SEQUENCE CHARACTERISTICS:
  (A) LENGTH: 13 amino acids
  (B) TYPE: amino acid
  (C) STRANDEDNESS: unknown
  (D) TOPOLOGY: circular (ii) MOLECULE TYPE: peptide (ix) FEATURE:
  (A) NAME/KEY: Peptide
  (B) LOCATION: 1..13
  (D) OTHER INFORMATION: /product= "Cyclic"

(xi) SEQUENCE DESCRIPTION: SEQ ID NO:240:

```
Cys Tyr Cys Arg Arg Arg Phe Cys Val Cys Val Trp Leu
1               5                   10
```

(2) INFORMATION FOR SEQ ID NO:241:

(i) SEQUENCE CHARACTERISTICS:
  (A) LENGTH: 15 amino acids
  (B) TYPE: amino acid
  (C) STRANDEDNESS: unknown
  (D) TOPOLOGY: circular (ii) MOLECULE TYPE: peptide (ix) FEATURE:
  (A) NAME/KEY: Peptide
  (B) LOCATION: 1..15
  (D) OTHER INFORMATION: /product= "Cyclic"

(xi) SEQUENCE DESCRIPTION: SEQ ID NO:241:

```
Cys Val Cys Phe Arg Arg Arg Cys Tyr Cys Leu Trp Arg Gly Val
1               5                   10                  15
```